(12) United States Patent
Bessis et al.

(10) Patent No.: US 7,834,035 B2
(45) Date of Patent: Nov. 16, 2010

(54) ALLOSTERIC MODULATORS OF METABOTROPIC GLUTAMATE RECEPTORS

(75) Inventors: Anne-Sophie Bessis, Ferney-Voltaire (FR); Beatrice Bonnet, Andilly (FR); Emmanuel Le Poul, Cessy (FR); Jean-Philippe Rocher, Vetraz-Monthoux (FR); Mark Epping-Jordan, Nyon (CH)

(73) Assignee: Addex Pharma SA, Geneva (CH)

( * ) Notice: Subject to any disclaimer, the term of this patent is extended or adjusted under 35 U.S.C. 154(b) by 1007 days.

(21) Appl. No.: 10/578,589

(22) PCT Filed: Nov. 4, 2004

(86) PCT No.: PCT/IB2004/003822

§ 371 (c)(1),
(2), (4) Date: Dec. 13, 2006

(87) PCT Pub. No.: WO2005/044797

PCT Pub. Date: May 19, 2005

(65) Prior Publication Data

US 2007/0219187 A1    Sep. 20, 2007

(30) Foreign Application Priority Data

Nov. 6, 2003 (GB) ................... 0325956.1

(51) Int. Cl.
*A61K 31/4523* (2006.01)
*C07D 401/04* (2006.01)
(52) U.S. Cl. ...................................... 514/326; 546/209
(58) Field of Classification Search ................. 514/326; 546/209
See application file for complete search history.

(56) References Cited

U.S. PATENT DOCUMENTS

| 3,991,064 A | 11/1976 | Brown et al. | |
|---|---|---|---|
| 2002/0077337 A1* | 6/2002 | Rigby et al. | 514/316 |
| 2003/0149049 A1 | 8/2003 | Arkin et al. | |

FOREIGN PATENT DOCUMENTS

| GB | 950872 | 2/1964 |
|---|---|---|
| WO | WO-91/04250 | 4/1991 |
| WO | WO-99/02497 | 1/1999 |
| WO | WO-00/25768 | 5/2000 |
| WO | WO-01/02375 | 1/2001 |
| WO | WO-01/54498 A1 | 8/2001 |
| WO | WO-01/54507 | 8/2001 |
| WO | WO-03/027080 | 4/2003 |
| WO | WO-03/037888 | 5/2003 |
| WO | WO-03/066595 | 8/2003 |
| WO | WO-2004/011441 | 2/2004 |
| WO | WO-2004/014902 | 2/2004 |
| WO | WO-2004/029031 | 4/2004 |
| WO | WO-2004/038374 | 5/2004 |
| WO | WO-2004/052864 | 6/2004 |
| WO | WO-2004/058754 | 7/2004 |
| WO | WO-2004/085408 | 10/2004 |
| WO | WO-2004/087048 A2 | 10/2004 |

OTHER PUBLICATIONS

Baker et al., Journal of Organic Chemistry, 17:52-57, XP002321098 (1952).
Eastman et al., Bioorganic and Medicinal Chemistry Letters, 14:5485-5488, XP002321099 (2004).
Rogers, et al., Neurobiology of Aging, vol. 17, No. 5, pp. 681-686 (1996).
Yan, et al., J. Comb. Chem., vol. 5, No. 5, pp. 547-559 (2003).
Phillips, et al., J. Med. Chem., vol. 35, No. 4, pp. 743-750 (1992).
Toja, E. et al., Farmaco Sci., vol. 39, No. 5, pp. 450-462 (1984).
CAS Registry No. 695195-63-2, Chemical Library, Supplier: Chemical Block Ltd, CAS Registry (2004).
Opposition (brief) filed in the name of Sanofi-Aventis in corresponding European Patent No. 1 685 105 B1, dated Jul. 20, 2009.
Opposition (brief) filed in the name of Dr. Thorsten Bausch in corresponding European Patent No. 1 685 105 B1, dated Jul. 14, 2009.

* cited by examiner

*Primary Examiner*—Taofiq A Solola
(74) *Attorney, Agent, or Firm*—Edwards Angell Palmer & Dodge LLP; Peter F. Corless; Mark D. Russett

(57) ABSTRACT

The present invention relates to new compounds of formula (I) wherein A, B, P, Q, W, $R_1$ and $R_2$ are defined in the description; invention compounds are useful in the prevention or treatment of central nervous system disorders as well as other disorders modulated by mGluR5 receptors.

7 Claims, 3 Drawing Sheets

ALLOSTERIC MODULATORS OF METABOTROPIC GLUTAMATE RECEPTORS

FIELD OF THE INVENTION

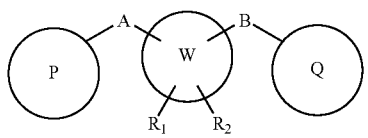

I

The present invention provides new compounds of formula I as modulators of metabotropic receptors—subtype 5 ("mGluR5") which are useful for the treatment central nervous system disorders such as for example, cognitive decline, both positive and negative symptoms in schizophrenia as well as other disorders modulated by mGluR5 receptors.

BACKGROUND OF THE INVENTION

Glutamate, the major amino-acid transmitter in the mammalian central nervous system (CNS), mediates excitatory synoptic neurotransmission through the activation of ionotropic glutamate receptors receptor-channels (iGluRs, namely NMDA, AMPA and kainate) and metabotropic glutamate receptors (mGluRs). iGluRs are responsible for fast excitatory transmission (Nakanishi S et al., (1998) Brain Res Brain Res Rev., 26:230-235) while mGluRs have a more modulatory role that contributes to the fine-tuning of synoptic efficacy. Glutamate performs numerous physiological functions such as long-term potentiation (LTP), a process believed to underlie learning and memory but also cardiovascular regulation, sensory perception, and the development of synoptic plasticity. In addition, glutamate plays an important role in the patho-physiology of different neurological and psychiatric diseases, especially when an imbalance in glutamatergic neurotransmission occurs.

The mGluRs are seven-transmembrane G protein-coupled receptors. The eight members of the family are classified into three groups (Groups I, II & III) according to their sequence homology and pharmacological properties (Schoepp D D et al. (1999) Neuropharmacology, 38:1431-1476). Activation of mGluRs lead to a large variety of intracellular responses and activation of different transductional cascades. Among mGluR members, the mGluR5 subtype is of high interest for counterbalancing the deficit or excesses of neurotransmission in neuropsychatric diseases. mGluR5 belongs to Group I and its activation initiates cellular responses through G-protein mediated mechanisms. mGluR5 is coupled to phospholipase C and stimulates phosphoinositide hydrolysis and intracellular calcium mobilization.

mGluR5 proteins have been demonstrated to be localized in post-synaptic elements adjacent to the post-synaptic density (Lujan R et al. (1996) Eur J Neurosci. 8:1488-500; Lujan R et al. (1997) J Chem Neuroanat., 13:219-41) and are rarely detected in the pre-synoptic elements (Romano C et al. (1995) J Comp Neurol. 355:455-69). MGluR5 receptors can therefore modify the post-synoptic responses to neurotransmitter or regulate neurotransmitter release.

In the CNS, mGluR5 receptors are abundant mainly throughout cortex, hippocampus, caudate-putamen and nucleus accumbens. As these brain areas have been shown to be involved in emotion, motivational processes and in numerous aspects of cognitive function, mGluR5 modulators are predicted to be of therapeutic interest.

A variety of potential clinical indications have been suggested to be targets for the development of subtype selective mGluR modulators. These include epilepsy, neuropathic and inflammatory pain, numerous psychiatric disorders (eg anxiety and schizophrenia), movement disorders (eg Parkinson disease), neuroprotection (stroke and head injury), migraine and addiction/drug dependency (for reviews, see Brauner-Osborne H et al. (2000) J Med Chem. 43:2609-45; Bordi F and Ugolini A. (1999) Prog Neurobiol. 59:55-79; Spooren W et al. (2003) Behav Pharmacol: 14:257-77).

The hypothesis of hypofunction of the glutamatergic system as reflected by NMDA receptor hypofunction as a putative cause of schizophrenia has received increasing support over the past few years (Goff D C and Coyle J T (2001) Am J Psychiatry, 158:1367-1377; Carlsson A et al. (2001) Annu Rev Pharmacol Toxicol., 41:237-260 for a review). Evidence implicating dysfunction of glutamatergic neurotransmission is supported by the finding that antagonists of the NMDA subtype of glutamate receptor can reproduce the full range of symptoms as well as the physiologic manifestation of schizophrenia such as hypofrontality, impaired prepulse inhibition and enhanced subcortical dopamine release. In addition, clinical studies have suggested that mGluR5 allele frequency is associated with schizophrenia among certain cohorts (Devon R S et al. (2001) Mol Psychiatry. 6:311-4) and that an increase in mGluR5 message has been found in cortical pyramidal cells layers of schizophrenic brain (Ohnuma T et al. (1998) Brain Res Mol Brain Res. 56:207-17).

The involvement of mGluR5 in neurological and psychiatric disorders is supported by evidence showing that in vivo activation of group I mGluRs induces a potentiation of NMDA receptor function in a variety of brain regions mainly through the activation of mGluR5 receptors (Mannaioni G et al. (2001) Neurosci. 21:5925-34; Awad H et al. (2000) J Neurosci 20:7871-7879; Pisani A et al (2001) Neuroscience 106:579-87; Benquet P et al (2002) J Neurosci. 22:9679-86)

The role of glutamate in memory processes also has been firmly established during the past decade (Martin S J et al. (2000) Annu. Rev. Neurosci. 23:649-711; Baudry M and Lynch G. (2001) Neurobiol Learn Mem., 76:284-297). The use of mGluR5 null mutant mice have strongly supported a role of mGluR5 in learning and memory. These mice show a selective loss in two tasks of spatial learning and memory, and reduced CA1 LTP (Lu et al. (1997) J. Neurosci., 17:5196-5205; Schulz B et al. (2001) Neuropharmacology. 41:1-7; Jia Z et al. (2001) Physiol Behav., 73:793-802; Rodrigues et al. (2002) J Neurosci., 22:5219-5229).

The finding that mGluR5 is responsible for the potentiation of NMDA receptor mediated currents raises the possibility that agonists of this receptor could be useful as cognitive-enhancing agents, but also, as novel antipsychotic agents that act by selectively enhancing NMDA receptor function.

The activation of NMDARs could potentate hypofunctional NMDARs in neuronal circuitry relevant to schizophrenia. Recent in vivo data strongly suggest that mGluR5 activation may be a novel and efficacious approach to treat to treat cognitive decline and both positive and negative symptoms in schizophrenia (Kinney G G et al. (2002) 43:292).

mGluR5 receptor is therefore been considered as a potential drug target for treatment of psychiatric and neurological disorders including treatable diseases in this connection are Anxiety Disorders, Attentional disorders, Eating Disorders, Mood Disorders, Psychotic Disorders, Cognitive Disorders, Personality Disorders and Substance-related disorders Most of the current modulators of mGluR5 function have been developed as structural analogues of glutamate, quisqualate or phenylglycine (Schoepp D D et al. (1999) Neuropharmacology, 38:1431-1476) and it has been very challenging to develop in vivo active and selective mGluR5 modulators acting at the glutamate binding site. A new avenue for developing selective modulators is to identify molecules that act through allosteric mechanisms, modulating the receptor by binding to site different from the highly conserved orthosteric binding site.

Positive allosteric modulators of mGluRs have emerged recently as novel pharmacological entities offering this attractive alternative. This type of molecule has been discovered for mGluR1, mGluR2, mGluR4, and mGluR5 (Knoflach F et al. (2001) Proc Natl Acad Sci USA. 98:13402-13407; O'Brien J A et al. (2003) Mol Pharmacol. 64:731-40; Johnson K et al. (2002) Neuropharmacology 43:291; Johnson M P et al. (2003) J Med Chem. 46:3189-92; Marino M J et al. (2003) Proc Natl Acad Sci USA. 100(23):13668-73; for a review see Mutel V (2002) Expert Opin. Ther. Patents 12:1-8). DFB and related molecules were described as mGluR5 positive allosteric modulator but with low in vitro potency (O'Brien J A et al. (2003) Mol Pharmacol. 64:731-40). Recently benzamide modulators of mGluR5 receptors have been patented (WO 2004/087048). A new class of positive allosteric modulators has also been described; these molecules are aminopyrazole derivatives (C. W. Lindsley et al. (2004) J. Med. Chem. Epub Oct. 23, 2004 jm049400d).

None of the specifically disclosed compounds are structurally related to the compounds of the present invention.

The present invention relates to a method of treating or preventing a condition in a mammal, including a human, the treatment or prevention of which is affected or facilitated by the neuromodulatory effect of mGluR5 modulators.

SUMMARY OF THE INVENTION

In accordance with the present invention, there is provided new compounds substituted by a bridge A or B, with an unsaturated five or six aryl or heteroaryl ring containing atoms independently selected from carbon, nitrogen, sulfur and oxygen atoms. The invention also discloses pharmaceuticals acceptable form these new compounds.

Invention compounds are useful for treating CNS disorders which are affected by the neuromodulatory effect of mGluR5 positive allosteric modulators such as cognitive decline and also to treat both positive and negative symptoms in schizophrenia.

FIGURES

DETAILED DESCRIPTION OF THE INVENTION

Figure 1:
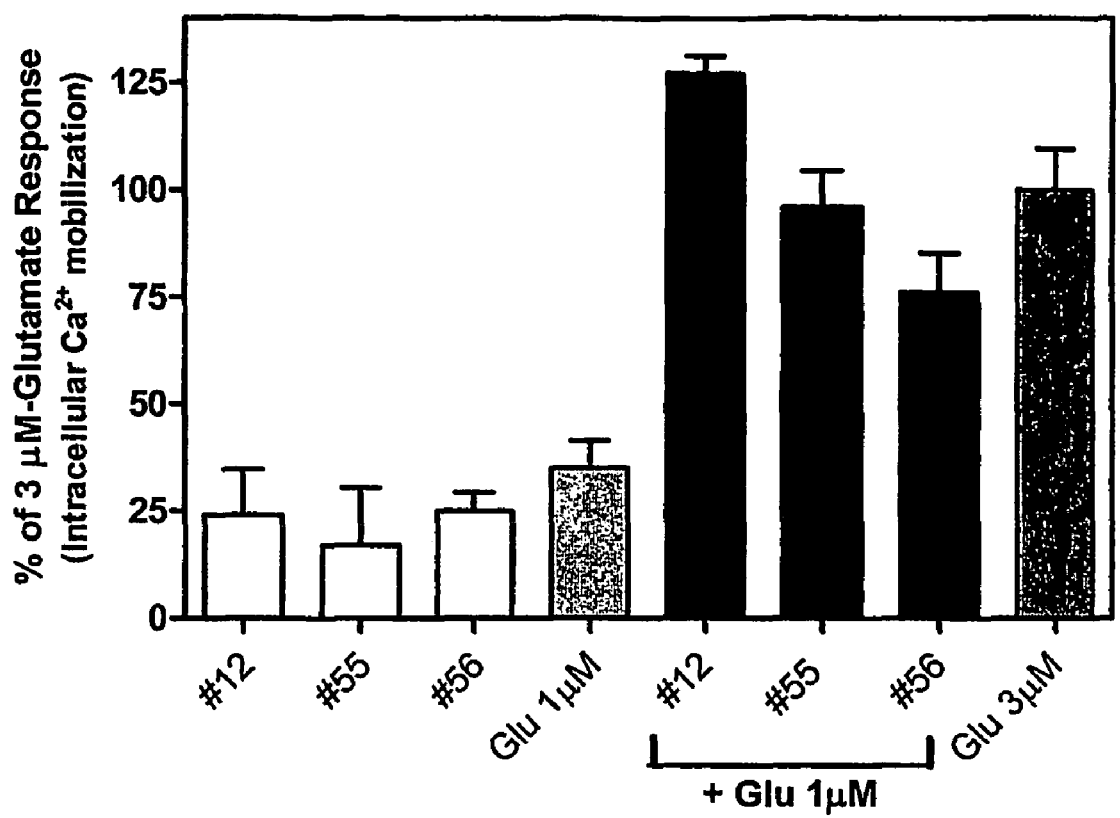
FIG. 1 shows an increase of 1 μM glutamate-induced $Ca^{2+}$ mobilization in rat cultured astrocytes in the presence of 3 μM of examples #12, 55 and 56 of the present invention.

According to the present invention, there are provided new compounds of the general formula I

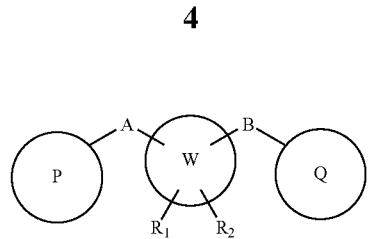

Or pharmaceutically acceptable salts, hydrates or solvates of such compounds

Wherein

W represents a 5 to 7 atoms cycloalkyl or heterocycloalkyl ring;

$R_1$ and $R_2$ represent independently hydrogen, $C_1$-$C_6$-alkyl, $C_2$-$C_6$-alkenyl, $C_2$-$C_6$-alkynyl, arylalkyl, heteroarylalkyl, hydroxy, amino, aminoalkyl, hydroxyalkyl, $C_1$-$C_6$-alkoxy or $R_1$ and $R_2$ together can form a $C_3$-$C_7$-cycloalkyl ring, a carbonyl bond C=O or a carbon double bond;

P and Q are each independently selected and denote a cycloalkyl, an aryl or heteroaryl group of formula

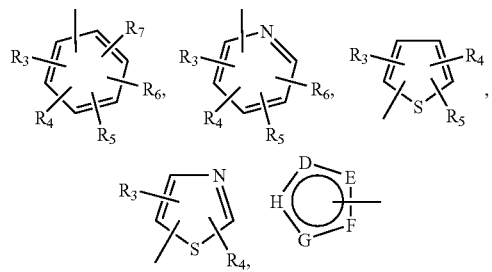

$R_3$, $R_4$, $R_5$, $R_6$, and $R_7$ independently are hydrogen, halogen, —CN, nitro, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, -heteroaryl, heteroarylalkyl, arylalkyl, aryl, —$OR_8$, —$NR_8R_9$, —C(=$NR_{10}$)$NR_8R_9$, N(=$NR_{10}$)$NR_8R_9$, —$NR_8COR_9$, $NR_8CO_2R_9$, $NR_8SO_2R_9$, —$NR_{10}$CO $NR_8R_9$, —$SR_8$, —S(=O)$R_8$, —S(=O)$_2R_8$, —S(=O)$_2$ $NR_8R_9$, —C(=O)$R_8$, —C(=O)$_2R_8$, —C(=O)$NR_8R_9$, —C(=$NR_8$)$R_9$, or C(=$NOR_8$)$R_9$ substituents; wherein optionally two substituents are combined to the intervening atoms to form a bicyclic heterocycloalkyl, aryl or heteroaryl ring; wherein each ring is optionally further substituted with 1-5 independent halogen, —CN, $C_1$-$C_6$-alkyl, —O($C_0$-$C_6$-alkyl), —O($C_3$-$C_7$-cycloalkylalkyl), —O(aryl), —O(heteroaryl), —O($C_1$-$C_3$-alkylaryl), —O($C_1$-$C_3$-alkylheteroaryl), —N($C_0$-$C_6$-alkyl)($C_0$-$C_3$-alkylaryl) or —N($C_0$-$C_6$-alkyl)($C_0$-$C_3$-alkylheteroaryl) groups;

$R_8$, $R_9$, $R_{10}$ each independently is hydrogen, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, heterocycloalkyl, heteroaryl, heteroarylalkyl, arylalkyl or halogen, —CN, $C_1$-$C_6$-alkyl, —O($C_0$-$C_6$-alkyl), —O($C_3$-$C_7$-cycloalkylalkyl), —O(aryl), —O(heteroaryl), —N($C_0$-$C_6$-alkyl)($C_0$-$C_6$-alkyl), —N($C_0$-$C_6$-alkyl)($C_3$-$C_7$-cycloalkyl) or —N($C_0$-$C_6$-alkyl)(aryl) substituents;

D, E, F, G and H represent independently —C($R_3$)=, —C($R_3$)=C($R_4$)—, —C(=O)—, —C(=S)—, —O—, —N=, —N($R_3$)— or —S—;

A is azo —N=N—, ethyl, ethenyl, ethynyl, —$NR_8$C (=O)—, $NR_8$S(=O)$_2$—, —C(=O)$NR_8$—, —S—, —S(=O)—, —S(=O)$_2$—, —S(=O)$_2$NR$_8$—, —C(=O)—O—, —O—C(=O)=, =C(=NR$_8$)NR$_9$—, C(=NOR$_8$)NR$_9$—, —NR$_8$C(=NOR$_9$)—, =N—O—, —O—N=CH— or a group aryl or heteroaryl of formula

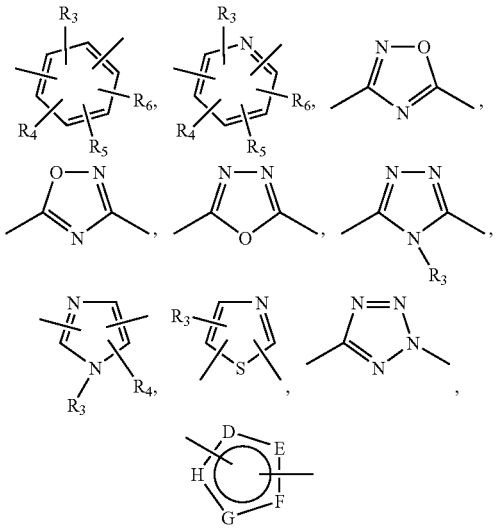

$R_3$, $R_4$, $R_5$ and $R_6$ independently are as defined above; D, E, F, G and H represent independently a carbon group, oxygen, nitrogen, sulphur or a double bond;

B represents a single bond, —C(=O)—C$_0$-C$_2$-alkyl-, —C(=O)—C$_2$-C$_6$-alkenyl-, —C(=O)—C$_2$-C$_6$-alkynyl-, —C(=O)—O—, —C(=O)NR$_8$—C$_0$-C$_2$-alkyl-, —C(=NR$_8$)NR$_9$—S(=O)—C$_0$-C$_2$-alkyl-, —S(=O)$_2$—C$_0$-C$_2$-alkyl-, —S(=O)$_2$NR$_8$—C$_0$-C$_2$-alkyl-, C(=NR$_8$)—C$_0$-C$_2$-alkyl-, —C(=NOR$_8$)—C$_0$-C$_2$-alkyl- or —C(=NOR$_8$)NR$_9$—C$_0$-C$_2$-alkyl-;

$R_8$ and $R_9$, independently are as defined above;

Any N may be an N-oxide.

The present invention includes both possible stereoisomers and includes not only racemic compounds but the individual enantiomers as well.

In the above definition, the term "$C_1$-$C_6$-alkyl" includes group such as methyl, ethyl, propyl, isopropyl, butyl, isobutyl, sec-butyl, tert-butyl, pentyl, isopentyl, neopentyl, tert-pentyl, hexyl or the like.

"$C_2$-$C_6$-alkenyl" includes group such as ethenyl, 1-propenyl, allyl, isopropenyl, 1-butenyl, 3-butenyl, 4-pentenyl and the like.

"$C_2$-$C_6$-alkynyl" includes group such as ethynyl, propynyl, butynyl, pentynyl and the like.

"Halogen" includes atoms such as fluorine, bromine, chlorine and iodine.

"Cycloalkyl" refers to an optionally substituted carbocycle containing no heteroatoms, includes mono-, bi-, and tricyclic saturated carbocycles, as well as fused ring systems. Such fused ring systems can include on ring that is partially or fully unsaturated such as a benzene ring to form fused ring systems such as benzo fused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantine, indenyl, fluorenyl, 1,2,3,4-tetrahydronaphthalene and the like.

"Heterocycloalkyl" refers to an optionally substituted carbocycle containing at least one heteroatom selected independently from O, N, S. It includes mono-, bi-, and tricyclic saturated carbocycles, as well as fused ring systems. Such fused ring systems can include on ring that is partially or fully unsaturated such as a benzene ring to form fused ring systems such as benzo fused carbocycles. Examples of heterocycloalkyl include piperidine, piperazine, morpholine, tetrahydrothiophene, indoline, isoquinoline and the like.

"Aryl" includes $C_6$-$C_{10}$ aryl group such as phenyl, 1-naphtyl, 2-naphtyl and the like.

"Arylalkyl" includes $C_6$-$C_{10}$ aryl-$C_1$-$C_3$-alkyl group such as benzyl group, 1-phenylethyl group, 2-phenylethyl group, 1-phenylpropyl group, 2-phenylpropyl group, 3-phenylpropyl group, 1-naphtylmethyl group, 2-naphtylmethyl group or the like.

"Heteroaryl" includes 5-10 membered heterocyclic group containing 1 to 4 heteroatoms selected from oxygen, nitrogen or sulphur to form a ring such as furyl (furan ring), benzofuranyl (benzofuran), thienyl (thiophene), benzothiophenyl (benzothiophene), pyrrolyl (pyrrole ring), imidazolyl (imidazole ring), pyrazolyl (pyrazole ring), thiazolyl (thiazole ring), isothiazolyl (isothiazole ring), triazolyl (triazole ring), tetrazolyl (tetrazole ring), pyridil (pyridine ring), pyrazynyl (pyrazine ring), pyrimidinyl (pyrimidine ring), pyridazinyl (pyridazine ring), indolyl (indole ring), isoindolyl (isoindole ring), benzoimidazolyl (benzimidazole ring), purinyl group (purine ring), quinolyl (quinoline ring), phtalazinyl (phtalazine ring), naphtyridinyl (naphtyridine ring), quinoxalinyl (quinoxaline ring), cinnolyl (cinnoline ring), pteridinyl (pteridine ring), oxazolyl (oxazole ring), isoxazolyl (isoxazole ring), benzoxazolyl (benzoxazole ring), benzothiazolyly (benzothiaziole ring), furazanyl (furazan ring) and the like.

"Heteroarylalkyl" includes heteroaryl-$C_1$-$C_3$-alkyl group, wherein examples of heteroaryl are the same as those illustrated in the above definition, such as 2-furylmethyl group, 3-furylmethyl group, 2-thienylmethyl group, 3-thienylmethyl group, 1-imidazolylmethyl group, 2-imidazolylmethyl group, 2-thiazolylmethyl group, 2-pyridylmethyl group, 3-pyridylmethyl group, 1-quinolylmethyl group or the like.

"Solvate" refers to a complex of variable stochiometry formed by a solute (e.g. a compound of formula I) and a solvent. The solvent is a pharmaceutically acceptable solvent as water preferably; such solvent may not interfere with the biological activity of the solute.

"Optionally" means that the subsequently described event(s) may or may not occur, and includes both event(s), which occur, and events that do not occur.

The term "substituted" refers to substitution with the named substituent or substituents, multiple degrees of substitution being allowed unless otherwise stated.

Preferred compounds of the present invention are compounds of formula I-A depicted below

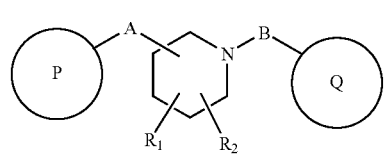

I-A

Or pharmaceutically acceptable salts, hydrates or solvates of such compounds

Wherein $R_1$ and $R_2$ represent independently hydrogen, $C_1$-$C_6$-alkyl, $C_2$-$C_6$-alkenyl, $C_2$-$C_6$-alkynyl, arylalkyl, heteroarylalkyl, hydroxy, amino, aminoalkyl, hydroxyalkyl, $C_1$-$C_6$-alkoxy or $R_1$ and $R_2$ together can form a $C_3$-$C_7$-cycloalkyl ring, a carbonyl bond C=O or a carbon double bond;

P and Q are each independently selected and denote a cycloalkyl, an aryl or heteroaryl group of formula

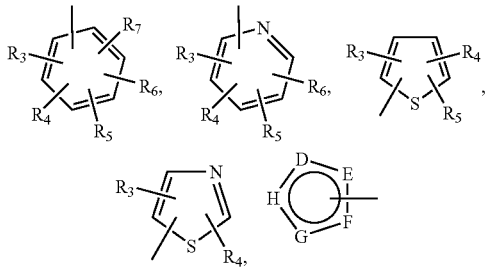

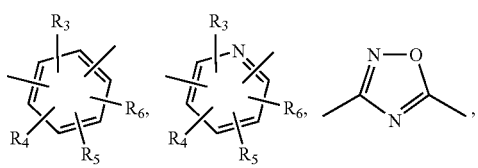

$R_3$, $R_4$, $R_5$, $R_6$ and $R_7$ independently are hydrogen, halogen, —CN, nitro, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, -heteroaryl, heteroarylalkyl, arylalkyl, aryl, —OR$_8$, —NR$_8$R$_9$, —C(=NR$_{10}$)NR$_8$R$_9$, N(=NR$_{10}$)NR$_8$R$_9$, —NR$_8$COR$_9$, NR$_8$CO$_2$R$_9$, NR$_8$SO$_2$R$_9$, —NR$_{10}$CO NR$_8$R$_9$, —SR$_8$, —S(=O)R$_8$, —S(=O)$_2$R$_8$, —S(=O)$_2$ NR$_8$R$_9$, —C(=O)R$_8$, —C(=O)$_2$R$_8$, —C(=O)NR$_8$R$_9$, —C(=NR$_8$)R$_9$, or C(=NOR$_8$)R$_9$ substituents; wherein optionally two substituents are combined to the intervening atoms to form a bicyclic heterocycloalkyl, aryl or heteroaryl ring; wherein each ring is optionally further substituted with 1-5 independent halogen, —CN, $C_1$-$C_6$-alkyl, —O($C_0$-$C_6$-alkyl), —O($C_3$-$C_7$-cycloalkylalkyl), —O(aryl), —O(heteroaryl), —O($C_1$-$C_3$-alkylaryl), —O($C_1$-$C_3$-alkylheteroaryl), —N($C_0$-$C_6$-alkyl)($C_0$-$C_3$-alkylaryl) or —N($C_0$-$C_6$-alkyl)($C_0$-$C_3$-alkylheteroaryl) groups;

$R_8$, $R_9$, $R_{10}$ each independently is hydrogen, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, heterocycloalkyl, heteroaryl, heteroarylalkyl, arylalkyl or aryl; any of which is optionally substituted with 1-5 independent halogen, —CN, $C_1$-$C_6$-alkyl, —O($C_0$-$C_6$-alkyl), —O($C_3$-$C_7$-cycloalkylalkyl), —O(aryl), —O(heteroaryl), —N($C_0$-$C_6$-alkyl)($C_0$-$C_6$-alkyl), —N($C_0$-$C_6$-alkyl)($C_3$-$C_7$-cycloalkyl) or —N($C_0$-$C_6$-alkyl)(aryl) substituents;

D, E, F, G and H represent independently —C(R$_3$)=, —C(R$_3$)=C(R$_4$)—, —C(=O)—, —C(=S)—, —O—, —N=, —N(R$_3$)— or —S—;

A is azo —N=N—, ethyl, ethenyl, ethynyl, —NR$_8$C(=O)—, NR$_8$S(=O)$_2$—, —C(=O)NR$_8$—, —S—, —S(=O)—, —S(=O)$_2$—, —S(=O)$_2$NR$_8$—, —C(=O)—O—, —O—C(=O)—, —C(=NR$_8$)NR$_9$—, C(=NOR$_8$)NR$_9$—, —NR$_8$C(=NOR$_9$)—, =N—O—, —O—N=CH— or a group aryl or heteroaryl of formula

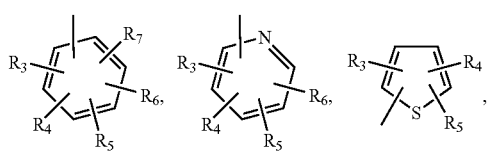

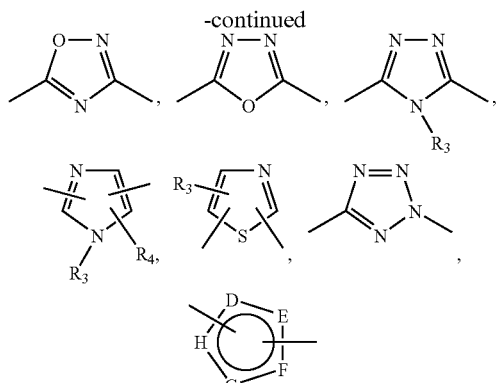

$R_3$, $R_4$, $R_5$ and $R_6$ independently are as defined above;

D, E, F, G and H represent independently a carbon group, oxygen, nitrogen, sulphur or a double bond;

B represents a single bond, —C(=O)—C$_0$-C$_2$-alkyl-, —C(=O)—C$_2$-C$_6$-alkenyl-, —C(=O)—C$_2$-C$_6$-alkynyl-, —C(=O)—O—, —C(=O)NR$_8$—C$_0$-C$_2$-alkyl-, —C(=NR$_8$)NR$_9$—S(=O)—C$_0$-C$_2$-alkyl-, —S(=O)$_2$—C$_0$-C$_2$-alkyl-, —S(=O)$_2$NR$_8$—C$_0$-C$_2$-alkyl-, C(=NR$_8$)—C$_0$-C$_2$-alkyl-, —C(=NOR$_8$)—C$_0$-C$_2$-alkyl- or —C(=NOR$_8$)NR$_9$—C$_0$-C$_2$-alkyl-;

$R_8$ and $R_9$, independently are as defined above;

Any N may be an N-oxide.

The present invention includes both possible stereoisomers and includes not only racemic compounds but the individual enantiomers as well.

More preferred compounds of the present invention are compounds of formula I-B

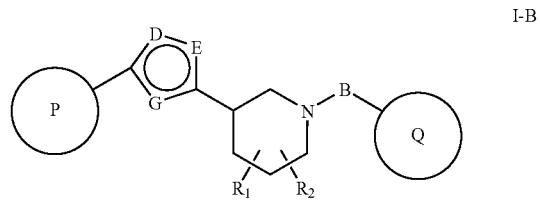

Or pharmaceutically acceptable salts, hydrates or solvates of such compounds

Wherein $R_1$ and $R_2$ represent independently hydrogen, $C_1$-$C_6$-alkyl, $C_2$-$C_6$-alkenyl, $C_2$-$C_6$-alkynyl, arylalkyl, heteroarylalkyl, hydroxy, amino, aminoalkyl, hydroxyalkyl, $C_1$-$C_6$-alkoxy or $R_1$ and $R_2$ together can form a $C_3$-$C_7$-cycloalkyl ring, a carbonyl bond C=O or a carbon double bond;

P and Q are each independently selected and denote a cycloalkyl, an aryl or heteroaryl group of formula

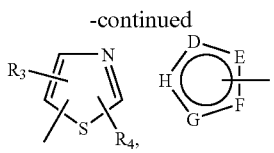

$R_3$, $R_4$, $R_5$, $R_6$, and $R_7$ independently are hydrogen, halogen, —CN, nitro, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, -heteroaryl, heteroarylalkyl, arylalkyl, aryl, —$OR_8$, —$NR_8R_9$, —C(=$NR_{10}$)$NR_8R_9$, N(=$NR_{10}$)$NR_8R_9$, —$NR_8COR_9$, $NR_8CO_2R_9$, $NR_8SO_2R_9$, —$NR_{10}CONR_8R_9$, —$SR_8$, —S(=O)$R_8$, —S(=O)$_2R_8$, —S(=O)$_2NR_8R_9$, —C(=O)$R_8$, —C(=O)$_2R_8$, —C(=O)$NR_8R_9$, —C(=$NR_8$)$R_9$, or C(=$NOR_8$)$R_9$ substituents; wherein optionally two substituents are combined to the intervening atoms to form a bicyclic heterocycloalkyl, aryl or heteroaryl ring; wherein each ring is optionally further substituted with 1-5 independent halogen, —CN, $C_1$-$C_6$-alkyl, —O($C_0$-$C_6$-alkyl), —O($C_3$-$C_7$-cycloalkylalkyl), —O(aryl), —O(heteroaryl), —O($C_1$-$C_3$-alkylaryl), —O($C_1$-$C_3$-alkylheteroaryl), —N($C_0$-$C_6$-alkyl)($C_0$-$C_3$-alkylaryl) or —N($C_0$-$C_6$-alkyl)($C_0$-$C_3$-alkylheteroaryl) groups;

$R_8$, $R_9$, $R_{10}$ each independently is hydrogen, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, heterocycloalkyl, heteroaryl, heteroarylalkyl, arylalkyl or aryl; any of which is optionally substituted with 1-5 independent halogen, —CN, $C_1$-$C_6$-alkyl, —O($C_0$-$C_6$-alkyl), —O($C_3$-$C_7$-cycloalkylalkyl), —O(aryl), —O(heteroaryl), —N($C_0$-$C_6$-alkyl)($C_0$-$C_6$-alkyl), —N($C_0$-$C_6$-alkyl)($C_3$-$C_7$-cycloalkyl) or —N($C_0$-$C_6$-alkyl)(aryl) substituents;

D, E, F, G and H in P and Q represent independently —C($R_3$)=, —C($R_3$)=C($R_4$)—, —C(=O)—, —C(=S)—, —O—, —N=, —N($R_3$)— or —S—;

D, E, and G in A independently are as defined for A above;

B represents a single bond, —C(=O)—$C_0$-$C_2$-alkyl-, —C(=O)—$C_2$-$C_6$-alkenyl-, —C(=O)—$C_2$-$C_6$-alkynyl-, —C(=O)—O—, —C(=O)$NR_8$—$C_0$-$C_2$-alkyl-, —C(=$NR_8$)$NR_9$—S(=O)—$C_0$-$C_2$-alkyl-, —S(=O)$_2$—$C_0$-$C_2$-alkyl-, —S(=O)$_2NR_8$—$C_0$-$C_2$-alkyl-, C(=$NR_8$)—$C_0$-$C_2$-alkyl-, —C(=$NOR_8$)—$C_0$-$C_2$-alkyl- or —C(=$NOR_8$)$NR_9$—$C_0$-$C_2$-alkyl-;

$R_8$ and $R_9$, independently are as defined above;
Any N may be an N-oxide.

The present invention includes both possible stereoisomers and includes not only racemic compounds but the individual enantiomers as well.

Particularly preferred compounds of the present invention are compounds of formula I-C

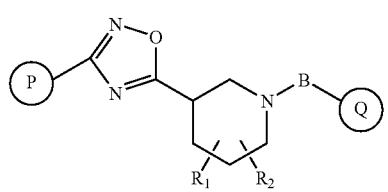

I-C

Or pharmaceutically acceptable salts, hydrates or solvates of such compounds

Wherein
$R_1$ and $R_2$ represent independently hydrogen, $C_1$-$C_6$-alkyl, $C_2$-$C_6$-alkenyl, $C_2$-$C_6$-alkynyl, arylalkyl, heteroarylalkyl, hydroxy, hydroxyalkyl, $C_1$-$C_6$-alkoxy or $R_1$ and $R_2$ together can form a carbonyl bond C=O or a carbon double bond;

P and Q are each independently selected and denote a cycloalkyl, an aryl or heteroaryl group of formula

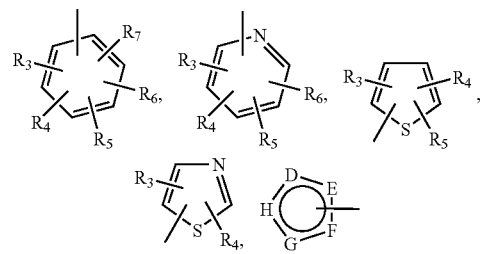

$R_3$, $R_4$, $R_5$, and $R_7$ independently are hydrogen, halogen, —CN, nitro, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, -heteroaryl, heteroarylalkyl, arylalkyl, aryl, —$OR_8$, —$NR_8R_9$, —C(=$NR_{10}$)$NR_8R_9$, N(=$NR_{10}$)$NR_8R_9$, —$NR_8COR_9$, $NR_8CO_2R_9$, $NR_8SO_2R_9$, —$NR_{10}CONR_8R_9$, —$SR_8$, —S(=O)$R_8$, —S(=O)$_2R_8$, —S(=O)$_2NR_8R_9$, —C(=O)$R_8$, —C(=O)$_2R_8$, —C(=O)$NR_8R_9$, —C(=$NR_8$)$R_9$, or C(=$NOR_8$)$R_9$ substituents; wherein optionally two substituents are combined to the intervening atoms to form a bicyclic heterocycloalkyl, aryl or heteroaryl ring; wherein each ring is optionally further substituted with 1-5 independent halogen, —CN, $C_1$-$C_6$-alkyl, —O($C_0$-$C_6$-alkyl), —O($C_3$-$C_7$-cycloalkylalkyl), —O(aryl), —O(heteroaryl), —O($C_1$-$C_3$-alkylaryl), —O($C_1$-$C_3$-alkylheteroaryl), —N($C_0$-$C_6$-alkyl)($C_0$-$C_3$-alkylaryl) or —N($C_0$-$C_6$-alkyl)($C_0$-$C_3$-alkylheteroaryl) groups;

$R_8$, $R_9$, $R_{10}$ each independently is hydrogen, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, heterocycloalkyl, heteroaryl, heteroarylalkyl, arylalkyl or aryl; any of which is optionally substituted with 1-5 independent halogen, —CN, $C_1$-$C_6$-alkyl, —O($C_0$-$C_6$-alkyl), —O($C_3$-$C_7$-cycloalkylalkyl), —O(aryl), —O(heteroaryl), —N($C_0$-$C_6$-alkyl)($C_0$-$C_6$-alkyl), —N($C_0$-$C_6$-alkyl)($C_3$-$C_7$-cycloalkyl) or —N($C_0$-$C_6$-alkyl)(aryl) substituents;

D, E, F, G and H represent independently —C($R_3$)=, —C($R_3$)=C($R_4$)—, —C(=O)—, —C(=S)—, —O—, —N=, —N($R_3$)— or —S—;

B represents a single bond, —C(=O)—$C_0$-$C_2$-alkyl-, —C(=O)—$C_2$-$C_6$-alkenyl-, —C(=O)—$C_2$-$C_6$-alkynyl-, —C(=O)—O—, —C(=O)$NR_8$—$C_0$-$C_2$-alkyl-, —C(=$NR_8$)$NR_9$—S(=O)—$C_0$-$C_2$-alkyl-, —S(=O)$_2$—$C_0$-$C_2$-alkyl-, —S(=O)$_2NR_8$—$C_0$-$C_2$-alkyl-, C(=$NR_8$)—$C_0$-$C_2$-alkyl-, —C(=$NOR_8$)—$C_0$-$C_2$-alkyl- or —C(=$NOR_8$)$NR_9$—$C_0$-$C_2$-alkyl-;

$R_8$ and $R_9$, independently are as defined above;
Any N may be an N-oxide.

The present invention includes both possible stereoisomers and includes not only racemic compounds but the individual enantiomers as well.

Further preferred compounds of the present invention are compounds of formula I-D

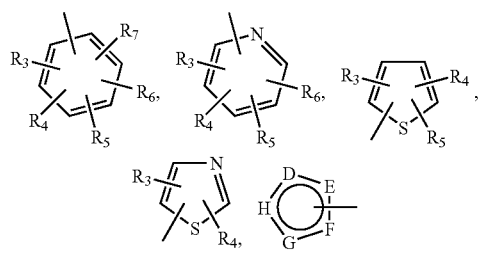

Or pharmaceutically acceptable salts, hydrates or solvates of such compounds

Wherein

P and Q are each independently selected and denote a cycloalkyl, an aryl or heteroaryl group of formula

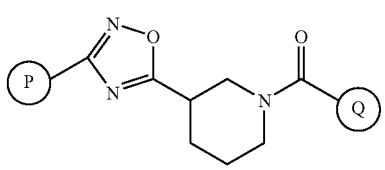

$R_3$, $R_4$, $R_5$, $R_6$, and $R_7$ independently are hydrogen, halogen, —CN, nitro, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, -heteroaryl, heteroarylalkyl, arylalkyl, aryl, —$OR_8$, —$NR_8R_9$, —C(=$NR_{10}$)$NR_8R_9$, N(=$NR_{10}$)$NR_8R_9$, —$NR_8COR_9$, $NR_8CO_2R_9$, $NR_8SO_2R_9$, —$NR_{10}CO$ $NR_8R_9$, —$SR_8$, —S(=O)$R_8$, —S(=O)$_2R_8$, —S(=O)$_2$ $NR_8R_9$, —C(=O)$R_8$, —C(=O)$_2R_8$, —C(=O)$NR_8R_9$, —C(=$NR_8$)$R_9$, or C(=$NOR_8$)$R_9$ substituents; wherein optionally two substituents are combined to the intervening atoms to form a bicyclic heterocycloalkyl, aryl or heteroaryl ring; wherein each ring is optionally further substituted with 1-5 independent halogen, —CN, $C_1$-$C_6$-alkyl, —O($C_0$-$C_6$-alkyl), —O($C_3$-$C_7$-cycloalkylalkyl), —O(aryl), —O(heteroaryl), —O($C_1$-$C_3$-alkylaryl), —O($C_1$-$C_3$-alkylheteroaryl), —N($C_0$-$C_6$-alkyl)($C_0$-$C_3$-alkylaryl) or —N($C_0$-$C_6$-alkyl)($C_0$-$C_3$-alkylheteroaryl) groups;

$R_8$, $R_9$, $R_{10}$ each independently is hydrogen, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, heterocycloalkyl, heteroaryl, heteroarylalkyl, arylalkyl or aryl; any of which is optionally substituted with 1-5 independent halogen, —CN, $C_1$-$C_6$-alkyl, —O($C_0$-$C_6$-alkyl), —O($C_3$-$C_7$-cycloalkylalkyl), —O(aryl), —O(heteroaryl), —N($C_0$-$C_6$-alkyl)($C_0$-$C_6$-alkyl), —N($C_0$-$C_6$-alkyl)($C_3$-$C_7$-cycloalkyl) or —N($C_0$-$C_6$-alkyl)(aryl) substituents;

D, E, F, G and H represent independently —C($R_3$)=, —C($R_3$)=C($R_4$)—, —C(=O)—, —C(=S)—, —O—, —N=, —N($R_3$)— or —S—;

Any N may be an N-oxide.

The present invention includes both possible stereoisomers and includes not only racemic compounds but the individual enantiomers as well.

In another aspect, the compound of this invention is represented by formula (I-E) or a pharmaceutically acceptable salt thereof

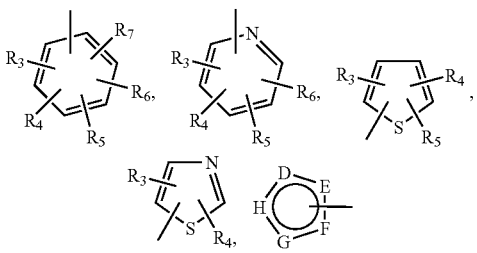

Wherein

P and Q are each independently selected and denote a cycloalkyl, an aryl or heteroaryl group of formula $R_3$, $R_4$, $R_5$, $R_6$, and $R_7$ independently are hydrogen, halogen, —CN, nitro, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, -heteroaryl, heteroarylalkyl, arylalkyl, aryl, —$OR_8$, —$NR_8R_9$, —C(=$NR_{10}$)$NR_8R_9$, N(=$NR_{10}$)$NR_8R_9$, —$NR_8COR_9$, $NR_8CO_2R_9$, $NR_8SO_2R_9$, —$NR_{10}CO$ $NR_8R_9$, —$SR_8$, —S(=O)$R_8$, —S(=O)$_2R_8$, —S(=O)$_2$ $NR_8R_9$, —C(=O)$R_8$, —C(=O)$_2R_8$, —C(=O)$NR_8R_9$, —C(=$NR_8$)$R_9$, or C(=$NOR_8$)$R_9$ substituents; wherein optionally two substituents are combined to the intervening atoms to form a bicyclic heterocycloalkyl, aryl or heteroaryl ring; wherein each ring is optionally further substituted with 1-5 independent halogen, —CN, $C_1$-$C_6$-alkyl, —O($C_0$-$C_6$-alkyl), —O($C_3$-$C_7$-cycloalkylalkyl), —O(aryl), —O(heteroaryl), —O($C_1$-$C_3$-alkylaryl), —O($C_1$-$C_3$-alkylheteroaryl), —N($C_0$-$C_6$-alkyl)($C_0$-$C_3$-alkylaryl) or —N($C_0$-$C_6$-alkyl)($C_0$-$C_3$-alkylheteroaryl) groups;

$R_8$, $R_9$, $R_{10}$ each independently is hydrogen, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, heterocycloalkyl, heteroaryl, heteroarylalkyl, arylalkyl or aryl; any of which is optionally substituted with 1-5 independent halogen, —CN, $C_1$-$C_6$-alkyl, —O($C_0$-$C_6$-alkyl), —O($C_3$-$C_7$-cycloalkylalkyl), —O(aryl), —O(heteroaryl), —N($C_0$-$C_6$-alkyl)($C_0$-$C_6$-alkyl), —N($C_0$-$C_6$-alkyl)($C_3$-$C_7$-cycloalkyl) or —N($C_0$-$C_6$-alkyl)(aryl) substituents;

D, E, F, G and H represent independently —C($R_3$)=, —C($R_3$)=C($R_4$)—, —C(=O)—, —C(=S)—, —O—, —N=, —N($R_3$)— or —S—;

Any N may be an N-oxide.

The present invention includes both possible stereoisomers and includes not only racemic compounds but the individual enantiomers as well.

In further aspect, the compound of this invention is represented by formula (I-F) or a pharmaceutically acceptable salt thereof

I-F

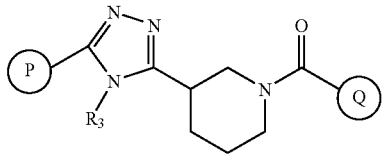

Wherein

P and Q are each independently selected and denote a cycloalkyl, an aryl or heteroaryl group of formula

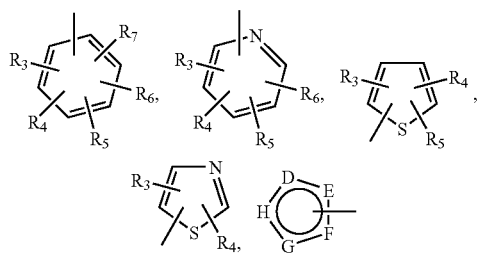

$R_3$, $R_4$, $R_5$, $R_6$, and $R_7$ independently are hydrogen, halogen, —CN, nitro, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, -heteroaryl, heteroarylalkyl, arylalkyl, aryl, —$OR_8$, —$NR_8R_9$, —$C(=NR_{10})NR_8R_9$, $N(=NR_{10})NR_8R_9$, —$NR_8COR_9$, $NR_8CO_2R_9$, $NR_8SO_2R_9$, —$NR_{10}CO NR_8R_9$, —$SR_8$, —$S(=O)R_8$, —$S(=O)_2R_8$, —$S(=O)_2 NR_8R_9$, —$C(=O)R_8$, —$C(=O)_2R_8$, —$C(=O)NR_8R_9$, —$C(=NR_8)R_9$, or $C(=NOR_8)R_9$ substituents; wherein optionally two substituents are combined to the intervening atoms to form a bicyclic heterocycloalkyl, aryl or heteroaryl ring; wherein each ring is optionally further substituted with 1-5 independent halogen, —CN, $C_1$-$C_6$ alkyl —$O(C_0$-$C_6$-alkyl), —$O(C_3$-$C_7$-cycloalkylalkyl), —O(aryl), —O(heteroaryl), —$O(C_1$-$C_3$-alkylaryl), —$O(C_1$-$C_3$-alkylheteroaryl), —$N(C_0$-$C_6$-alkyl)($C_0$-$C_3$-alkylaryl) or —$N(C_0$-$C_6$-alkyl)($C_0$-$C_3$-alkylheteroaryl) groups;

$R_8$, $R_9$, $R_{10}$ each independently is hydrogen, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, heterocycloalkyl, heteroaryl, heteroarylalkyl, arylalkyl or aryl; any of which is optionally substituted with 1-5 independent halogen, —CN, $C_1$-$C_6$-alkyl, —$O(C_0$-$C_6$-alkyl), —$O(C_3$-$C_7$-cycloalkylalkyl), —O(aryl), —O(heteroaryl), —$N(C_0$-$C_6$-alkyl)($C_0$-$C_6$-alkyl), —$N(C_0$-$C_6$-alkyl)($C_3$-$C_7$-cycloalkyl) or —$N(C_0$-$C_6$-alkyl)(aryl) substituents;

D, E, F, G and H represent independently —$C(R_3)$=, —$C(R_3)$=$C(R_4)$—, —$C(=O)$—, —$C(=S)$—, —O—, —N=, —$N(R_3)$— or —S—;

Any N may be an N-oxide.

The present invention includes both possible stereoisomers and includes not only racemic compounds but the individual enantiomers as well.

Another aspect of the invention are compounds of the formula I-G

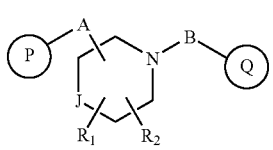

Wherein $R_1$ and $R_2$ represent independently hydrogen, $C_1$-$C_6$-alkyl, $C_2$-$C_6$-alkenyl, $C_2$-$C_6$-alkynyl, arylalkyl, heteroarylalkyl, hydroxy, amino, aminoalkyl, hydroxyalkyl, $C_1$-$C_6$-alkoxy or $R_1$ and $R_2$ together can form a $C_3$-$C_7$-cycloalkyl ring, a carbonyl bond C=O or a carbon double bond;

P and Q are each independently selected and denote an aryl or heteroaryl group of formula

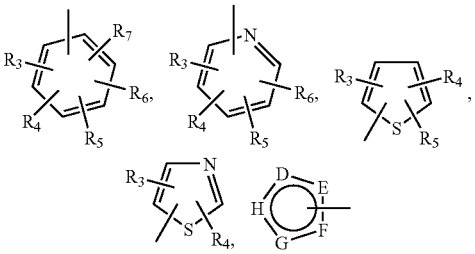

$R_3$, $R_4$, $R_5$, $R_6$, and $R_7$ independently are hydrogen, halogen, —CN, nitro, $C_1$-$C_6$-alkyl, $C_3$-$C_6$-cycloalkyl, $C_3$-$C_7$-cycloalkylalkyl, $C_1$-$C_6$-alkenyl, $C_1$-$C_6$-alkynyl, halo-$C_1$-$C_6$-alkyl, -heteroaryl, heteroarylalkyl, arylalkyl, aryl, —$OR_8$, —$NR_8R_9$, —$C(=NR_{10})NR_8R_9$, $N(=NR_{10})NR_8R_9$, —$NR_8COR_9$, $NR_8CO_2R_9$, $NR_8SO_2R_9$, —$NR_{10}CO NR_8R_9$, —$SR_8$, —$S(=O)R_8$, —$S(=O)_2R_8$, —$S(=O)_2 NR_8R_9$, —$C(=O)R_8$, —$C(=O)_2R_8$, —$C(=O)NR_8R_9$, —$C(=NR_8)R_9$, or $C(=NOR_8)R_9$ substituents; wherein optionally two substituents are combined to the intervening atoms to form a bicyclic aryl or heteroaryl ring; wherein each ring is optionally further substituted with 1-5 independent halogen, —CN, $C_1$-$C_6$-alkyl, —$O(C_0$-$C_6$-alkyl), —$O(C_3$-$C_7$-cycloalkylalkyl), —O(aryl), —O(heteroaryl), —$O(C_1$-$C_3$-alkylaryl), —$O(C_1$-$C_3$-alkylheteroaryl), —$N(C_0$-$C_6$-alkyl)($C_0$-$C_3$-alkylaryl) or —$N(C_0$-$C_6$-alkyl)($C_0$-$C_3$-alkylheteroaryl) groups;

$R_8$, $R_9$, $R_{10}$ each independently is hydrogen, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, heteroaryl, heteroarylalkyl, arylalkyl or aryl; any of which is optionally substituted with 1-5 independent halogen, —CN, $C_1$-$C_6$-alkyl, —$O(C_0$-$C_6$-alkyl), —$O(C_3$-$C_7$-cycloalkylalkyl), —O(aryl), —O(heteroaryl), —$N(C_0$-$C_6$-alkyl) ($C_0$-$C_6$-alkyl), —$N(C_0$-$C_6$-alkyl)($C_3$-$C_7$-cycloalkyl) or —$N(C_0$-$C_6$-alkyl)(aryl) substituents;

D, E, F, G and H represent independently —$C(R_3)$=, $C(R_3)$=$C(R_4)$—, —$C(=O)$—, —$C(=S)$—, —O—, —N=, —$N(R_3)$— or —S—;

A is azo —N=N—, ethyl, ethenyl, ethynyl, —$NR_8C(=O)$—, $NR_8S(=O)_2$—, —$C(=O)NR_8$—, —S—, —$S(=O)$—, —$S(=O)_2$—, —$S(=O)_2NR_8$—, —$C(=O)$—O—, —O—$C(=O)$—, —$C(=NR_8)NR_9$—, C(=NOR$_8$)NR$_9$—, —NR$_8$C(=NOR$_9$)—, =N—O—, —O—N=CH— or a group aryl or heteroaryl of formula

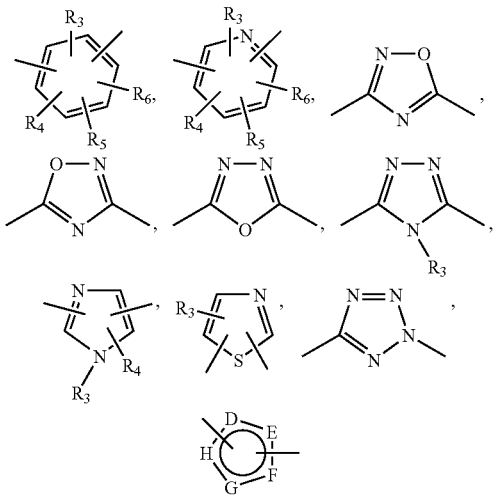

R$_3$, R$_4$, R$_5$ and R$_6$ independently are as defined above;
D, E, F, G and H independently are as defined previously in A;
B represents a single bond, —C(=O)—C$_0$-C$_2$-alkyl-, —C(=O)—C$_2$-C$_6$-alkenyl-; —C(=O)—C$_2$-C$_6$-alkynyl-, —C(=O)—O—, —C(=O)NR$_8$—C$_0$-C$_2$-alkyl-, —C(=NR$_8$)NR$_9$—S(=O)—C$_0$-C$_2$-alkyl-, —S(=O)$_2$—C$_0$-C$_2$-alkyl-, —S(=O)$_2$NR$_8$—C$_0$-C$_2$-alkyl-, C(=NR$_8$)—C$_0$-C$_2$-alkyl-, —C(=NOR$_8$)—C$_0$-C$_2$-alkyl- or —C(=NOR$_8$)NR$_9$—C$_0$-C$_2$-alkyl-;
R$_8$ and R$_9$, independently are as defined above;
J represents —C(R$_{11}$, R$_{12}$), —O—, —N(R$_{11}$)— or —S—;
R$_{11}$, R$_{12}$ independently are hydrogen, C$_1$-C$_6$-alkyl, C$_3$-C$_6$-cycloalkyl, C$_3$-C$_7$-cycloalkylalkyl, C$_2$-C$_6$-alkenyl, C$_2$-C$_6$-alkynyl, halo-C$_1$-C$_6$-alkyl, heteroaryl, heteroarylalkyl, arylalkyl or aryl; any of which is optionally substituted with 1-5 independent halogen, —CN, C$_1$-C$_6$ alkyl, —O(C$_0$-C$_6$-alkyl), —O(C$_3$-C$_7$-cycloalkylalkyl), —O(aryl), —O(heteroaryl), —N(C$_0$-C$_6$-alkyl)(C$_0$-C$_6$-alkyl), —N(C$_0$-C$_6$-alkyl)(C$_3$-C$_7$-cycloalkyl) or —N(C$_0$-C$_6$-alkyl)(aryl) substituents;
Any N may be an N-oxide;
The present invention includes both possible stereoisomers and includes not only racemic compounds but the individual enantiomers as well.
An embodiment of the present invention includes compounds of the formula I-H

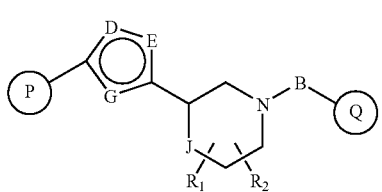

I-H

Wherein
R$_1$ and R$_2$ represent independently hydrogen, C$_0$-C$_6$-alkyl, C$_2$-C$_6$-alkenyl, C$_2$-C$_6$-alkynyl, arylalkyl, heteroarylalkyl, hydroxy, amino, aminoalkyl, hydroxyalkyl, C$_1$-C$_6$-alkoxy or R$_1$ and R$_2$ together can form a C$_3$-C$_7$-cycloalkyl ring, a carbonyl bond C=O or a carbon double bond;
P and Q are each independently selected and denote an aryl or heteroaryl group of formula

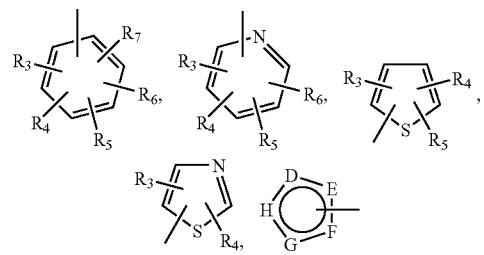

R$_3$, R$_4$, R$_5$, R$_6$, and R$_7$ independently are hydrogen, halogen, —CN, nitro, C$_1$-C$_6$-alkyl, C$_3$-C$_6$-cycloalkyl, C$_3$-C$_7$-cycloalkylalkyl, C$_2$-C$_6$-alkenyl, C$_2$-C$_6$-alkynyl, halo-C$_1$-C$_6$-alkyl, heteroaryl, heteroarylalkyl, arylalkyl, aryl, —OR$_8$, —NR$_8$R$_9$, —C(=NR$_{10}$)NR$_8$R$_9$, N(=NR$_{10}$)NR$_8$R$_9$, —NR$_8$COR$_9$, NR$_8$CO$_2$R$_9$, NR$_8$SO$_2$R$_9$, —NR$_{10}$CONR$_8$R$_9$, —SR$_8$, —S(=O)R$_8$, —S(=O)$_2$R$_8$, —S(=O)$_2$NR$_8$R$_9$, —C(=O)R$_8$, —C(=O)$_2$R$_8$, —C(=O)NR$_8$R$_9$, —C(=NR$_8$)R$_9$, or C(=NOR$_8$)R$_9$ substituents; wherein optionally two substituents are combined to the intervening atoms to form a bicyclic aryl or heteroaryl ring; wherein each ring is optionally further substituted with 1-5 independent halogen, —CN, C$_1$-C$_6$-alkyl, —O(C$_0$-C$_6$-alkyl), —O(C$_3$-C$_7$-cycloalkylalkyl), —O(aryl), —O(heteroaryl), —O(C$_1$-C$_3$-alkylaryl), —O(C$_1$-C$_3$-alkylheteroaryl), —N(C$_0$-C$_6$-alkyl)(C$_0$-C$_3$-alkylaryl) or —N(C$_0$-C$_6$-alkyl)(C$_0$-C$_3$-alkylheteroaryl) groups;
R$_8$, R$_9$, R$_{10}$ each independently is hydrogen, C$_1$-C$_6$-alkyl, C$_3$-C$_6$-cycloalkyl, C$_3$-C$_7$-cycloalkylalkyl, C$_2$-C$_6$-alkenyl, C$_2$-C$_6$-alkynyl, halo-C$_1$-C$_6$-alkyl, heteroaryl, heteroarylalkyl, arylalkyl or aryl; any of which is optionally substituted with 1-5 independent halogen, —CN, C$_1$-C$_6$-alkyl, —O(C$_0$-C$_6$-alkyl), —O(C$_3$-C$_7$-cycloalkylalkyl), —O(aryl), —O(heteroaryl), —N(C$_0$-C$_6$-alkyl)(C$_0$-C$_6$-alkyl), —N(C$_0$-C$_6$-alkyl)(C$_3$-C$_7$-cycloalkyl) or —N(C$_0$-C$_6$-alkyl)(aryl) substituents;
D, E, F, G and H in P & Q represent independently —C(R$_3$)=, —C(R$_3$)=C(R$_4$)—, —C(=O)—, —C(=S)—, —O—, —N=, —N(R$_3$)— or —S—;
D, E and G in A are independently as defined previously in A;
B represents a single bond, —C(=O)—C$_0$-C$_2$-alkyl-, —C(=O)—C$_2$-C$_6$-alkenyl-, —C(=O)—C$_2$-C$_6$-alkynyl-, —C(=O)—O—, —C(=O)NR$_8$—C$_0$-C$_2$-alkyl-, —C(=NR$_8$)NR$_9$—S(=O)—C$_0$-C$_2$-alkyl-, —S(=O)$_2$—C$_0$-C$_2$-alkyl-, —S(=O)$_2$NR$_8$—C$_0$-C$_2$-alkyl-, C(=NR$_8$)—C$_0$-C$_2$-alkyl-, —C(=NOR$_8$)—C$_0$-C$_2$-alkyl- or —C(=NOR$_8$)NR$_9$—C$_0$-C$_2$-alkyl-;
R$_8$ and R$_9$, independently are as defined above;
J represents —C(R$_{11}$, R$_{12}$), —O—, —N(R$_{11}$)— or —S—;
R$_{11}$, R$_{12}$ independently are hydrogen, C$_1$-C$_6$-alkyl, C$_3$-C$_6$-cycloalkyl, C$_3$-C$_7$-cycloalkylalkyl, C$_2$-C$_6$-alkenyl, C$_2$-C$_6$-alkynyl, halo-C$_1$-C$_6$-alkyl, heteroaryl, heteroarylalkyl, arylalkyl or aryl; any of which is optionally substituted with 1-5 independent halogen, —CN, C$_1$-C$_6$-alkyl, —O(C$_0$-C$_6$-alkyl), —O(C$_3$-C$_7$-cycloalkylalkyl), —O(aryl), —O(heteroaryl), —N(C$_0$-C$_6$-alkyl)(C$_0$-C$_6$-alkyl), —N(C$_0$-C$_6$-alkyl)(C$_3$-C$_7$-cycloalkyl) or —N(C$_0$-C$_6$-alkyl)(aryl) substituents;
Any N may be an N-oxide;

The present invention includes both possible stereoisomers and includes not only racemic compounds but the individual enantiomers as well.

An embodiment of the present invention includes compounds of the formula I-I

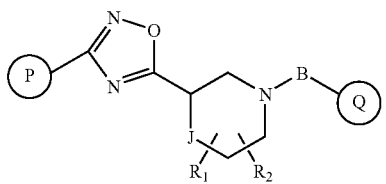

I-I

Wherein $R_1$ and $R_2$ represent independently hydrogen, $C_1$-$C_6$-alkyl, $C_2$-$C_6$-alkenyl, $C_2$-$C_6$-alkynyl, arylalkyl, heteroarylalkyl, hydroxy, hydroxyalkyl, $C_1$-$C_6$-alkoxy or $R_1$ and $R_2$ together can form a carbonyl bond C═O or a carbon double bond;

P and Q are each independently selected and denote an aryl or heteroaryl group of formula

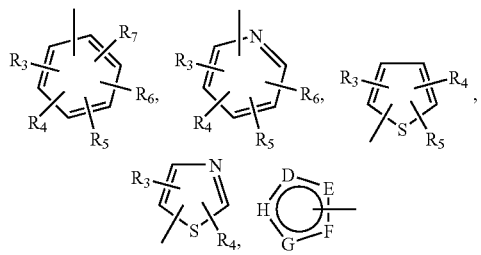

$R_3$, $R_4$, $R_5$, $R_6$, and $R_7$ independently are hydrogen, halogen, —CN, nitro, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, heteroaryl, heteroarylalkyl, arylalkyl, aryl, —$OR_8$, —$NR_8R_9$, —C(═$NR_{10}$)$NR_8R_9$, N(═$NR_{10}$)$NR_8R_9$, —$NR_8COR_9$, $NR_8CO_2R_9$, $NR_8SO_2R_9$, —$NR_{10}CO NR_8R_9$, —$SR_8$, —S(═O)$R_8$, —S(═O)$_2R_8$, —S(═O)$_2 NR_8R_9$, —C(═O)$R_8$, —C(═O)$_2R_8$, —C(═O)$NR_8R_9$, —C(═$NR_8$)$R_9$, or C(═$NOR_8$)$R_9$ substituents; wherein optionally two substituents are combined to the intervening atoms to form a bicyclic aryl or heteroaryl ring; wherein each ring is optionally further substituted with 1-5 independent halogen, —CN, $C_1$-$C_6$-alkyl, —O($C_0$-$C_6$-alkyl), —O($C_3$-$C_7$-cycloalkylalkyl), —O(aryl), —O(heteroaryl), —O($C_1$-$C_3$-alkylaryl), —O($C_1$-$C_3$-alkylheteroaryl), —N($C_0$-$C_6$-alkyl)($C_0$-$C_3$-alkylaryl) or —N($C_0$-$C_6$-alkyl)($C_0$-$C_3$-alkylheteroaryl) groups;

$R_8$, $R_9$, $R_{10}$ each independently is hydrogen, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, heteroaryl, heteroarylalkyl, arylalkyl or aryl; any of which is optionally substituted with 1-5 independent halogen, —CN, $C_1$-$C_6$-alkyl, —O($C_0$-$C_6$-alkyl), —O($C_3$-$C_7$-cycloalkylalkyl), —O(aryl), —O(heteroaryl), —N($C_0$-$C_6$-alkyl)($C_0$-$C_6$-alkyl), —N($C_0$-$C_6$-alkyl)($C_3$-$C_7$-cycloalkyl) or —N($C_0$-$C_6$-alkyl)(aryl) substituents;

D, E, F, G and H represent independently —C($R_3$)═, —C($R_3$)═C($R_4$)—, —C(═O)—, —C(═S)—, —O—, —N═, —N($R_3$)— or —S—;

B represents a single bond, —C(═O)—$C_0$-$C_2$-alkyl-, —C(═O)—$C_2$-$C_6$-alkenyl-, —C(═O)—$C_2$-$C_6$-alkynyl-, —C(═O)—O—, —C(═O)$NR_8$—$C_0$-$C_2$-alkyl-, —C(═$NR_8$)$NR_9$—S(═O)—$C_0$-$C_2$-alkyl-, —S(═O)$_2$—$C_0$-$C_2$-alkyl-, —S(═O)$_2NR_8$—$C_0$-$C_2$-alkyl-, C(═$NR_8$)—$C_0$-$C_2$-alkyl-, —C(═$NOR_8$)—$C_0$-$C_2$-alkyl- or —C(═$NOR_8$)$NR_9$—$C_0$-$C_2$-alkyl-;—

$R_8$ and $R_9$, independently are as defined above;

J represents —C($R_{11}$, $R_{12}$)$_2$)—, —O—, —N($R_{11}$)— or —S—;

$R_{11}$, $R_{12}$ independently are hydrogen, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, heteroaryl, heteroarylalkyl, arylalkyl or aryl; any of which is optionally substituted with 1-5 independent halogen, —CN, $C_1$-$C_6$-alkyl, —O($C_0$-$C_6$-alkyl), —O($C_3$-$C_7$-cycloalkylalkyl), —O(aryl), —O(heteroaryl), —N($C_0$-$C_6$-alkyl)($C_0$-$C_6$-alkyl), —N($C_0$-$C_6$-alkyl)($C_3$-$C_7$-cycloalkyl) or —N($C_0$-$C_6$-alkyl)(aryl) substituents;

Any N may be an N-oxide;

The present invention includes both possible stereoisomers and includes not only racemic compounds but the individual enantiomers as well.

An embodiment of the present invention includes compounds of the formula I-J

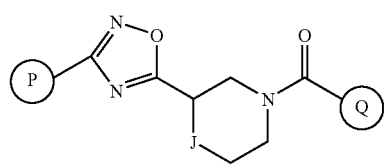

I-J

Wherein

P and Q are each independently selected and denote an aryl or heteroaryl group of formula

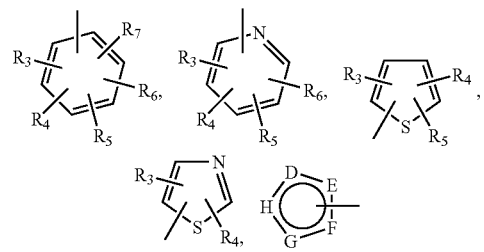

$R_3$, $R_4$, $R_5$, $R_6$, and $R_7$ independently are hydrogen, halogen, —CN, nitro, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, heteroaryl, heteroarylalkyl, arylalkyl, aryl, —$OR_8$, —$NR_8R_9$, —C(═$NR_{10}$)$NR_8R_9$, N(═$NR_{10}$)$NR_8R_9$, —$NR_8COR_9$, $NR_8CO_2R_9$, $NR_8SO_2R_9$, —$NR_{10}CO NR_8R_9$, —$SR_8$, —S(═O)$R_8$, —S(═O)$_2R_8$, —S(═O)$_2 NR_8R_9$, —C(═O)$R_8$, —C(═O)$_2R_8$, —C(═O)$NR_8R_9$, —C(═$NR_8$)$R_9$, or C(═$NOR_8$)$R_9$ substituents; wherein optionally two substituents are combined to the intervening atoms to form a bicyclic aryl or heteroaryl ring; wherein each ring is optionally further substituted with 1-5 independent halogen, —CN, $C_1$-$C_6$-alkyl, —O($C_0$-$C_6$-alkyl), —O($C_3$-$C_7$-cycloalkylalkyl), —O(aryl), —O(heteroaryl), —O($C_1$-$C_3$-alkylaryl), —O($C_1$-$C_3$-alkylheteroaryl), —N($C_0$-$C_6$-alkyl)($C_0$-$C_3$-alkylaryl) or —N($C_0$-$C_6$-alkyl)($C_0$-$C_3$-alkylheteroaryl) groups;

$R_8$, $R_9$, $R_{10}$ each independently is hydrogen, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, heteroaryl, heteroarylalkyl, arylalkyl or aryl; any of which is optionally substituted with 1-5 independent halogen, —CN, $C_1$-$C_6$-alkyl, —O($C_0$-$C_6$-alkyl), —O($C_3$-$C_7$-cycloalkylalkyl), —O(aryl), —O(heteroaryl), —N($C_0$-$C_6$-alkyl)($C_0$-$C_6$-alkyl), —N($C_0$-$C_6$-alkyl)($C_3$-$C_7$-cycloalkyl) or —N($C_0$-$C_6$-alkyl)(aryl) substituents;

D, E, F, G and H represent independently —C($R_3$)=, —C($R_3$)=C($R_4$)—, —C(=O)—, —C(=S)—, —O—, —N=, —N($R_3$)— or —S—;

J represents —C($R_{11}$, $R_{12}$), —O—, —N($R_{11}$)— or —S—;

$R_{11}$, $R_{12}$ independently are hydrogen, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, heteroaryl, heteroarylalkyl, arylalkyl or aryl; any of which is optionally substituted with 1-5 independent halogen, —CN, $C_1$-$C_6$-alkyl, —O($C_0$-$C_6$-alkyl), —O($C_3$-$C_7$-cycloalkylalkyl), —O(aryl), —O(heteroaryl), —N($C_0$-$C_6$-alkyl)($C_0$-$C_6$-alkyl), —N($C_0$-$C_6$-alkyl)($C_3$-$C_7$-cycloalkyl) or —N($C_0$-$C_6$-alkyl)(aryl) substituents;

Any N may be an N-oxide;

The present invention includes both possible stereoisomers and includes not only racemic compounds but the individual enantiomers as well.

An embodiment of the present invention includes compounds of the formula I-K

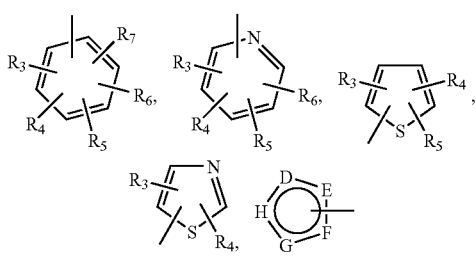

I-K

Wherein

P and Q are each independently selected and denote an aryl or heteroaryl group of formula

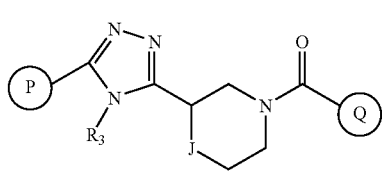

$R_3$, $R_4$, $R_5$, $R_6$, and $R_7$ independently are hydrogen, halogen, —CN, nitro, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, heteroaryl, heteroarylalkyl, arylalkyl, aryl, —O$R_8$, —N$R_8R_9$, —C(=N$R_{10}$)N$R_8R_9$, N(=N$R_{10}$)N$R_8R_9$, —N$R_8$CO$R_9$, N$R_8$CO$_2R_9$, N$R_8$SO$_2R_9$, —N$R_{10}$CO N$R_8R_9$, —S$R_8$, —S(=O)$R_8$, —S(=O)$_2R_8$, —S(=O)$_2$ N$R_8R_9$, —C(=O)$R_8$, —C(=O)$_2R_8$, —C(=O)N$R_8R_9$, —C(=N$R_8$)$R_9$, or C(=NO$R_8$)$R_9$ substituents; wherein optionally two substituents are combined to the intervening atoms to form a bicyclic aryl or heteroaryl ring; wherein each ring is optionally further substituted with 1-5 independent halogen, —CN, $C_1$-$C_6$-alkyl, —O($C_0$-$C_6$-alkyl), —O($C_3$-$C_7$-cycloalkylalkyl), —O(aryl), —O(heteroaryl), —O($C_1$-$C_3$-alkylaryl), —O($C_1$-$C_3$-alkylheteroaryl), —N($C_0$-$C_6$-alkyl)($C_0$-$C_3$-alkylaryl) or —N($C_0$-$C_6$-alkyl)($C_0$-$C_3$-alkylheteroaryl) groups;

$R_8$, $R_9$, $R_{10}$ each independently is hydrogen, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, heteroaryl, heteroarylalkyl, arylalkyl or aryl; any of which is optionally substituted with 1-5 independent halogen, —CN, $C_1$-$C_6$-alkyl, —O($C_0$-$C_6$-alkyl), —O($C_3$-$C_7$-cycloalkylalkyl), —O(aryl), —O(heteroaryl), —N($C_0$-$C_6$-alkyl)($C_0$-$C_6$-alkyl), —N($C_0$-$C_6$-alkyl)($C_3$-$C_7$-cycloalkyl) or —N($C_0$-$C_6$-alkyl)(aryl) substituents;

D, E, F, G and H represent independently —C($R_3$)=, —C($R_3$)=C($R_4$)—, —C(=O)—, —C(=S)—, —O—, —N=, —N($R_3$)— or —S—;

J represents —C($R_{11}$, $R_{12}$), —O—, —N($R_{11}$)— or —S—;

$R_{11}$, $R_{12}$ independently are hydrogen, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, heteroaryl, heteroarylalkyl, arylalkyl or aryl; any of which is optionally substituted with 1-5 independent halogen, —CN, $C_1$-$C_6$-alkyl, —O($C_0$-$C_6$-alkyl), —O($C_3$-$C_7$-cycloalkylalkyl), —O(aryl), —O(heteroaryl), —N($C_0$-$C_6$-alkyl)($C_0$-$C_6$-alkyl), —N($C_0$-$C_6$-alkyl)($C_3$-$C_7$-cycloalkyl) or —N($C_0$-$C_6$-alkyl)(aryl) substituents;

Any N may be an N-oxide;

The present invention includes both possible stereoisomers and includes not only racemic compounds but the individual enantiomers as well.

An embodiment of the present invention includes compounds of the formula I-L

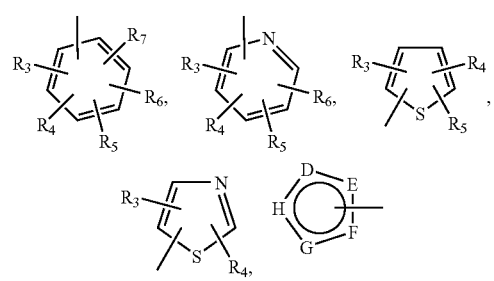

I-L

Wherein

P and Q are each independently selected and denote an aryl or heteroaryl group of formula $R_3$, $R_4$, $R_5$, $R_6$, and $R_7$ independently are hydrogen, halogen, —CN, nitro, $C_1$-$C_6$-alkyl, $C_3$-$C_6$-cycloalkyl, $C_3$-$C_7$-cycloalkylalkyl, $C_2$-$C_6$-alkenyl, $C_2$-$C_6$-alkynyl, halo-$C_1$-$C_6$-alkyl, heteroaryl, heteroarylalkyl, arylalkyl, aryl, —O$R_8$, —N$R_8R_9$, —C(=N$R_{10}$)N$R_8R_9$, N(=N$R_{10}$)N$R_8R_9$, —N$R_8$CO$R_9$, N$R_8$CO$_2R_9$, N$R_8$SO$_2R_9$, —N$R_{10}$CO N$R_8R_9$, —S$R_8$, —S(=O)$R_8$, —S(=O)$_2R_8$, —S (=O)$_2$NR$_8$R$_9$, —C(=O)R$_8$, —C(=O)$_2$R$_8$, —C(=O)NR$_8$R$_9$, —C(=NR$_8$)R$_9$, or C(=NOR$_8$)R$_9$ substituents; wherein optionally two substituents are combined to the intervening atoms to form a bicyclic aryl or heteroaryl ring; wherein each ring is optionally further substituted with 1-5 independent halogen, —CN, C$_1$-C$_6$-alkyl, —O(C$_0$-C$_6$-alkyl), —O(C$_3$-C$_7$-cycloalkylalkyl), —O(aryl), —O(heteroaryl), —O(C$_1$-C$_3$-alkylaryl), —O(C$_1$-C$_3$-alkylheteroaryl), —N(C$_0$-C$_6$-alkyl)(C$_0$-C$_3$-alkylaryl) or —N(C$_0$-C$_6$-alkyl)(C$_0$-C$_3$-alkylheteroaryl) groups;

R$_8$, R$_9$, R$_{10}$ each independently is hydrogen, C$_1$-C$_6$-alkyl, C$_3$-C$_6$-cycloalkyl, C$_3$-C$_7$-cycloalkylalkyl, C$_2$-C$_6$-alkenyl, C$_2$-C$_6$-alkynyl, halo-C$_1$-C$_6$-alkyl, heteroaryl, heteroarylalkyl, arylalkyl or aryl; any of which is optionally substituted with 1-5 independent halogen, —CN, C$_1$-C$_6$-alkyl, —O(C$_0$-C$_6$-alkyl), —O(C$_3$-C$_7$-cycloalkylalkyl), —O(aryl), —O(heteroaryl), —N(C$_0$-C$_6$-alkyl)(C$_0$-C$_6$-alkyl), —N(C$_0$-C$_6$-alkyl)(C$_3$-C$_7$-cycloalkyl) or —N(C$_0$-C$_6$-alkyl)(aryl) substituents;

D, E, F, G and H represent independently —C(R$_3$)=, —C(R$_3$)=C(R$_4$)—, —C(=O)—, —C(=S)—, —O—, —N=, —N(R$_3$)— or —S—;

J represents —C(R$_{11}$, R$_{12}$), —O—, —N(R$_{11}$)— or —S—;

R$_{11}$, R$_{12}$ independently are hydrogen, C$_1$-C$_6$-alkyl, C$_3$-C$_6$-cycloalkyl, C$_3$-C$_7$-cycloalkylalkyl, C$_2$-C$_6$-alkenyl, C$_2$-C$_6$-alkynyl, halo-C$_1$-C$_6$-alkyl, heteroaryl, heteroarylalkyl, arylalkyl or aryl; any of which is optionally substituted with 1-5 independent halogen, —CN, C$_1$-C$_6$-alkyl, —O(C$_0$-C$_6$-alkyl), —O(C$_3$-C$_7$-cycloalkylalkyl), —O(aryl), —O(heteroaryl), —N(C$_0$-C$_6$-alkyl)(C$_0$-C$_6$-alkyl), —N(C$_0$-C$_6$-alkyl)(C$_3$-C$_7$-cycloalkyl) or —N(C$_0$-C$_6$-alkyl)(aryl) substituents;

Any N may be an N-oxide;

The present invention includes both possible stereoisomers and includes not only racemic compounds but the individual enantiomers as well.

An embodiment of the present invention includes compounds of the formula I-M

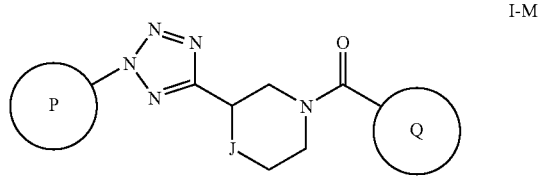

I-M

Wherein

P and Q are each independently selected and denote an aryl or heteroaryl group of formula

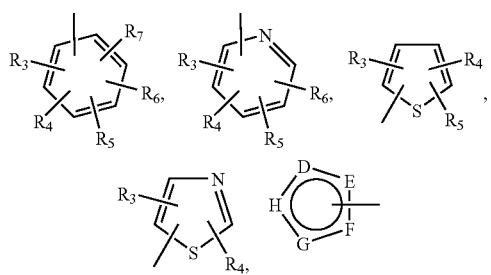

R$_3$, R$_4$, R$_5$, R$_6$, and R$_7$ independently are hydrogen, halogen, —CN, nitro, C$_1$-C$_6$-alkyl, C$_3$-C$_6$-cycloalkyl, C$_3$-C$_7$-cycloalkylalkyl, C$_2$-C$_6$-alkenyl, C$_2$-C$_6$-alkynyl, halo-C$_1$-C$_6$-alkyl, heteroaryl, heteroarylalkyl, arylalkyl, aryl, —OR$_8$, —NR$_8$R$_9$, —C(=NR$_{10}$)NR$_8$R$_9$, N(=NR$_{10}$)NR$_8$R$_9$, —NR$_8$COR$_9$, NR$_8$CO$_2$R$_9$, NR$_8$SO$_2$R$_9$, —NR$_{10}$CONR$_8$R$_9$, —SR$_8$, —S(=O)R$_8$, —S(=O)$_2$R$_8$, —S(=O)$_2$NR$_8$R$_9$, —C(=O)R$_8$, —C(=O)$_2$R$_8$, —C(=O)NR$_8$R$_9$, —C(=NR$_8$)R$_9$, or C(=NOR$_8$)R$_9$ substituents; wherein optionally two substituents are combined to the intervening atoms to form a bicyclic aryl or heteroaryl ring; wherein each ring is optionally further substituted with 1-5 independent halogen, —CN, C$_1$-C$_6$-alkyl, —O(C$_0$-C$_6$-alkyl), —O(C$_3$-C$_7$-cycloalkylalkyl), —O(aryl), —O(heteroaryl), —O(C$_1$-C$_3$-alkylaryl), —O(C$_1$-C$_3$-alkylheteroaryl), —N(C$_0$-C$_6$-alkyl)(C$_0$-C$_3$-alkylaryl) or —N(C$_0$-C$_6$-alkyl)(C$_0$-C$_3$-alkylheteroaryl) groups;

R$_8$, R$_9$, R$_{10}$ each independently is hydrogen, C$_1$-C$_6$-alkyl, C$_3$-C$_6$-cycloalkyl, C$_3$-C$_7$-cycloalkylalkyl, C$_2$-C$_6$-alkenyl, C$_2$-C$_6$-alkynyl, halo-C$_1$-C$_6$-alkyl, heteroaryl, heteroarylalkyl, arylalkyl or aryl; any of which is optionally substituted with 1-5 independent halogen, —CN, C$_1$-C$_6$-alkyl, —O(C$_0$-C$_6$-alkyl), —O(C$_3$-C$_7$-cycloalkylalkyl), —O(aryl), —O(heteroaryl), —N(C$_0$-C$_6$-alkyl)(C$_0$-C$_6$-alkyl), —N(C$_0$-C$_6$-alkyl)(C$_3$-C$_7$-cycloalkyl) or —N(C$_0$-C$_6$-alkyl)(aryl) substituents;

D, E, F, G and H represent independently —C(R$_3$)=, —C(R$_3$)=C(R$_4$)—, —C(=O)—, —C(=S)—, —O—, —N=, —N(R$_3$)— or —S—;

J represents —C(R$_{11}$, R$_{12}$), —O—, —N(R$_{11}$)— or —S—;

R$_{11}$, R$_{12}$ independently are hydrogen, C$_1$-C$_6$-alkyl, C$_3$-C$_6$-cycloalkyl, C$_3$-C$_7$-cycloalkylalkyl, C$_2$-C$_6$-alkenyl, C$_2$-C$_6$-alkynyl, halo-C$_1$-C$_6$-alkyl, heteroaryl heteroarylalkyl, arylalkyl or aryl; any of which is optionally substituted with 1-5 independent halogen, —CN, C$_1$-C$_6$-alkyl, —O(C$_0$-C$_6$-alkyl), —O(C$_3$-C$_7$-cycloalkylalkyl), —O(aryl), —O(heteroaryl), —N(C$_0$-C$_6$-alkyl)(C$_0$-C$_6$-alkyl), —N(C$_0$-C$_6$-alkyl)(C$_3$-C$_7$-cycloalkyl) or —N(C$_0$-C$_6$-alkyl)(aryl) substituents;

Any N may be an N-oxide;

The present invention includes both possible stereoisomers and includes not only racemic compounds but the individual enantiomers as well.

An embodiment of the present invention includes compounds of te formula I-N

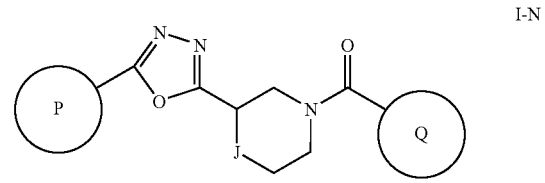

I-N

Wherein

P and Q are each independently selected and denote an aryl or heteroaryl group of formula

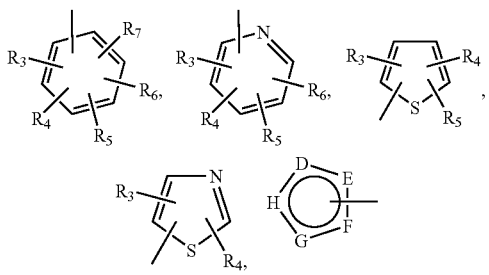

R$_3$, R$_4$, R$_5$, R$_6$, and R$_7$ independently are hydrogen, halogen, —CN, nitro, C$_1$-C$_6$-alkyl, C$_3$-C$_6$-cycloalkyl, C$_3$-C$_7$-cycloalkylalkyl, C$_2$-C$_6$-alkenyl, C$_2$-C$_6$-alkynyl, halo-C$_1$-C$_6$-alkyl, heteroaryl, heteroarylalkyl, arylalkyl, aryl, —OR$_8$, —NR$_8$R$_9$, —C(=NR$_{10}$)NR$_8$R$_9$, N(=NR$_{10}$)NR$_8$R$_9$, —NR$_8$COR$_9$, NR$_8$CO$_2$R$_9$, NR$_8$SO$_2$R$_9$, —NR$_{10}$CO NR$_8$R$_9$, —SR$_8$, —S(=O)R$_8$, —S(=O)$_2$R$_8$, —S(=O)$_2$ NR$_8$R$_9$, —C(=O)R$_8$, —C(=O)$_2$R$_8$, —C(=O)NR$_8$R$_9$, —C(=NR$_8$)R$_9$, or C(=NOR$_8$)R$_9$ substituents; wherein optionally two substituents are combined to the intervening atoms to form a bicyclic aryl or heteroaryl ring; wherein each ring is optionally further substituted with 1-5 independent halogen, —CN, C$_1$-C$_6$-alkyl, —O(C$_0$-C$_6$-alkyl), —O(C$_3$-C$_7$-cycloalkylalkyl), —O(aryl), —O(heteroaryl), —O(C$_1$-C$_3$-alkylaryl), —O(C$_1$-C$_3$-alkylheteroaryl), —N(C$_0$-C$_6$-alkyl)(C$_0$-C$_3$-alkylaryl) or —N(C$_0$-C$_6$-alkyl)(C$_0$-C$_3$-alkylheteroaryl) groups;

R$_8$, R$_9$, R$_{10}$ each independently is hydrogen, C$_1$-C$_6$-alkyl, C$_3$-C$_6$-cycloalkyl, C$_3$-C$_7$-cycloalkylalkyl, C$_2$-C$_6$-alkenyl, C$_2$-C$_6$-alkynyl, halo-C$_1$-C$_6$-alkyl, heteroaryl, heteroarylalkyl, arylalkyl or aryl; any of which is optionally substituted with 1-5 independent halogen, —CN, C$_1$-C$_6$-alkyl, —O(C$_0$-C$_6$-alkyl), —O(C$_3$-C$_7$-cycloalkylalkyl), —O(aryl), —O(heteroaryl), —N(C$_0$-C$_6$-alkyl) (C$_0$-C$_6$-alkyl), —N(C$_0$-C$_6$-alkyl)(C$_3$-C$_7$-cycloalkyl) or —N(C$_0$-C$_6$-alkyl)(aryl) substituents;

D, E, P, G and H represent independently —C(R$_3$)=, —C(R$_3$)=C(R$_4$)—, —C(=O)—, —C(=S)—, —O—, —N=, —N(R$_3$)— or —S—;

J represents —C(R$_{11}$, R$_{12}$), —O—, —N(R$_{11}$)— or —S—;

R$_{11}$, R$_{12}$ independently are hydrogen, C$_1$-C$_6$-alkyl, C$_3$-C$_6$-cycloalkyl, C$_3$-C$_7$-cycloalkylalkyl, C$_2$-C$_6$-alkenyl, C$_2$-C$_6$-alkynyl, halo-C$_1$-C$_6$-alkyl, heteroaryl, heteroarylalkyl, arylalkyl or aryl; any of which is optionally substituted with 1-5 independent halogen, —CN, C$_1$-C$_6$-alkyl, —O(C$_0$-C$_6$-alkyl), —O(C$_3$-C$_7$-cycloalkylalkyl), —O(aryl), —O(heteroaryl), —N(C$_0$-C$_6$-alkyl)(C$_0$-C$_6$-alkyl), —N(C$_0$-C$_6$-alkyl)(C$_3$-C$_7$-cycloalkyl) or —N(C$_0$-C$_6$-alkyl)(aryl) substituents;

Any N may be an N-oxide;

The present invention includes both possible stereoisomers and includes not only racemic compounds but the individual enantiomers as well.

Specifically preferred compounds are:
(4-Fluoro-phenyl)-[3-(4-fluoro-phenylethynyl)-piperidin-1-yl]-methanone
(4-Fluoro-phenyl)-{3-[5-(4-fluoro-phenyl)-4H-[1,2,4]triazol-3-yl]-piperidin-1-yl}-methanone
(S)-(4-Fluoro-phenyl)-{3-[3-(4-fluoro-phenyl)-[1,2,4]oxadiazol-5-yl]-piperidin-1-yl}-methanone
(S)-(thiophen-2-yl)-{3-[3-(4-fluoro-phenyl)-[1,2,4]oxadiazol-5-yl]-piperidin-1-yl}-methanone
{(S)-3-[3-(4-Fluoro-phenyl)-[1,2,4]oxadiazol-5-yl]-piperidin-1-yl}-(4-methyl-2-pyrazin-2-yl-thiazol-5-yl)-methanone
(2,4-Difluoro-phenyl)-{(S)-3-[3-(4-fluoro-phenyl)-[1,2,4]oxadiazol-5-yl]-piperidin-1-yl}-methanone
{(S)-3-[3-(4-Fluoro-phenyl)-[1,2,4]oxadiazol-5-yl]-piperidin-1-yl}-(3,4,5-trifluoro-phenyl)-methanone
{(S)-3-[3-(4-Fluoro-phenyl)-1,2,4-oxadiazol-5-yl]-piperidin-1-yl}-(5-pyridin-2-yl-thiophen-2-yl)-methanone
Cyclopentyl-{(S)-3-[3-(4-fluoro-phenyl)-[1,2,4]oxadiazol-5-yl]-piperidin-1-yl}-methanone
(3,4-Difluoro-phenyl)-{(S)-3-[3-(4-fluoro-phenyl)-[1,2,4]oxadiazol-5-yl]-piperidin-1-yl}-methanone
Benzothiazol-6-yl-{(S)-3-[3-(4-fluoro-phenyl)-1,2,4-oxadiazol-5-yl]-piperidin-1-yl}-methanone
(3,5-Dimethyl-isoxazol-4-yl)-{(S)-3-[3-(4-fluoro-phenyl)-[1,2,4]oxadiazol-5-yl]-piperidin-1-yl}-methanone
(4-Fluoro-phenyl)-{(S)-3-[3-(2,4,6-trifluoro-phenyl)-[1,2,4]oxadiazol-5-yl]-piperidin-1-yl}-methanone
(4-Fluoro-phenyl)-[(S)-3-(3-pyridin-3-yl-[1,2,4]oxadiazol-5-yl)-piperidin-1-yl]-methanone
(4-Fluoro-phenyl)-[(S)-3-(3-pyridin-4-yl-[1,2,4]oxadiazol-5-yl)-piperidin-1-yl]-methanone
{(S)-3-[3-(2,4-Difluoro-phenyl)-[1,2,4]oxadiazol-5-yl]-piperidin-1-yl}-(4-fluoro-phenyl)-methanone
(4-Fluoro-phenyl)-[(S)-3-(3-p-tolyl-[1,2,4]oxadiazol-5-yl)-piperidin-1-yl]-methanone
(4-Fluoro-phenyl)-{(S)-3-[3-(2-fluoro-phenyl)-[1,2,4]oxadiazol-5-yl]-piperidin-1-yl}-methanone
(4-Fluoro-phenyl)-[(S)-3-(3-pyridin-2-yl-[1,2,4]oxadiazol-5-yl)-piperidin-1-yl]-methanone
(4-Fluoro-phenyl)-{3-[5-(4-fluoro-phenyl)-[1,3,4]oxadiazol-2-yl]-piperidin-1-yl}-methanone
(2-Fluoro-phenyl)-{(S)-3-[2-(3,4-difluoro-phenyl)-1,2,4]oxadiazol-5-yl]-piperidin-1-yl}-methanone
(4-Fluoro-phenyl)-{2-[3-(4-fluoro-phenyl)-[1,2,4]oxadiazol-5-yl]-morpholin-4-yl}-methanone
{(S)-3-[3-(4-Fluoro-phenyl)-[1,2,4]oxadiazol-5-yl]-piperidin-1-yl}-thiophen-3-yl-methanone
(4-Fluoro-phenyl)-[3-(5-phenyl-tetrazol-2-yl)-piperidin-1-yl]-methanone
(4-Fluoro-phenyl)-[(S)-3-(3-phenyl-[1,2,4]oxadiazol-5-yl)-piperidin-1-yl]-methanone
(3,4-Difluoro-phenyl)-[(S)-3-(3-phenyl-[1,2,4]oxadiazol-5-yl)-piperidin-1-yl]-methanone
{3-[3-(4-Methoxy-phenyl)-[1,2,4]oxadiazol-5-yl]-piperidin-1-yl}-phenyl-methanone
{3-[3-(4-Fluoro-phenyl)-[1,2,4]oxadiazol-5-yl]-piperidin-1-yl}-phenyl-methanone
(4-Fluoro-phenyl)-[3-(3-phenyl-[1,2,4]oxadiazol-5-yl)-piperidin-1-yl]-methanone
(3-Fluoro-phenyl)-[3-(3-phenyl-[1,2,4]oxadiazol-5-yl)-piperidin-1-yl]-methanone
(4-Fluoro-phenyl)-{3-[3-(3-fluoro-phenyl)-[1,2,4]oxadiazol-5-yl]-piperidin-1-yl}-methanone
(3-Fluoro-phenyl)-{3-[3-(3-fluoro-phenyl)-[1,2,4]oxadiazol-5-yl]-piperidin-1-yl}-methanone
(4-Fluoro-phenyl)-{3-[3-(4-fluoro-phenyl)-[1,2,4]oxadiazol-5-yl]-piperidin-1-yl}-methanone
(3-Fluoro-phenyl)-{3-[3-(4-fluoro-phenyl)-[1,2,4]oxadiazol-5-yl]-piperidin-1-yl}-methanone
(R)-(4-Fluoro-phenyl)-{3-[3-(4-fluoro-phenyl)-[1,2,4]oxadiazol-5-yl]-piperidin-1-yl}-methanone
(4-Fluoro-phenyl)-{3-[5-(4-fluoro-phenyl)-[1,2,4]oxadiazol-3-yl]-piperidin-1-yl}-methanone
(4-Fluoro-phenyl)-{3-[5-(4-fluoro-phenyl)-4-methyl-4H-[1,2,4]triazol-3-yl]-piperidin 1-yl}-methanone {(S)-3-[3-(4-Fluoro-phenyl)-[1,2,4]oxadiazol-5-yl]-piperidin-1-l}-(2-phenyl-thiazol-4-yl)-methanone
{{(S)-3-[3-(4-Fluoro-phenyl)-[1,2,4]oxadiazol-5-yl]-piperidin-1-yl}-(2-methyl-6-trifluoromethyl-pyridin-3-yl)-methanone
{(S)-3-[3-(4-Fluoro-phenyl)-[1,2,4]oxadiazol-5-yl]-piperidin-1-yl}-[1,2,3]thiadiazol-4-yl-methanone
Benzothiazol-2-yl-{(S)-3-[3-(4-fluoro-phenyl)-[1,2,4]oxadiazol-5-yl]-piperidin-1-yl}-methanone
{(S)-3-[3-(4-Fluoro-phenyl)-[1,2,4]oxadiazol-5-yl]-piperidin-1-yl}-(5-methyl-isoxazol-3-yl)-methanone
(1,5-Dimethyl-1H-pyrazol-3-yl)-{(S)-3-[3-(4-fluoro-phenyl)-[1,2,4]oxadiazol-5-yl]-piperidin-1-yl}-methanone
{(S)-3-[3-(4-Fluoro-phenyl)-[1,2,4]oxadiazol-5-yl]-piperidin-1-yl}-(4-trifluoromethyl-phenyl)-methanone
4-{(S)-3-[3-(4-Fluoro-phenyl)-[1,2,4]oxadiazol-5-yl]-piperidine-1-carbonyl}-benzonitrile
{(S)-3-[3-(4-Fluoro-phenyl)-[1,2,4]oxadiazol-5-yl]-piperidin-1-yl}-isoxazol-5-yl-methanone
(3-Chloro-4-fluoro-phenyl)-{(S)-3-[3-(4-fluoro-phenyl)-[1,2,4]oxadiazol-5-yl]-piperidin-1-yl}-methanone
{(S)-3-[3-(4-Fluoro-phenyl)-[1,2,4]oxadiazol-5-yl]-piperidin-1-yl}-(2-phenyl-2H-pyrazol-3-yl)-methanone
{(S)-3-[3-(4-Fluoro-phenyl)-[1,2,4]oxadiazol-5-yl]-piperidin-1-yl}-(5-methyl-2-phenyl-2H-[1,2,3]triazol-4-yl)-methanone
(4-Fluoro-3-methyl-phenyl)-{(S)-3-[3-(4-fluoro-phenyl)-[1,2,4]oxadiazol-5-yl]-piperidin-1-yl}-methanone
{(S)-3-[3-(4-Fluoro-phenyl)-1,2,4-oxadiazol-5-yl]-piperidin-1-yl}-(3-methyl-thiophen-2-yl)-methanone
{(S)-3-[3-(4-Fluoro-phenyl)-1,2,4-oxadiazol-5-yl]-piperidin-1-yl}-(1-methyl-1H-pyrrol-2-yl)-methanone
{(S)-3-[3-(4-Fluoro-phenyl)-1,2,4-oxadiazol-5-yl]-piperidin-1-yl}-thiazol-2-yl-methanone
{(S)-3-[3-(4-Fluoro-phenyl)-1,2,4-oxadiazol-5-yl]-piperidin-1-yl}-(4-methyl-thiazol-5-yl)-methanone
{(S)-3-[3-(4-Fluoro-phenyl)-1,2,4-oxadiazol-5-yl]-piperidin-1-yl}-(6-morpholin-4-yl-pyridin-3-yl)-methanone
{(S)-3-[3-(4-Fluoro-phenyl)-1,2,4-oxadiazol-5-yl]-piperidin-1-yl}-(1H-indol-5-yl)-methanone
2-(4-Fluoro-phenyl)-1-{(S)-3-[3-(4-fluoro-phenyl)-1,2,4-oxadiazol-5-yl]-piperidin-1-yl}-ethanone
3-(4-Fluoro-phenyl)-1-{(S)-3-[3-(4-fluoro-phenyl)-1,2,4-oxadiazol-5-yl]-piperidin-1-yl}-propan-1-one
{(S)-3-[3-(4-Fluoro-phenyl)-1,2,4-oxadiazol-5-yl]-piperidin-1-yl}-isoquinolin-3-yl-methanone
{(S)-3-[3-(4-Fluoro-phenyl)-1,2,4-oxadiazol-5-yl]-piperidin-1-yl}-quinoxalin-6-yl-methanone
{(S)-3-[3-(4-Fluoro-phenyl)-1,2,4-oxadiazol-5-yl]-piperidin-1-yl}-benzoimidazol-6-yl-methanone
(4-Fluoro-phenyl)-[(S)-3-(3-naphthalen-1-yl-[1,2,4]oxadiazol-5-yl)-piperidin-1-yl]-methanone
{(S)-3-[3-(2,6-Difluoro-phenyl)-[1,2,4]oxadiazol-5-yl]-piperidin-1-yl}-(4-fluoro-phenyl)-methanone
(4-Fluoro-phenyl)-{(S)-3-[3-(2-methoxy-phenyl)-[1,2,4]oxadiazol-5-yl]-piperidin-1-yl}-methanone
(4-Fluoro-phenyl)-[(S)-3-(3-naphthalen-2-yl-[1,2,4]oxadiazol-5-yl)-piperidin-1-yl]-methanone
(4-Fluoro-phenyl)-{3-[5-(4-fluoro-phenyl)-[1,2,4]oxadiazol-3-yl]-piperidin-1-yl}-methanone
(4-Fluoro-phenyl)-{3-[3-(4-fluoro-phenyl)-[1,2,4]oxadiazol-5-yl]-4-methyl-piperazin-1-yl}-methanone
(S)-1-(4-Fluoro-benzoyl)-piperidine-3-carboxylic acid (4-fluoro-phenyl)-amide
(S)-1-(4-Fluoro-benzoyl)-piperidine-3-carboxylic acid (4-fluoro-phenyl)-methylamide.
(E)-3-(4-Fluoro-phenyl)-1-{(S)-3-[3-(4-fluoro-phenyl)-[1,2,4]oxadiazol-5-yl]-piperidin-1-yl}-propenone
1-(4-{(S)-3-[3-(4-Fluoro-phenyl)-[1,2,4]oxadiazol-5-yl]-piperidine-1-carbonyl}-piperidin-1-yl)-ethanone
{(S)-3-[3-(4-Fluoro-phenyl)-[1,2,4]oxadiazol-5-yl]-piperidin-1-yl}-(4-imidazol-1-yl-phenyl)-methanone
(4-Fluoro-phenyl)-{(S)-3-[3-(4-nitro-phenyl)-[1,2,4]oxadiazol-5-yl]-piperidin-1-yl}-methanone
(3,4-Difluoro-phenyl)-{(S)-3-[3-(4-nitro-phenyl)-[1,2,4]oxadiazol-5-yl]-piperidin-1-yl}-methanone.
Other illustrative compounds of formulas I are listed below:
(4-fluorophenyl)(3-(5-(4-fluorophenyl)isoxazol-3-yl)piperidin-1-yl)methanone
(4-fluorophenyl)(3-(5-(4-fluorophenyl)-1H-imidazol-2-yl)piperidin-1-yl)methanone
(4-fluorophenyl)(3-(4-(4-fluorophenyl)-1H-imidazol-1-yl)piperidin-1-yl)methanone
(4-fluorophenyl)(3-(4-(4-fluorophenyl)-1H-pyrazol-1-yl)piperidin-1-yl)methanone
N-(1-(4-fluorobenzoyl)piperidin-3-yl)-4-fluorobenzamid
(2-Fluoro-phenyl)-{3-[2-(4-fluoro-phenyl)-oxazol-5-yl]-piperidin-1-yl}-methanone
(2-Fluoro-phenyl)-{3-[5-(4-fluoro-phenyl)-oxazol-2-yl]-piperidin-1-yl}-methanone
(2-Fluoro-phenyl)-{3-[5-(4-fluoro-phenyl)-thiazol-2-yl]-piperidin-1-yl}-methanone
(2-Fluoro-phenyl)-{3-[2-(4-fluoro-phenyl)-thiazol-5-yl]-piperidin-1-yl}-methanone
(2-Fluoro-phenyl)-{3-[5-(4-fluoro-phenyl)-[1,3,4]thiadiazol-2-yl]-piperidin-1-yl}-methanone
(2-Fluoro-phenyl)-{3-[5-(4-fluoro-phenyl)-[1,2,4]oxadiazol-3-yl]-piperidin-1-yl}-methanone
(2-fluorophenyl)(3-(5-(4-fluorophenyl)isoxazol-3-yl)piperidin-1-yl)methanone
(2-fluorophenyl)(3-(5-(4-fluorophenyl)-1H-imidazol-2-yl)piperidin-1-yl)methanone
(2-fluorophenyl)(3-(4-(4-fluorophenyl)-1H-imidazol-1-yl)piperidin-1-yl)methanone
(2-fluorophenyl)(3-(4-(4-fluorophenyl)-1H-pyrazol-1-yl)piperidin-1-yl)methanone
N-(1-(4-fluorobenzoyl)piperidin-3-yl)-2-fluorobenzamid
(2-Fluoro-phenyl)-{3-[2-(3,4-fluoro-phenyl)-oxazol-5-yl]-piperidin-1-yl}-methanone
(2-Fluoro-phenyl)-{3-[5-(3,4-fluoro-phenyl)-oxazol-2-yl]-piperidin-1-yl}-methanone
(2-Fluoro-phenyl)-{3-[5-(3,4-fluoro-phenyl)-thiazol-2-yl]-piperidin-1-yl}-methanone
(2-Fluoro-phenyl)-{3-[2-(3,4-fluoro-phenyl)-thiazol-5-yl]-piperidin-1-yl}-methanone
(2-Fluoro-phenyl)-{3-[5-(3,4-fluoro-phenyl)-[1,3,4]thiadiazol-2-yl]-piperidin-1-yl}-methanone
(2-Fluoro-phenyl)-{3-[5-(3,4-fluoro-phenyl)-[1,2,4]oxadiazol-3-yl]-piperidin-1-yl}-methanone
(2-fluorophenyl)(3-(5-(3,4-fluorophenyl)isoxazol-3-yl)piperidin-1-yl)methanone
(2-fluorophenyl)(3-(5-(3,4-fluorophenyl)-1H-imidazol-2-yl)piperidin-1-yl)methanone
(2-fluorophenyl)(3-(4-(3,4-fluorophenyl)-1H-imidazol-1-yl)piperidin-1-yl)methanone
(2-fluorophenyl)(3-(4-(3,4-fluorophenyl)-1H-pyrazol-1-yl)piperidin-1-yl)methanone
N-(1-(3,4-fluorobenzoyl)piperidin-3-yl)-2-fluorobenzamid.
The present invention relates to the pharmaceutically acceptable acid addition salts of compounds of the formula (I) or pharmaceutically acceptable carriers or excipients.

The present invention relates to a method of treating or preventing a condition in a mammal, including a human, the treatment or prevention of which is affected or facilitated by the neuromodulatory effect of mGLUR5 allosteric modulators and particularly positive allosteric modulators.

The present invention relates to a method useful for treating or preventing peripheral and central nervous system disorders selected from the group consisting of: tolerance or dependence, anxiety, depression, psychiatric disease such as psychosis, inflammatory or neuropathic pain, memory impairment, Alzheimer's disease, ischemia, drug abuse and addiction.

The present invention relates to pharmaceutical compositions which provide from about 0.01 to 1000 mg of the active ingredient per unit dose. The compositions may be administered by any suitable route. For example orally in the form of capsules, etc. . . . , parenterally in the form of solutions for injection, topically in the form of onguents or lotions, ocularly in the form of eye-lotion, rectally in the form of suppositories.

The pharmaceutical formulations of the invention may be prepared by conventional methods in the art; the nature of the pharmaceutical composition employed will depend on the desired route of administration. The total daily dose usually ranges from about 0.05-2000 mg.

Methods of Synthesis

Compounds of general formula I may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley et Sons). These groups are removed at a convenient stage of the compound synthesis using methods that are readily apparent to those skilled in the art. The selection of process as well as the reaction conditions and order of their execution shall be consistent with the preparation of compounds of formula I.

The compound of formula I may be represented as a mixture of enantiomers, which may be resolved into the individual pure R- or S-enantiomers. If for instance, a particular enantiomer of the compound of formula I is desired, it may be prepared by asymmetric synthesis, or by derivation with a chiral auxiliary, where the resulting diastereomeric mixture is separated and the auxiliary group cleaved to provided the pure desired enantiomers. Alternatively, where the molecule contains a basic functional group such as amino, or an acidic functional group such as carboxyl, this resolution may be conveniently performed by fractional crystallization from various solvents, of the salts of the compounds of formula I with optical active acid or by other methods known in the literature, e.g. chiral column chromatography. Resolution of the final product, an intermediate or a starting material may be performed by any suitable method known in the art as described by E. L. Eliel, S. H. Wilen and L. N. Mander (1984) *Stereochemistry of Organic Compounds*, Wiley-Interscience.

Many of the heterocyclic compounds of formula I where A is an heteroaromatic group can be prepared using synthetic routes well known in the art (A. R. Katrizky A. R. and C. W. Rees (1984) *Comprehensive Heterocyclic Chemistry*, Pergamon Press).

The product from the reaction can be isolated and purified employing standard techniques, such as extraction, chromatography, crystallization, distillation, and the like.

The compounds of formula I-A in the case with A is a triazole group of formula

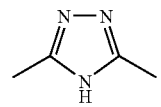

and W is a 3-substituted piperidine ring may be prepared according to the synthetic sequences illustrated in the Schemes 1-3.

Wherein

P and Q each independently is aryl or heteroaryl as described above B represents —C(=O)—$C_0$-$C_2$-alkyl-; —S(=O)2-$C_0$-$C_2$-alkyl-.

Scheme 1

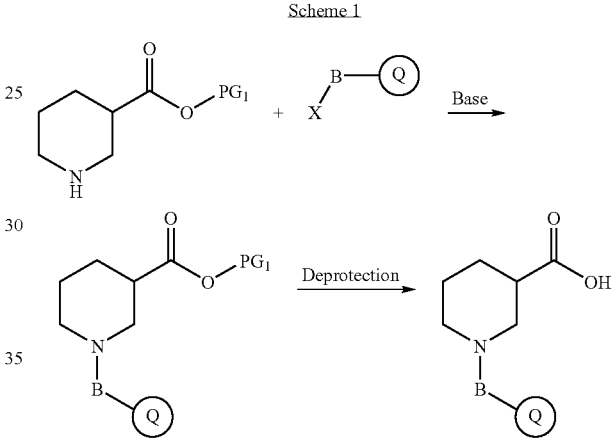

In the Scheme 1, a nipecotic acid precursor (for example ethyl nipecotate) is reacted with an aryl or heteroaryl derivatives, for example 4-Fluoro-benzoyl chloride using method that are readily apparent to those skilled in the art. In the Scheme 1, B is as defined above, X is halogen, $PG_1$ is a protecting group such as benzyl, tert-butyl, ethyl, allyl and the like. The reaction may be promoted by a base such as triethylamine, diisopropylamine, pyridine in a suitable solvent (e.g. tetrahydrofuran, dichloromethane) The reaction typically proceeds by allowing the reaction temperature to warm slowly from 0° C. up to ambient temperature for a time in the range of about 4 up to 12 hours. Protecting groups $PG_1$ are removed using conventional methods.

Scheme 2

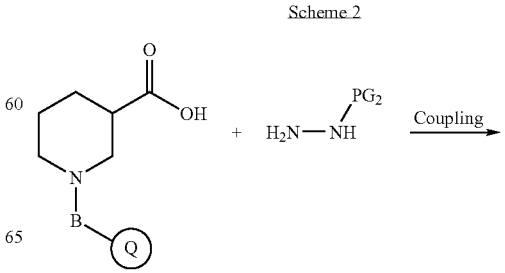

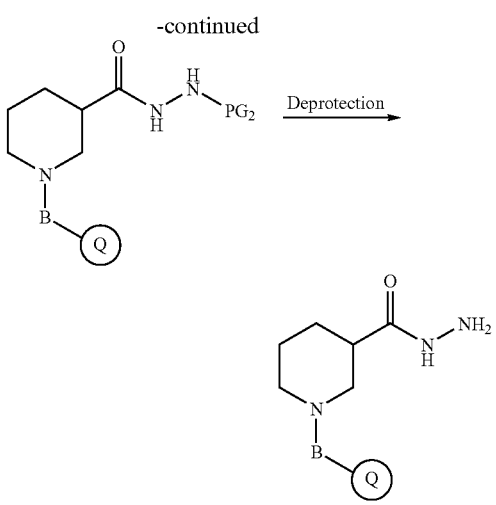

In turn, the substituted acid derivative (described in the Scheme 1) may be converted to a hydrazide derivative using the approach outlined in the Scheme 2. In the Scheme 2, PG$_2$ is an amino protecting group such as tert-Butyloxycarbonyl, Benzyloxycarbonyl, Ethoxycarbonyl, Benzyl and the like. The reaction may be promoted by coupling agent known in the art of organic synthesis such as EDCI (1-(3-Dimethylaminopropyl)-3-ethylcarbodiimide), DCC (N,N'-Dicyclohexylcarbodiimide), in a suitable solvent (e.g. tetrahydrofuran, dichloromethane, N,N-dimethylformamide, dioxane). Typically, a co-catalyst such as HOBT (Hydroxybenzotriazole) will also be present in the reaction mixture. The reaction typically proceeds at room temperature for a time in the range of about 4 up to 12 hours. Protecting group PG$_2$ is removed using conventional methods.

Scheme 3 illustrates the final synthetic step.

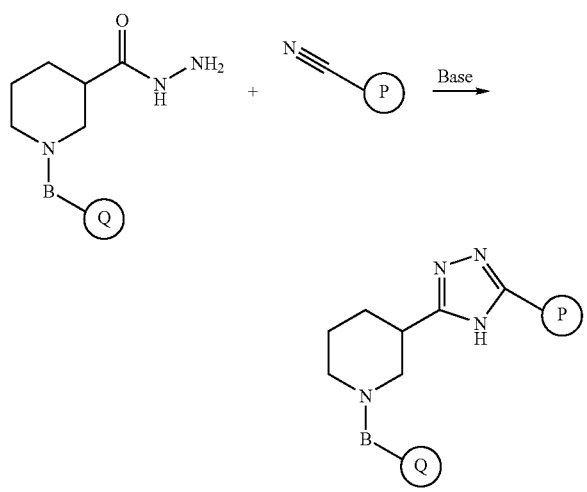

The derivatized hydrazide is reacted with a nitrile derivative (for example 4-Fluoro-benzonitrile) under basic conditions such as sodium methylate or sodium ethylate and the like in a suitable solvent (e.g. methyl alcohol, ethyl alcohol). The reaction typically proceeds by allowing the reaction temperature to warm slowly from ambient temperature to 65° C. for a time in the range of about 24 hours up to 48 hours (see for example Alcalde, Ermitas; Gisbert, Maria; Perez-Garcia, Lluisa; Tetrahedron; 51; 48; 1995; 13365-13378).

In another embodiment of the invention, the compounds of formula I-A wherein A is

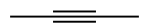

and W is a 3-substituted piperidine ring may be prepared according to the synthetic sequences illustrated in the Schemes 4-6.

Wherein
P and Q each independently is aryl or heteroaryl as described above B represents —C(═O)—C$_0$-C$_2$-alkyl-; —S(═O)2-C$_0$-C$_2$-alkyl-.

Scheme 4

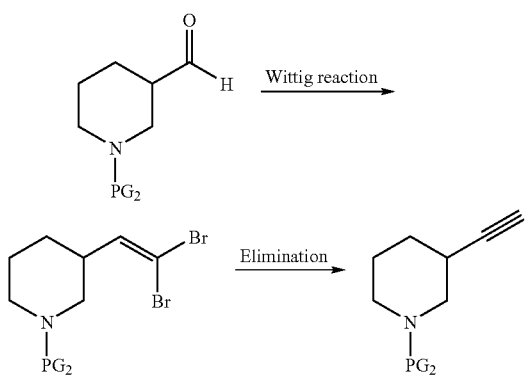

In accordance with the present invention, acethylenic derivatives can be prepared by methods known in the art, for example, by process described above. The free nitrogen of the piperidine moiety is protected with an amino protecting group PG2.

An appropriate aldehyde derivative, for example 3-Formyl-piperidine-1-carboxylic acid tert-butyl ester is converted into the corresponding unsaturated gem-dibromide derivative in a Wittig reaction according to the method illustrated in the patent WO 02/088114. The Wittig reaction may be promoted by a mixture of methylene precursors (for example carbone tetrabromide) and a phosphine such as triphenylphosphine in a suitable solvent (e.g. dichloromethane, tetrahydrofuran, diethylether). If required a catalyst, such as zinc dust, will also be present in the reaction mixture. The reaction is typically allowed to proceed by maintaining at room temperature for a time in the range of about 12 hours up to 24 hours. The unsaturated gem-dibromide compound is then reacted with an organometallic species such as n-butyllithium, tert-Butyllithium and the like which is capable of undergoing metal exchange reaction following by dehydrohalogenation reaction. The reaction may be promoted in suitable solvent (e.g. tetrahydrofuran, ether and the like) at a temperature between −78° C. for 1 hour.

The Scheme 5 illustrates the preparation of disubstituted acetylenic derivatives by reacting an alkyne derivative (described in the Scheme 4), for example 3-Ethynyl-piperidine-1-carboxylic acid tert-butyl ester, with a substituted P, for example 1-Fluoro-4-iodo-benzene. Thus in Scheme 5, X includes halides such as Cl, Br, I or trifluoromethanesulfonyl and paratoluenesulfonyl. Such general route of synthesis has been reported in *J. Med. Chem.* 2000, 43, 4288-4312.

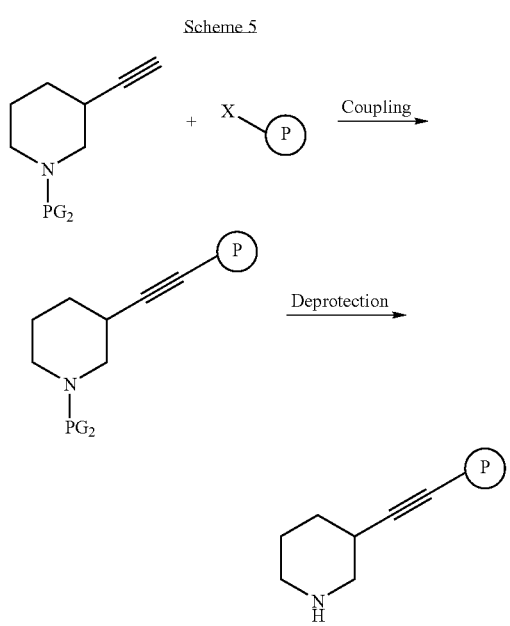

Scheme 5

This palladium catalyzed C—C coupling reaction requires a catalyst such as $PdCl_2(PPh_3)_2$, $Pd(PPh_3)_4$, $Pd(OAc)_2$ or Pd on carbon in a suitable solvent like DMF, acetonitrile or benzene. Typically a co-catalyst such as copper(I) iodide and a base (e.g., triethylamine, diisopropylamine, potassium acetate . . . ) will also be present in the reaction mixture. The coupling reaction typically proceeds by allowing the reaction temperature to warm slowly from about 0° up to ambient temperature, or heated to a temperature anywhere between 30° C. and 150° C. The reaction mixture is then maintained at a suitable temperature for a time in the range of about 1 up to 24 hours, with about 12 hours typically being sufficient. Protecting groups $PG_2$ are removed using standard methods.

Scheme 6

The Scheme 6 illustrates the last step following a process similar to those described in Scheme 1.

The compounds of formula I-A wherein A is

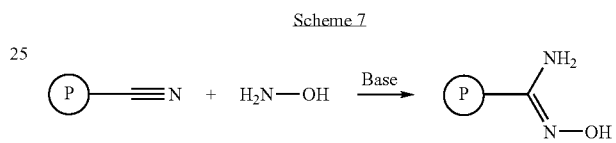

and W is a 3-substituted piperidine ring may be prepared according to the synthetic sequences illustrates in the Schemes 7-10.

Wherein

P and Q each independently is aryl or heteroaryl as described above B represents —C(═O)—$C_0$-$C_2$-alkyl-; —S(═O)2-$C_0$-$C_2$-alkyl-.

The starting material amidoxime can be prepared by methods known in the art of organic synthesis as set forth in part by the following synthesis Scheme 7.

Scheme 7

In turn, a nitrile derivative (for example 4-fluoro-benzonitrile) is reacted with hydroxylamine under neutral or basic conditions such as triethylamine, diisopropyl-ethylamine, sodium carbonate, sodium hydroxide and the like in a suitable solvent (e.g. methyl alcohol, ethyl alcohol). The reaction typically proceeds by allowing the reaction temperature to warm slowly from ambient temperature to a temperature range of 70° C. up to 80° C. inclusive for a time in the range of about 1 hour up to 48 hours inclusive (see for example Lucca, George V. De; Kim, Ui T.; Liang, Jing; Cordova, Beverly; Klabe, Ronald M.; et al; J. Med. Chem.; EN; 41; 13; 1998; 2411-2423, Lila, Christine; Gloanec, Philippe; Cadet, Laurence; Herve, Yolande; Fournier, Jean; et al.; Synth. Commun.; EN; 28; 23; 1998; 4419-4430 and see: Sendzik, Martin; Hui, Hon C.; Tetrahedron Lett.; EN; 44; 2003; 8697-8700 and references therein for reaction under neutral conditions).

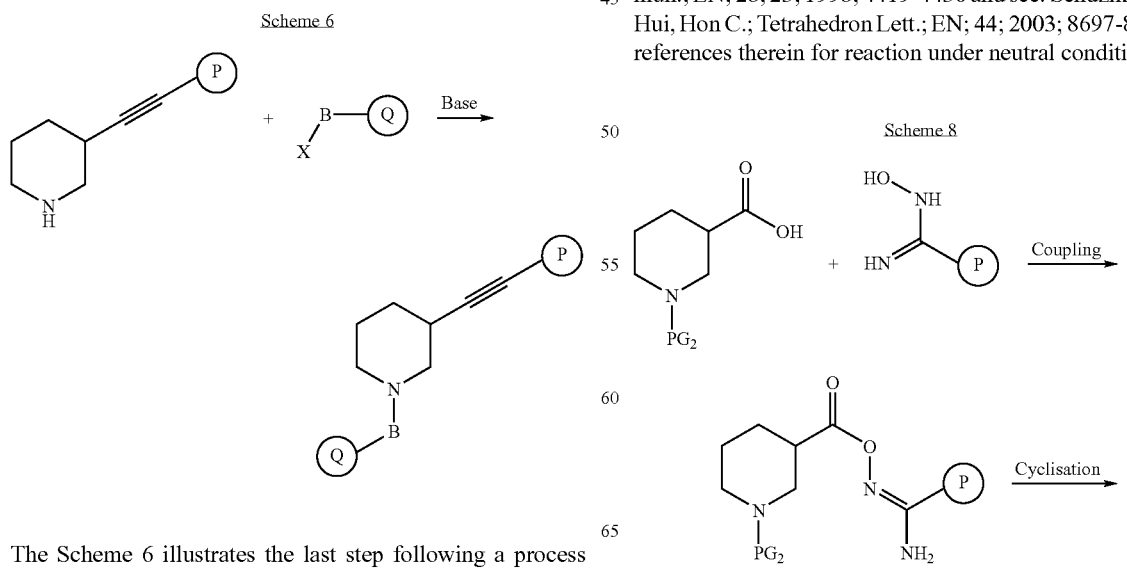

Scheme 8

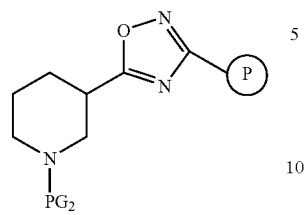

The substituted amidoxime derivative (described in the Scheme 7) may be converted to an acyl-amidoxime derivative using the approach outlined in the Scheme 8. In the Scheme 8, PG$_2$ is a protecting group as defined above. The coupling reaction may be promoted by coupling agents known in the art of organic synthesis such as EDCI (1-(3-Dimethylamino-propyl)-3-ethylcarbodiimide), DCC (N,N'-Dicyclohexyl-carbodiimide), in the presence of a suitable base such as triethylamine, diisopropyl-ethylamine, in a suitable solvent (e.g. tetrahydrofuran, dichloromethane, N,N-dimethylformamide, dioxane). Typically, a co-catalyst such as HOBT (Hydroxy-benzotriazole), HOAT (1-Hydroxy-7-azabenzotriazole) may also be present in the reaction mixture. The reaction typically proceeds at a temperature in the range of ambient temperature up to 60° C. inclusive for a time in the range of about 2 hours up to 12 hours to produce the intermediate acyl-amidoxime. The cyclisation reaction may be effected thermally in a temperature range of about 80° C. up to about 150° C. for a time in the range of about 2 hours up to 18 hours (see for example Suzuki, Takeshi; Iwaoka, Kiyoshi; Imanishi, Naoki; Nagakura, Yukinori; Miyata, Keiji; et al.; Chem. Pharm. Bull.; EN; 47; 1; 1999; 120-122). The product from the reaction can be isolated and purified employing standard techniques, such as extraction, chromatography, crystallization, distillation, and the like.

The final step may be effected either by a process described in the Scheme 9 or by a process described in the Scheme 10.

Scheme 9

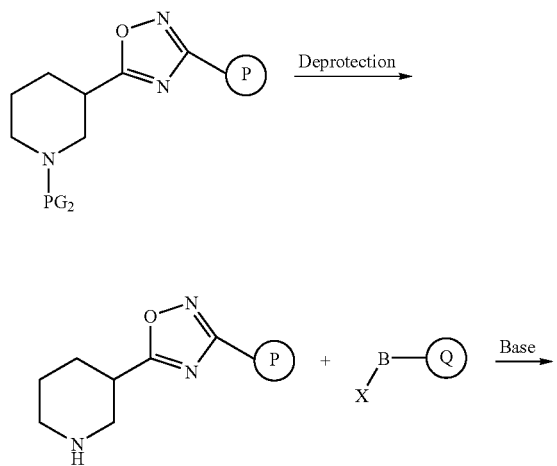

As shown in the Scheme 9, protecting groups PG$_2$ are removed using standard methods. The coupling reaction illustrated in the Scheme 9 is similar to those described in the Scheme 1.

Scheme 10

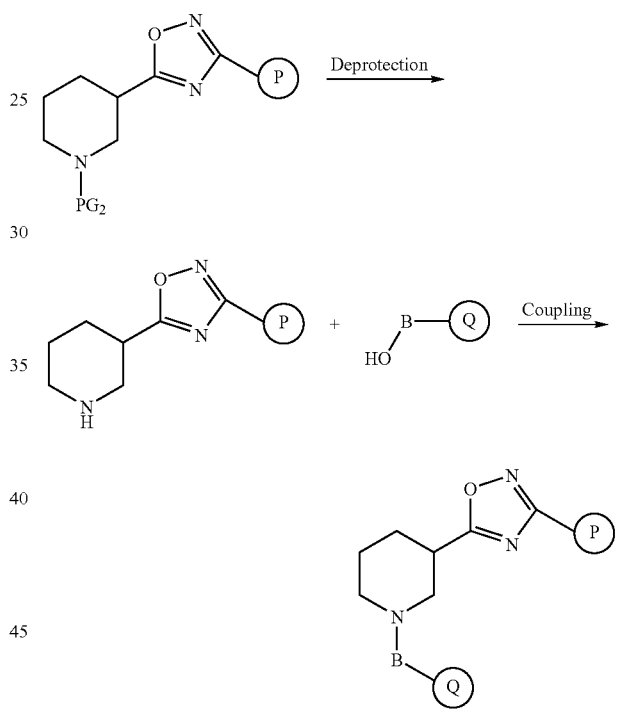

As shown in the Scheme 10, protecting groups PG$_2$ are removed using standard methods. The coupling reaction may be promoted by coupling agents known in the art of organic synthesis such as EDCI (1-(3-Dimethylaminopropyl)-3-ethylcarbodiimide), DCC (N,N'-Dicyclohexyl-carbodiimide) or by polymer-supported coupling agents such as polymer-supported carbodiimide (PS-DCC, ex Argonaut Technologies), in the presence of a suitable base such as triethylamine, diisopropyl-ethylamine, in a suitable solvent (e.g. tetrahydrofuran, dichloromethane, N,N-dimethylformamide, dioxane). Typically, a co-catalyst such as HOBT (1-Hydroxy-benzotriazole), HOAT (1-Hydroxy-7-azabenzotriazole) and the like may also be present in the reaction mixture. The reaction typically proceeds at ambient temperature for a time in the range of about 2 hours up to 12 hours.

The compounds of formula I wherein A is

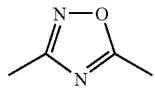

and W is a 2-substituted morpholine ring may be prepared according to the synthetic sequences illustrates in the Schemes 11-12.

Wherein
P and Q each independently is aryl or heteroaryl as described above B represents —C(=O)—$C_0$-$C_2$-alkyl-; —S(=O)2-$C_0$-$C_2$-alkyl-.

Scheme 11

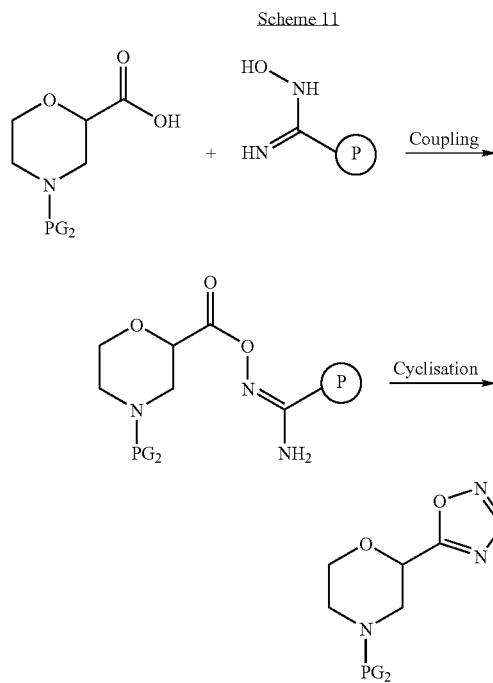

In the Scheme 11, a substituted amido-oxime derivative (described in the Scheme 7) may be converted to an acyl-amido-oxime derivative, by reaction with a morpholine derivative, through a process similar to that described in the Scheme 8. Similarly, the acyl-amido-oxime derivative can be cyclized to a 1,2,4-oxadiazole derivative according to a process described in the Scheme 8.

Scheme 12

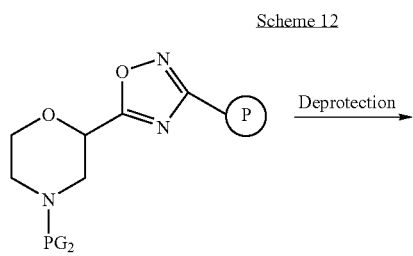

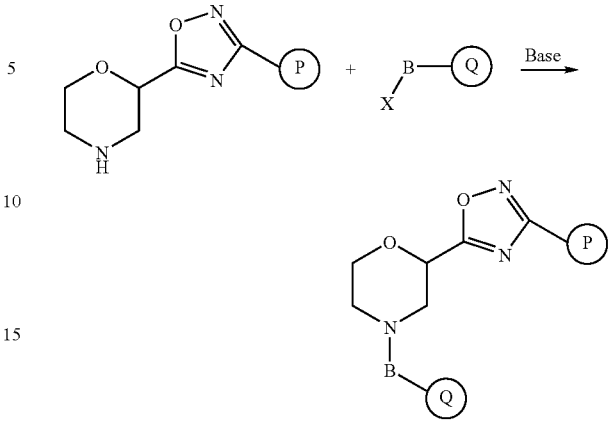

In the Scheme 12, PG2 groups are removed using standard methods. The coupling reaction illustrated in the Scheme 12 is similar to those described in the Scheme 9 and 10.

The compounds of formula I wherein A is and W is a 2-substituted piperazine ring may be prepared according to the synthetic sequences illustrates in the Schemes 13-15.

Wherein
P and Q each independently is aryl or heteroaryl as described above B represents —C(=O)—$C_0$-$C_2$-alkyl-; —S(=O)2-$C_0$-$C_2$-alkyl-.

Scheme 13

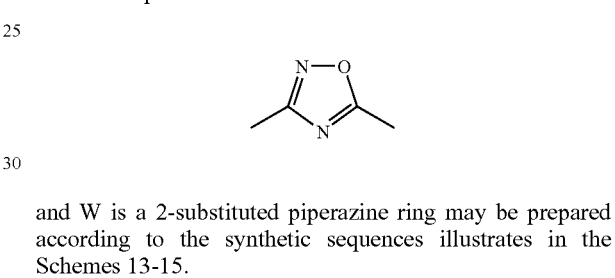

In the Scheme 13, piperazine-2-carboxylic acid is selectively protected at the nitrogen atom at position 4. $PG_2$ is an amino protecting group such as t-butyloxycarbonyl and the like. This reaction may be performed using agents such as 2-(Boc-oxymino)-2-phenylacetonitrile, di-tertbutyl-dicarbonate and the like in a suitable organic solvent (e.g. dioxane, tetrahydrofuran) in mixture with water. Typically, the pH of the reaction mixture will be adjusted to a value in the range of 8 to 12, by addition of a suitable base such as sodium hydroxide, potassium hydroxide, triethylamine and the like. The reaction typically proceeds at room temperature for a time in the range of about 1 hour up to 4 hours (see for example: Bigge, Christopher F.; Hays, Sheryl J.; Novak, Perry M.; Drummond, James T. et al.; Tetrahedron Letters; 30, 39; 1989; 5193-5196 and WO 2004/022061). The $N^4$-protected piperazine derivative can be converted to a piperazine derivative substituted at position 1, using standard conditions for reductive amination. $R_{11}$ may be for instance C1-C6-alkyl, C3-C6-cycloalkyl, C3-C7-cycloalkylalkyl, arylalkyl, heteroarylalkyl. The reaction may be performed by reacting the $N^4$-protected piperazine derivative with an aldehyde or a ketone (for example, formaldehyde), in the presence of a suitable reducing agent such as sodium triacetoxy-borohydride, sodium cyano-borohydride, sodium borohydride and the like, in a suitable solvent such as acetonitrile, tetrahydrofuran, methanol, ethanol, 1,2-dichloroethane and the like. Typically, addition of an acid to decrease the pH of the reaction mixture to a pH of less than about 7 may be necessary to effect reaction, wherein the acid is added as needed and the acid is such as acetic acid, hydrochloric acid and the like. The reaction typically proceeds at room temperature for a time in the range of about 2 hours up to 4 hours.

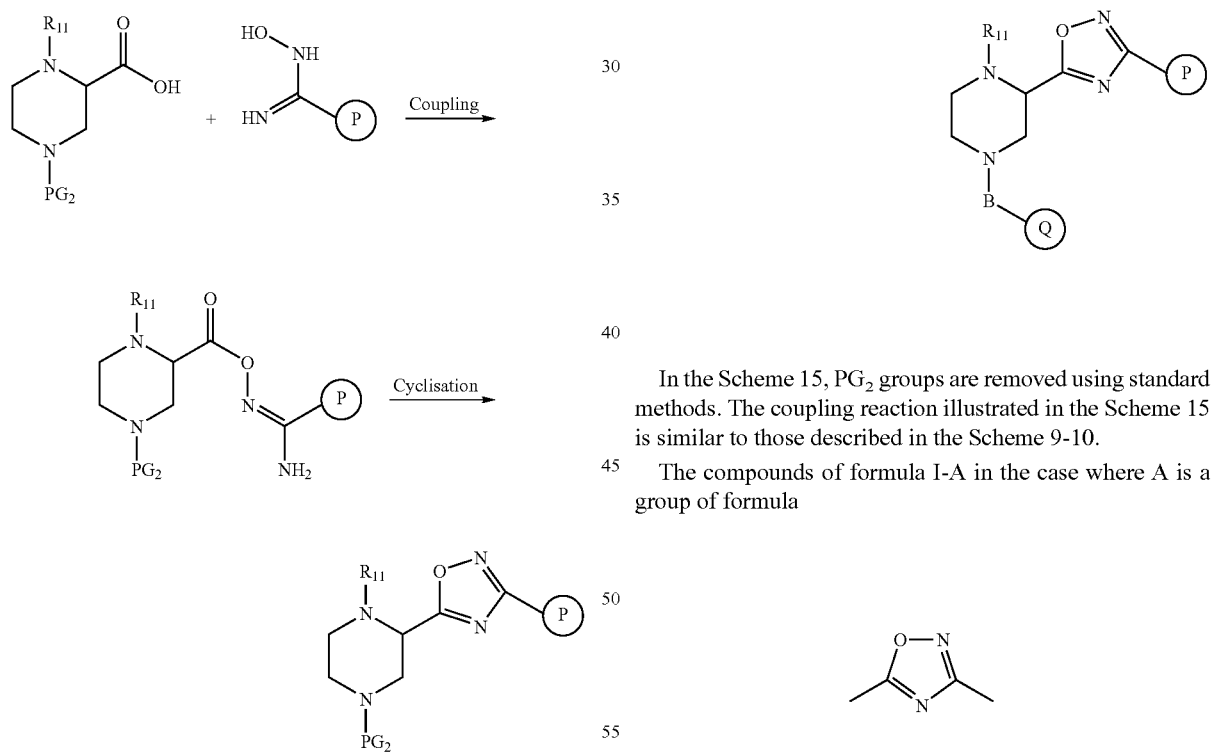

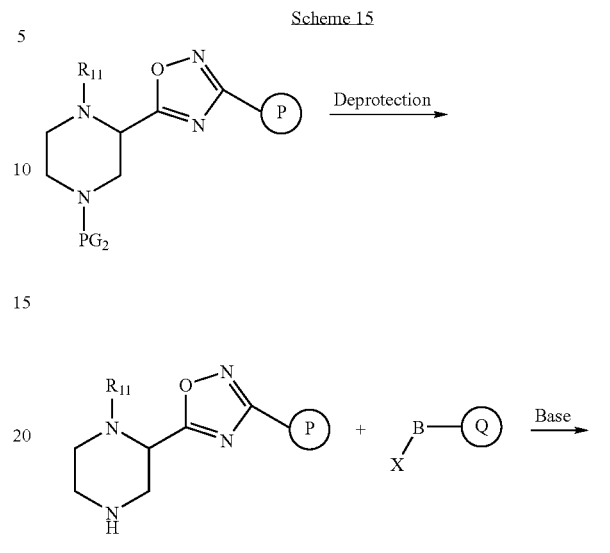

In the Scheme 14, a substituted amido-oxime derivative (described in the Scheme 7) may be converted to an acyl-amido-oxime derivative, by reaction with a piperazine derivative (described in the Scheme 13), through a process similar to that described in the Scheme 8. Similarly, the acyl-amido-oxime derivative can be cyclized to a 1,2,4-oxadiazole derivative according to a process described in the Scheme 8.

In the Scheme 15, $PG_2$ groups are removed using standard methods. The coupling reaction illustrated in the Scheme 15 is similar to those described in the Scheme 9-10.

The compounds of formula I-A in the case where A is a group of formula

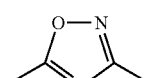

and W is a 3-substituted piperidine ring may be prepared according to the synthetic sequences illustrated in the Scheme 16.

Wherein

P and Q each independently is aryl or heteroaryl as described above B represents —C(=O)—$C_0$-$C_2$-alkyl-; —S(=O)2-$C_0$-$C_2$-alkyl-.

Scheme 16

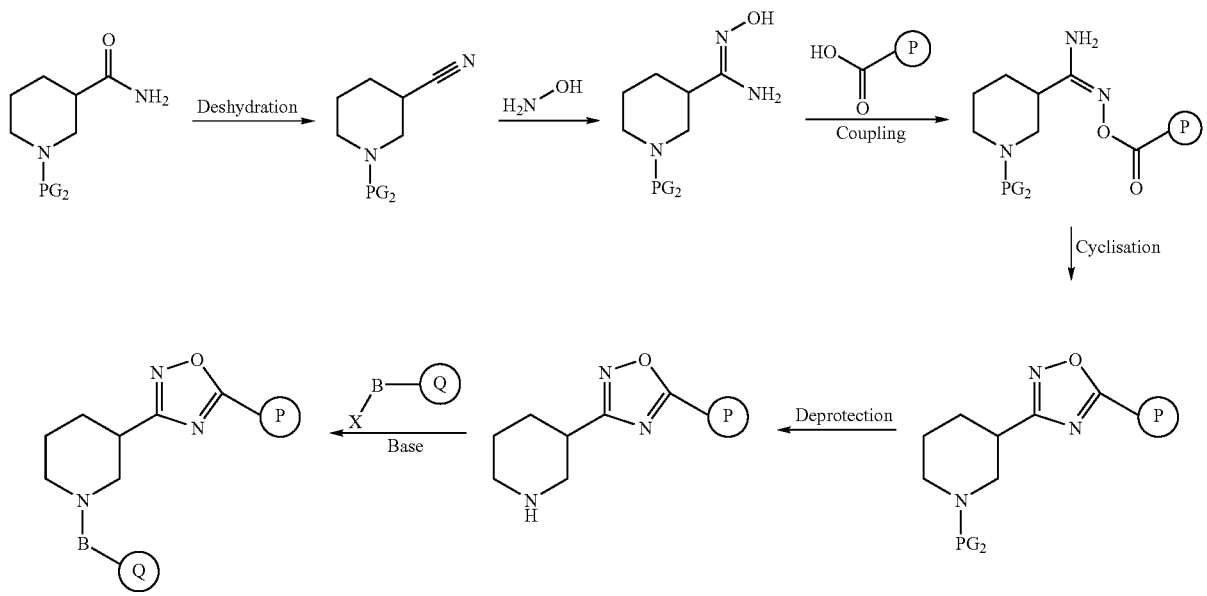

The oxadiazole ring described above is prepared following synthetic routes well known in the art (A. R. Katrizky A. R. and C. W. Rees (1984) *Comprehensive Heterocyclic Chemistry*, Pergamon Press).

The compounds of formula I-A in the case where A is a group of formula

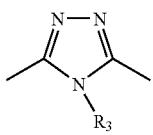

and W is a 3-substituted piperidine ring may be prepared according to the synthetic sequences illustrated in the Schemes 17-19.

Wherein
P and Q each independently is aryl or heteroaryl as described above B represents —C(=O)—C$_0$-C$_2$-allyl-; —S(=O)2-C$_0$-C$_2$-alkyl-.

Scheme 17

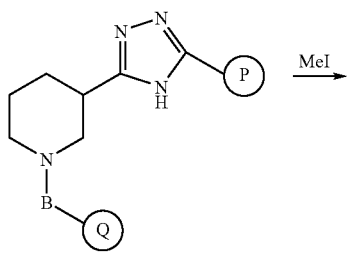

-continued

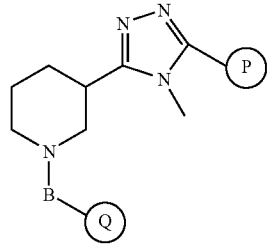

The alkylation of the triazole derivatives (described in the Scheme 1-3) with a alkylating agent such as Methyl iodide and the like under basic condition (e.g. NaH, MeONa and the like) afford the N-Alkyl-triazole derivative (see for example Tarrago, Georges; Marzin, Claude; Najimi, Ouafa; Pellegrin, Valdo; J. Org. Chem.; 55; 2; 1990; 420-425). Alternatively a different reaction sequence can be used for the preparation of these derivatives as described in Scheme 18-19.

Scheme 18

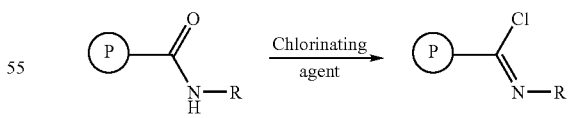

A secondary amide (for example N-Methyl-4-fluoro-benzamide) is converted into an imidoyl chloride, using the approach outlined in the Scheme 18. R$_3$can be for instance C1-C6-alkyl, C3-C6-cycloalkyl, C3-C7-cycloalkylalkyl, arylalkyl, heteroarylalkyl, aryl, heteroaryl. Typically, the secondary amide is reacted with a chlorinating agent such as thionyl chloride, phosphorus pentachloride, phosphorus oxychloride and the like in a suitable solvent (e.g. dichloromethane, chloroform, tetrahydrofuran) or also using the chlorinating agent in large excess as a solvent. The reaction typically proceeds by allowing the reaction temperature to warm slowly from ambient temperature to a temperature in the range of 40° C. up to 110° C. inclusive for a time in the range of about 1 hour up to 4 hours.

Scheme 19

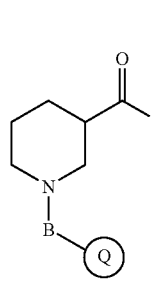 + 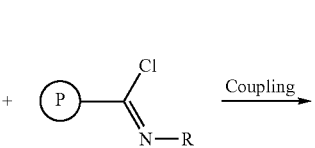 →(Coupling)

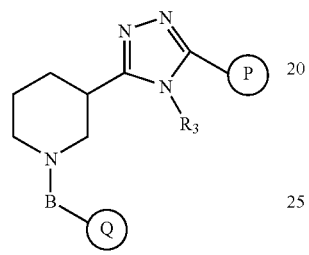

In the Scheme 19, the derivatized hydrazide (described in the Scheme 2) may be reacted with an imidoyl chloride (described in the Scheme 18) according to a process detailed in the Scheme 19. The reaction may be promoted by an appropriate base such as triethylamine, diisopropylethylamine, potassium carbonate in a suitable solvent (e.g. toluene, dioxane, tetrahydrofuran). The reaction typically proceeds by allowing the reaction temperature to warm slowly from ambient temperature to a temperature in the range of 60° C. up to 110° C. inclusive for a time in the range of about 1 hour up to 8 hours (see for example: Clemence, Francois; Joliveau-Maushart, Claudine; Meier, Jean; Cerede, Jean et al.; Eur. J. Med. Chem.; 20; 3; 1985; 257-266 and references therein).

The compounds of formula I-A in the case where A is a group of formula

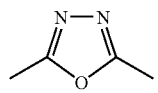

and W is a 3-substituted piperidine ring may be prepared according to the synthetic sequences illustrated in the Schemes 20-21.

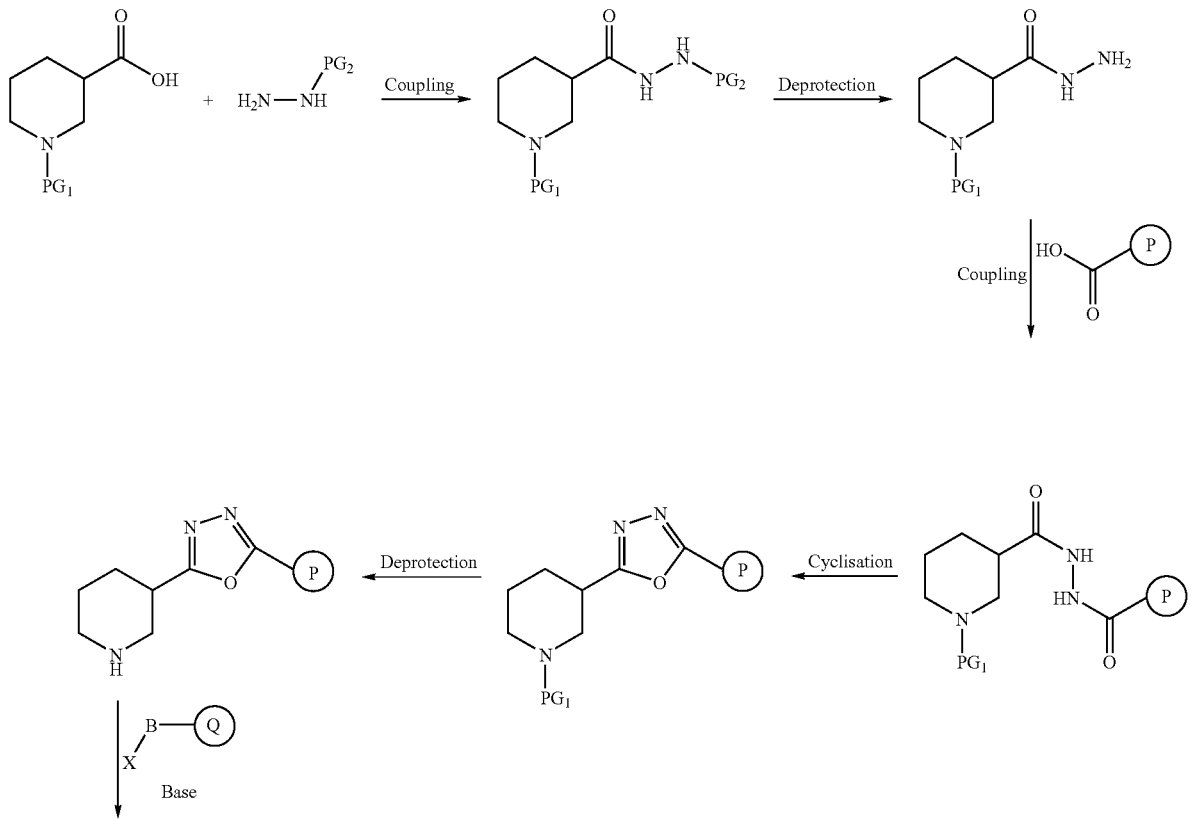

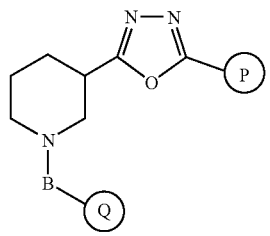

The oxadiazole ring describe above are prepared following synthetic routes well known in the art (A. R. Katnizy A. R and C. W. Rees (1984) *Comprehensive Heterocyclic Chemistry*, Pergamon Press).

Alternatively a different synthetic procedure can be used as described in the Sceme 21.

Scheme 21

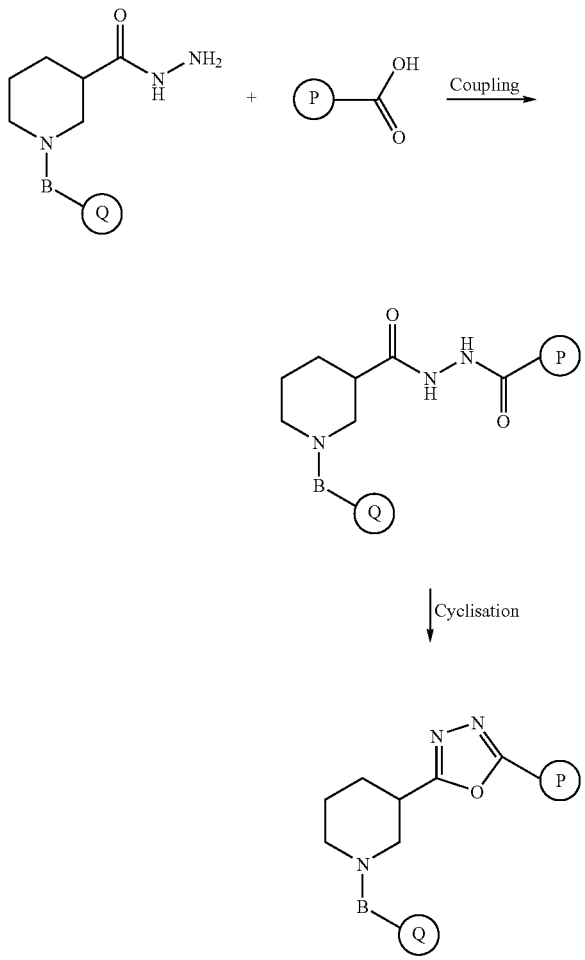

The derivatized hydrazide (prepared as described in the Scheme 2) may be reacted with an acid under suitable coupling conditions. The coupling reaction may be promoted by coupling agents known in the art of organic synthesis such as EDCI (1-(3-Dimethylaminopropyl)-3-ethylcarbodiimide), DCC (N,N'-Dicyclohexyl-carbodiimide) or by polymer-supported coupling agents such as polymer-supported carbodiimide (PS-DCC, ex Argonaut Technologies), in the presence of a suitable base such as triethylamine, diisopropyl-ethylamine, in a suitable solvent (e.g. tetrahydrofuran, dichloromethane, N,N-dimethylformamide, dioxane). Typically, a co-catalyst such as HOBT (1-Hydroxy-benzotriazole), HOAT (1-Hydroxy-7-azabenzotriazole) and the like may also be present in the reaction mixture. The reaction typically proceeds at ambient temperature for a time in the range of about 2 hours up to 12 hours.

The cyclisation step can be performed in the presence of a dehydrating agent such as phosphorus oxychloride, thionyl chloride and the like in a suitable solvent (e.g. acetonitrile, pyridine) or using the dehydrating agent in excess as a solvent. Typically the reaction proceeds at a temperature in the range of 70° C. up to 110° C. for a time in the range of 2 hours up to 4 hours. Alternatively and more preferably, the cyclisation step can be performed in the presence of 4-toluensulfonyl chloride and solid-supported BEMP in a suitable solvent such as THF, dioxane and the like, using conventional or microwave heating, according to a procedure described in the literature (see: Brain, Christopher T., Brunton, Shirley A.; Synlett, 3, 2001, 382-384).

The compounds of formula I-A in the case where A is a group of formula

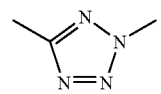

and W is a 3-substituted piperidine ring may be prepared according to the synthetic sequences illustrated in the Schemes 28-29

Wherein
P and Q each independently is aryl or heteroaryl as described above B represents —C(=O)—C$_0$-C$_2$-alkyl-; —S(=O)2-C$_0$-C$_2$-alkyl-.

Scheme 22

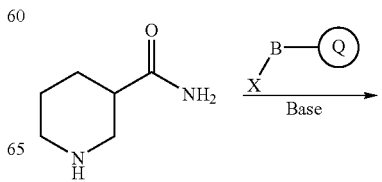

-continued

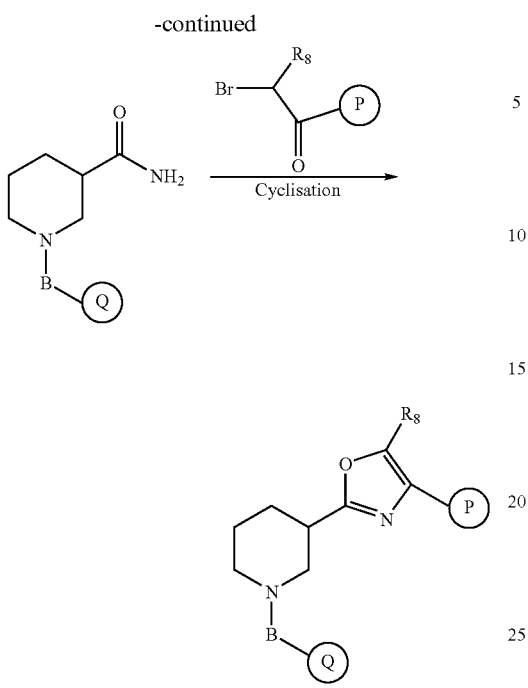

The oxazole ring describe above are prepared following synthetic routes well known in the art (A. R. Katrizky A. R. and C. W. Rees (1984) *Comprehensive Heterocyclic Chemistry*, Pergamon Press).

The compounds of formula I-A in the case with A is a group of formula

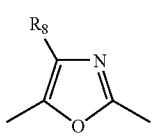

and W is a 3-substituted piperidine ring may be prepared according to the synthetic sequences illustrated in the Schemes 23.

Wherein

P and Q each independently is aryl or heteroaryl as described above B represents —C(═O)—C$_0$-C$_2$-alkyl-; —S(═O)2-C$_0$-C$_2$-alkyl-.

Scheme 23

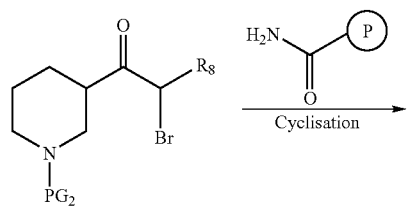

-continued

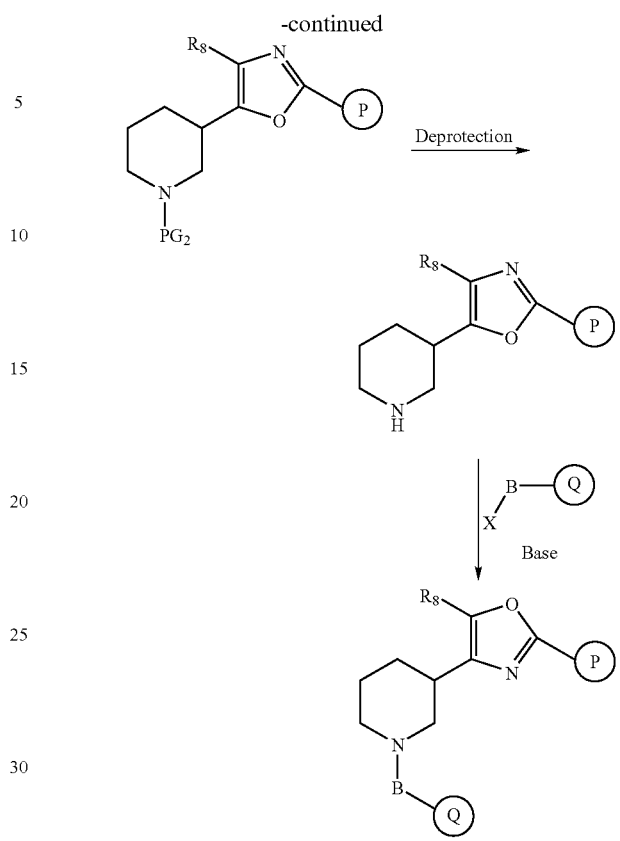

The precursor α-Bromo-ketone derivatives described above are prepared according to synthetic routes well known in the art.

The compounds of formula I-A in the case with A is a group of formula

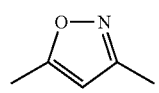

and W is a 3-substituted piperidine ring may be prepared according to the synthetic sequences illustrated in the Schemes 24.

Wherein

P and Q each independently is aryl or heteroaryl as described above B represents —C(═O)—C$_0$-C$_2$-alkyl-; —S(═O)2-C$_0$-C$_2$-alkyl-.

Scheme 24

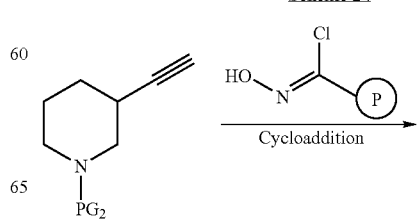

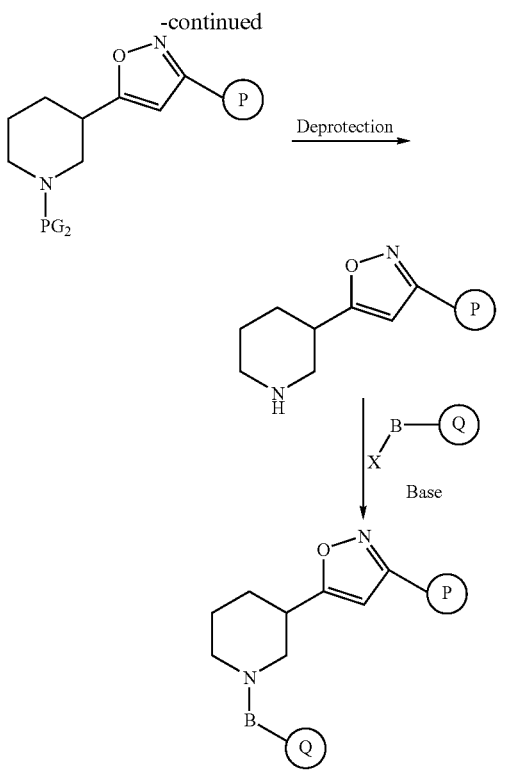

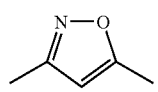

Another embodiment of the present invention, a substituted acetylenic derivative (described in the Scheme 4) may be converted to an oxazole derivative by reacting with an imino-chloride of aryl-oxime following synthetic routes well known in the art (see for example Diana, Guy D.; Volkots, Deborah L.; Nitz, Theodore J.; Bailey, Thomas R.; Long, Melody A.; et al.; J. Med. Chem.; 37; 15; 1994; 2421-2436.).

The compounds o formula I-A in the case with A is a group of formula and W is a 3-substituted piperidine ring may be prepared according to the synthetic sequences illustrated in the Schemes 25.

Wherein

P and Q each independently is aryl or heteroaryl as described above B represents —C(═O)—C$_0$-C$_2$-alkyl-; —S(═O)2-C$_0$-C$_2$-allyl-.

Scheme 25

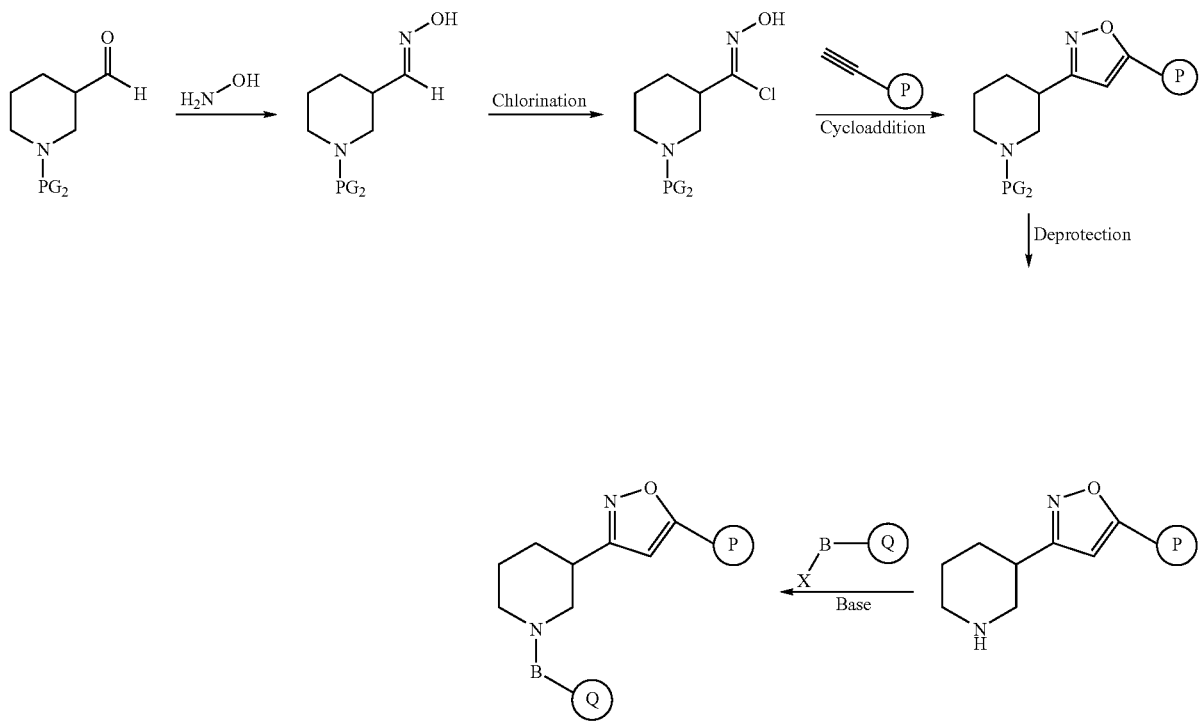

According to the present invention, a substituted acetylenic derivative may be converted to an oxazole derivative by reacting with an imino-chloride of aryl-oxime following synthetic routes well known in the art (see for example Diana, Guy D.; Volkots, Deborah L.; Nitz, Theodore J.; Bailey, Thomas P; Long, Melody A.; et al.; J. Med. Chem.; 37; 15; 1994; 2421-2436.).

The compounds of formula I-A in the case where A is a group of formula

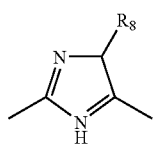

and W is a 3-substituted piperidine ring may be prepared according to the synthetic sequences illustrated in the Schemes 26.

Wherein
P and Q each independently is aryl or heteroaryl as described above B represents —C(═O)—$C_0$-$C_2$-alkyl-; —S(═O)2-$C_0$-$C_2$-alkyl-.

According to the present invention, a substituted amidine derivative may be converted to an imidazole derivative by reacting with an a-bromo-ketone following synthetic routes well known in the art (A. R. Katrizky A. R. and C. W. Rees (1984) *Comprehensive Heterocyclic Chemistry*, Pergamon Press).

The compounds of formula I-A in the case where A is a group of formula

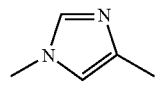

and W is a 3-substituted piperidine ring may be prepared according to the synthetic sequences illustrated in the Schemes 27.

Wherein
P and Q each independently is aryl or heteroaryl as described above B represents —C(═O)—$C_0$-$C_2$-alkyl-; —S(═O)2-$C_0$-$C_2$-alkyl-.

Scheme 26

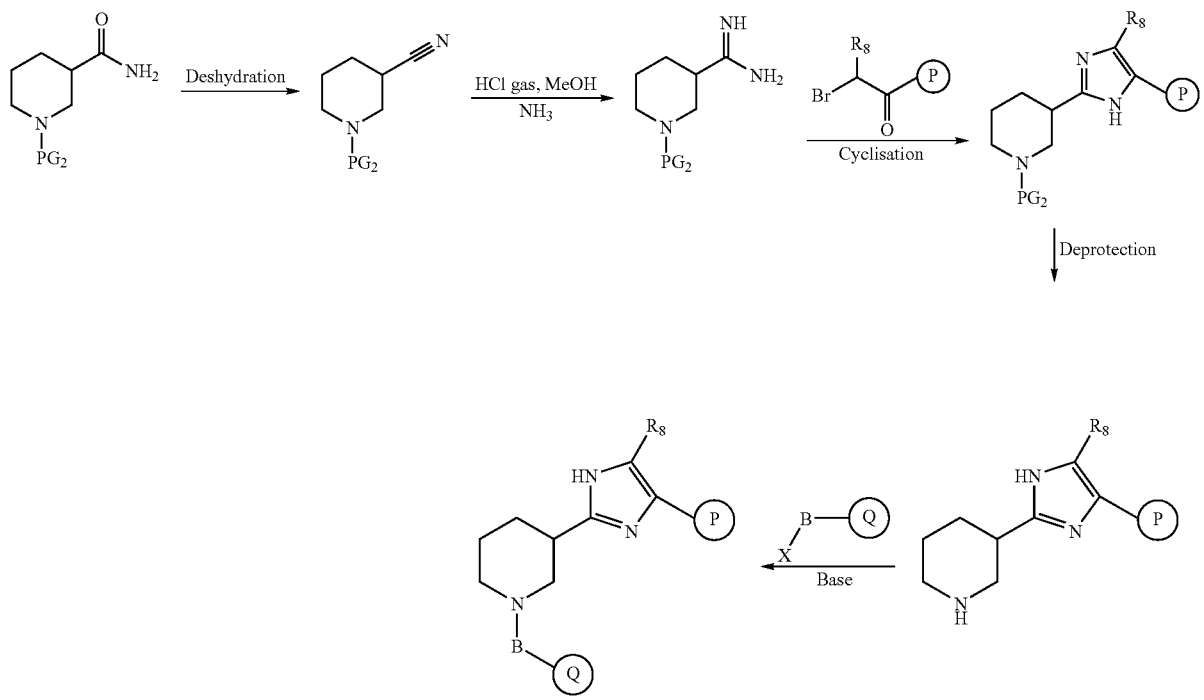

Scheme 27

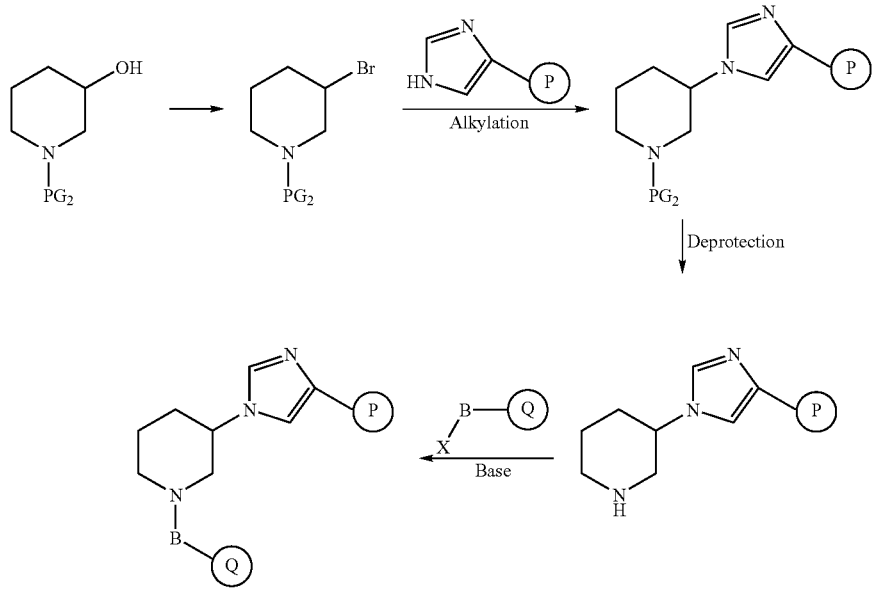

The precursor N-Aryl-imidazole derivatives are prepared according to synthetic routes well known in the art (A. R. Katrizky A. R. and C. W. Rees (1984) *Comprehensive Heterocyclic Chemistry*, Pergamon Press).

The compounds of formula I-A in the case where A is a group of formula

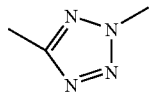

and W is a 3-substituted piperidine ring may be prepared according to the synthetic sequences illustrated in the Schemes 28-29.

Wherein

P and Q each independently is aryl or heteroaryl as described above B represents —C(=O)—C$_0$-C$_2$-alkyl-; —S(=O)2-C$_0$-C$_2$-alkyl-.

Scheme 28

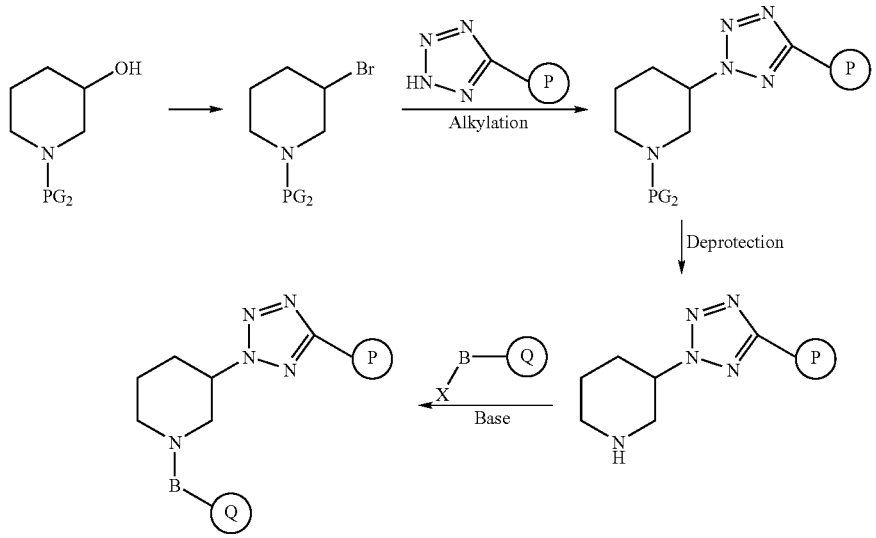

The precursor aryl-tetrazole derivatives are prepared according to synthetic routes well known in the art (A. R. Katrizky A. R. and C. W. Rees (1984) *Comprehensive Heterocyclic Chemistry*, Pergamon Press).

Alternatively these derivatives can be synthesized according to the synthetic sequence presented in the Scheme 29

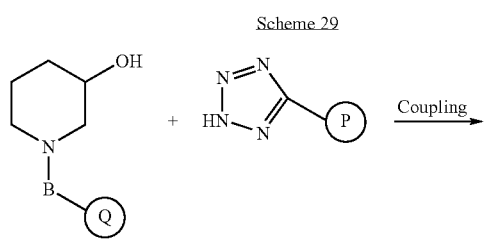

Scheme 29

Aryl tetrazole, prepared according to synthetic procedures well known in the art, can be alkylated with a 3-hydroxypiperidine derivative under Mitsunobu coupling conditions, as described in the literature (see for example: Synthetic Commun.; 26; 14; 1996; 2687-2694).

The compounds of formula I-A in the case where A is a group of formula and W is a 3-substituted piperidine ring may be prepared according to the synthetic sequences illustrated in the Schemes 30.

Wherein

P and Q each independently is aryl or heteroaryl as described above B represents —C(=O)—C$_0$-C$_2$-alkyl-; —S(=O)2-C$_0$-C$_2$-alkyl-.

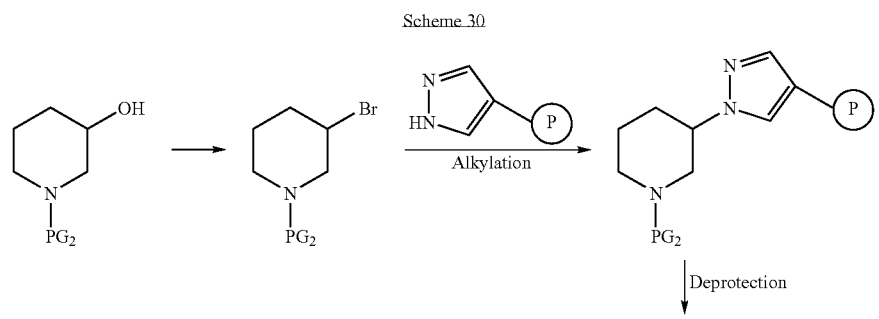

Scheme 30

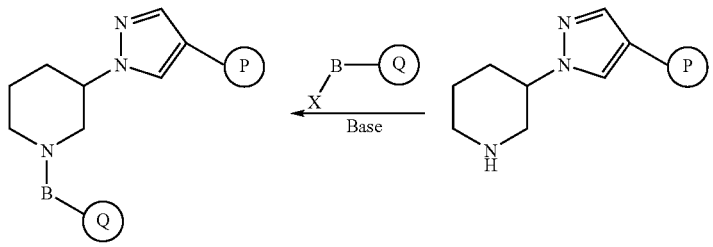

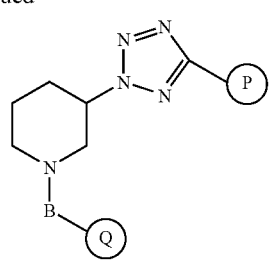

-continued

The precursor Aryl-pyrazole derivatives are prepared according to synthetic routes well known in the art (A. R. Katrizky A. R. and C. W. Rees (1984) *Comprehensive Heterocyclic Chemistry*, Pergamon Press).

The compounds of formula I-A in the case where A is a group of formula

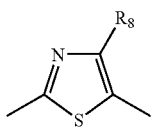

and W is a 3-substituted piperidine ring may be prepared according to the synthetic sequences illustrated in the Schemes 31.

Wherein
P and Q each independently is aryl or heteroaryl as described above B represents —C(=O)—$C_0$-$C_2$-alkyl-; —S(=O)2-$C_0$-$C_2$-alkyl-.

The Scheme 32 illustrates the preparation of disubstituted ethylenic derivatives by reacting an protected vinyl piperidine, with a substituted P, for example 1-Fluoro-4-iodo-benzene. Thus in Scheme 5, X includes halides such as Cl, Br, I or trifluoromethanesulfonyl and paratoluenesulfonyl. Such general route of synthesis has been reported in Artzhur D: Brosius and al.; *JACS.* 1999, 121, 700-709.

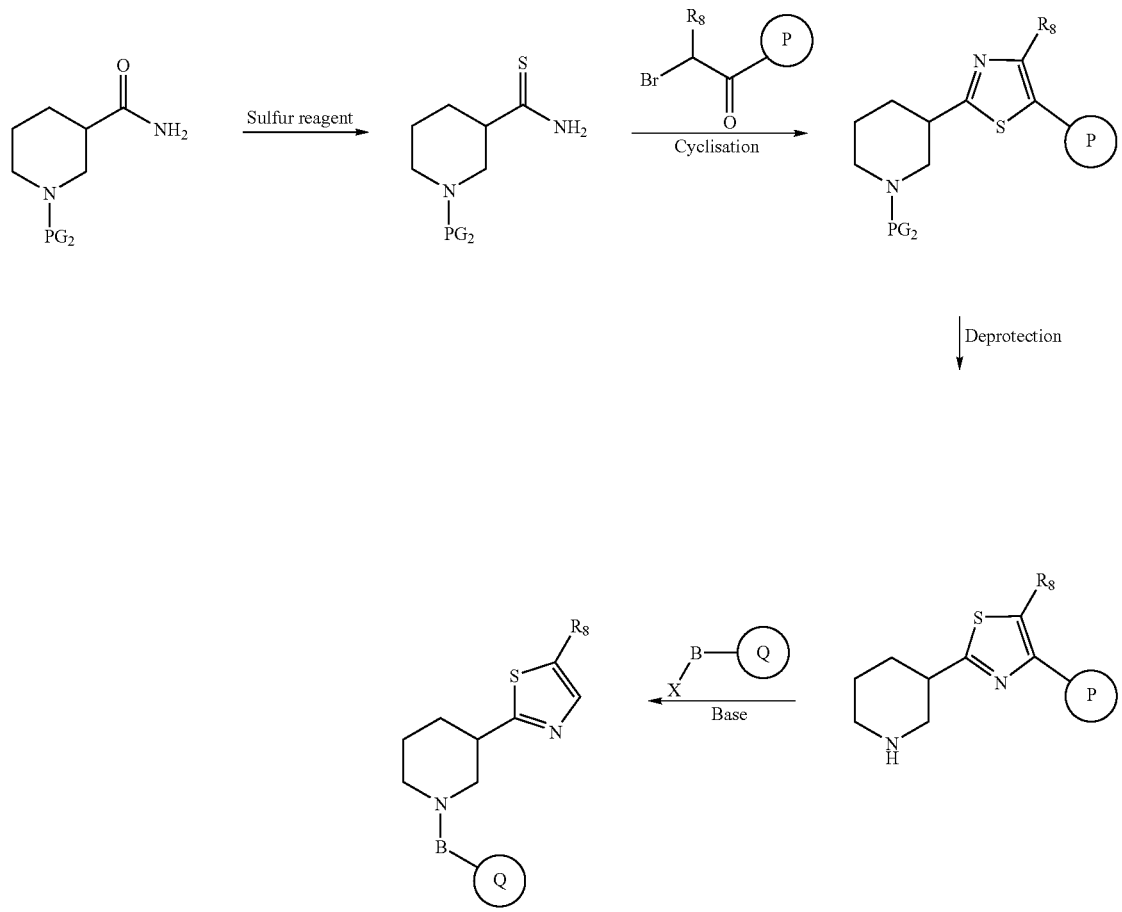

Scheme 31

The compounds of formula I-A in the case where A is a group of formula

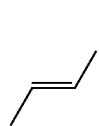

and W is a 3-substituted piperidine ring may be prepared according to the synthetic sequences illustrated in the Schemes 32.

Wherein
P and Q each independently is aryl or heteroaryl as described above B represents —C(=O)—$C_0$-$C_2$-alkyl-; —S(=O)2-$C_0$-$C_2$-alkyl-.

Scheme 32

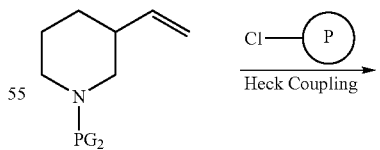

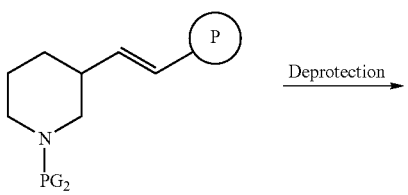

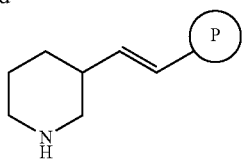

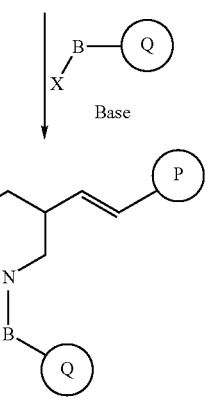

This palladium catalyzed C—C coupling reaction requires a catalyst such as PdCl$_2$(PPh$_3$)$_2$, Pd(PPh$_3$)$_4$, Pd(OAc)$_2$ or Pd on carbon in a suitable solvent like DMF, acetonitrile or benzene. Typically a co-catalyst such as copper(I) iodide and a base (e.g., triethylamine, diisopropylamine, potassium acetate . . . ) will also be present in the reaction mixture. The coupling reaction typically proceeds by allowing the reaction temperature to warm slowly from about 0° up to ambient temperature, or heated to a temperature anywhere between 30° C. and 150° C. The reaction mixture is then maintained at a suitable temperature for a time in the range of about 1 up to 24 hours, with about 12 hours typically being sufficient. Protecting groups PG$_2$ are removed using standard methods.

The precursor protected vinyl piperidine derivative is prepared according to synthetic routes well known in the art (see for example Artzhur D: Brosius and al.; *JACS*. 1999, 121, 700-709).

The compounds of formula I-A in the case where A is a group of formula

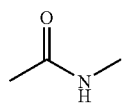

and W is a 3-substituted piperidine ring may be prepared according to the synthetic sequences illustrated in the Scheme 33.

Wherein
P and Q each independently is aryl or heteroaryl as described above B represents —C(═O)—C$_0$-C$_2$-alkyl-; —S(═O)2-C$_0$-C$_2$-alkyl-.

In the Scheme 33, PG$_2$ is an amino protecting group such as tert-Butyloxycarbonyl, Benzyloxycarbonyl, Ethoxycarbonyl, Benzyl and the like, B is as defined above, X is halogen. The amide formation may be promoted by coupling agents known in the art of organic synthesis such as EDCI (1-(3-Dimethylaminopropyl)-3-ethylcarbodiimide), DCC (N,N'-Dicyclohexyl-carbodiimide), in a suitable solvent (e.g. tetrahydrofuran, dichloromethane, N,N-dimethylformamide, dioxane). Typically, a co-catalyst such as HOBT (Hydroxybenzotriazole) will also be present in the reaction mixture. The reaction typically proceeds either at room temperature or at a temperature in the range of 40° C. up to 80° C. inclusive, for a time in the range of about 4 hours up to 48 hours. Protecting groups PG$_2$ are removed using conventional methods. The final step indicated in the Scheme 33 may be promoted by a base such as triethylamine, diisopropylamine, pyridine in a suitable solvent (e.g. tetrahydrofuran, dichloromethane). The reaction typically proceeds by allowing the reaction temperature to warm slowly from 0° C. up to ambient temperature for a time in the range of about 2 up to 12 hours.

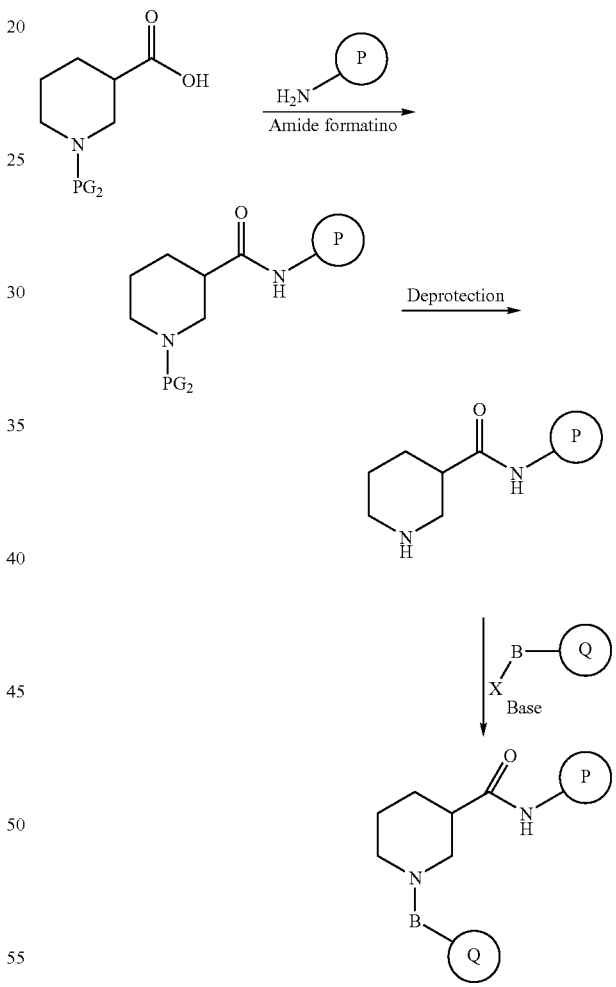

The compounds of formula I-A in the case where A is a group of formula

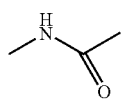

and W is a 3-substituted piperidine ring may be prepared according to the synthetic sequences illustrated in the Scheme 34.

Wherein
P and Q each independently is aryl or heteroaryl as described above B represents —C(=O)—C$_0$-C$_2$-alkyl-; —S(=O)2-C$_0$-C$_2$-alkyl-.

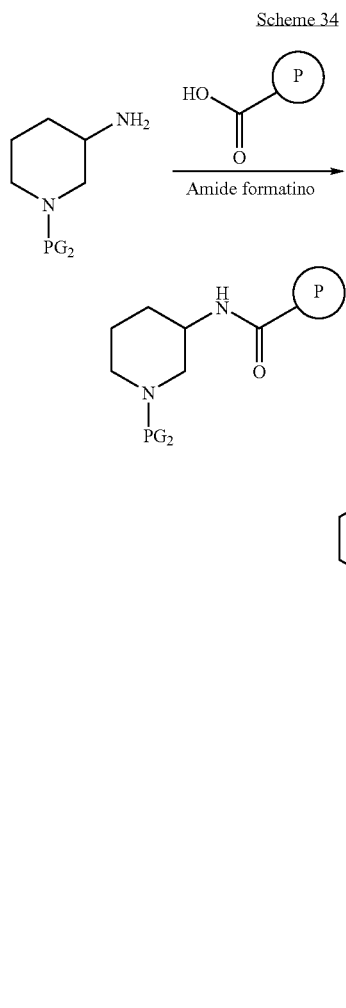

Scheme 34

The compounds of Formula I which are basic in nature can form a wide variety of different pharmaceutically acceptable salts with various inorganic and organic acids. These salts are readily prepared by treating the base compounds with a substantially equivalent amount of the chosen mineral or organic acid in a suitable organic solvent such as methanol, ethanol or isopropanol (see P. Heinrich Stahl, Camille G: Wermuth, *Handbook of Pharmaceuticals Salts, Properties, Selection and Use*, Wiley, 2002).

The following non-limiting examples are intending to illustrate the invention. The physical data given for the compounds exemplified is consistent with the assigned structure of those compounds.

EXAMPLES

Unless otherwise noted, all starting materials were obtained from commercial suppliers and used without further purification. Specifically, the following abbreviation may be used in the examples and throughout the specification.

| | |
|---|---|
| g (grams) | Tr (retention time) |
| Mg (milligrams) | MeOH (methanol) |
| ml (milliliters) | MeOH (methanol) |
| μl (microliters) | Hz (Herts) |
| M (molar) | LCMS (Liquid Chromatography |
| MHz (megahertz) | Mass Spectrum) |
| mmol (millimoles) | HPLC (High Pressure Liquid |
| Min (minutes) | Chromatography) |
| AcOEt (ethyl acetate) | NMR (Nuclear Magnetic Reasonance) |
| K$_2$CO$_3$ (potassium carbonate) | 1H (proton) |
| PdCl$_2$(PPh$_3$)2 (Bis(triphenyl-phosphine)palladium (II) dichloride | Na$_2$SO$_4$ (sodium sulphate) |
| | MgSO$_4$ (magnesium sulphate) |
| | HOBT (1-hydroxybenzotriazole) |
| CDCl$_3$ (deutered chloroform) | R.T. (Room Temperature) |
| EDCI•HCl (1-3(Dimethylamino-propyl)-3-ethylcarbodiimide, hydrochloride) | NaOH (sodium hydroxide) |
| | h (hour) |
| | HCl (hydrochloric acid) |
| EtOH (ethyl alcohol) | n-BuLi (n-butyllithium) |
| % (percent) | THF (tetrahydrofuran) |
| DCM (dichloromethane) | |
| DIEA (diisopropyl ethyl amine) | |
| Mp (melting point) | |

All references to brine refers to a saturated aqueous solution of NaCl. Unless otherwise indicated, all temperatures are expressed in ° C. (degrees Centigrade). All reactions are conducted not under an inert atmosphere at room temperature unless otherwise noted.

$^1$H NMR spectra were recorded on a Brucker 500 MHz or on a Brucker 300 MHz. Chemical shifts are expressed in parts of million (ppm, δ units). Coupling constants are in units of hertz (Hz) Splitting patterns describe apparent multiplicities and are designated as s (singlet), d (doublet), t (triplet), q (quartet), quint (quintet), m (multiplet).

LCMS were recorded under the following conditions:

Method A) Waters 1525 u Micromass ZQ system. Column 2.1*50 mm stainless steel packed with 2.5 μm XTerra RP C-18; flow rate 0.25 ml/min; mobile phase: A phase=water/acetonitrile 95/5+0.1% TFA, B phase=water/acetonitrile 5/95+0.1% TFA. 0-1.5 min (A: 98%, B: 2%), 1.5-8.0 min (A: 0%, B: 100%), 8.0-11.0 min (A: 0%, B: 100%), 11.0-11.1 min (A: 98%, B: 2%); UV detection Diode Array: 200-400 nm; Injection volume: 5 μl.

Method B) Waters 2795 Alliance HT Micromass ZQ. Column 4.6*75 mm stainless steel packed with 3.5 μm Symmetry RP C-18; flow rate 1.0 ml/min; mobile phase: A phase=water/acetonitrile 95/5+0.05 TFA, B phase=water/acetonitrile 5/95+0.05 TFA. 0-1.0 min (A: 95%, B: 5%), 1.0-11.0 min (A: 0%, B: 100%), 11.0-12.0 min (A: 0%, B: 100%), 12.0-12.1 min (A: 95%, B: 5%); UV detection Diode Array: 200-400 nm; Injection volume: 5 μl.

Method C) Waters Micromass ZQ 2996 system. Column 3.0*50 mm stainless steel packed with 5 μm XTerra RP C-18; flow rate 1.0 ml/min; mobile phase: A phase=0.1% formic acid in water, B phase=0.07% formic acid in acetonitrile. 0-0.5 min (A: 95%, B: 5%), 0.5-6.0 min (A: 0%, B: 100%), 6.0-6.5 min (A: 95%, B: 5%), 6.5-7 min (A: 95%, B: 5%); UV detection Diode Array: 200-400 nm; Injection volume: 3 μl.

All mass spectra were taken under electrospray ionisation (ESI) methods.

Most of the reaction were monitored by thin-layer chromatography on 0.25 mm Macherey-Nagel silica gel plates (60F-2254), visualized with UV light. Flash column chromatography was performed on silica gel (220-440 mesh, Fluka).

Melting point determination was performed on a Buchi B-540 apparatus.

Example 1

(4-Fluoro-phenyl)-{3-[5-(4-fluoro-phenyl)-4H-[1,2,4]triazol-3-yl]-piperidin-1-yl}-methanone

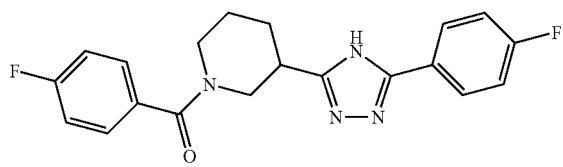

1(A) 1-(4-Fluoro-benzoyl)-piperidine-3-carboxylic acid ethyl ester

To a mixture of Ethyl nipecotate (2 g, 12.72 mmol) in THF (25 ml, 0.5M) was added DIEA (4.79 ml, 27.99 mmol). The reaction mixture was cooled to 0° C. and 4-Fluoro-benzoyl chloride (2.5 g-15.76 mmol) was slowly added. The reaction was to go up to R.T and stirred for 24 h. The solution was concentrated and DCM was added following by HCl 1N. The aqueous phase was separated and organic phase was extracted twice with HCl 1N and twice with water, dried over $Na_2SO_4$, filtered and concentrated to afford 1.15 g (33%) of 1-(4-Fluoro-benzoyl)-piperidine-3-carboxylic acid ethyl ester as a colorless oil which can be used without further purification.

1(B) 1-(4-Fluoro-benzoyl)-piperidine-3-carboxylic acid 1-(4-Fluoro-benzoyl)-piperidine-3-carboxylic acid ethyl ester (1.15 g, 4.42 mmol) was added in a mixture of EtOH/NaOH 3N:1/1 (8 ml) and the resulting heterogeneous solution was stirred at R.T for 1 h. Fuming HCl was added to the mixture until pH=1. The solution was poured with DCM. The organic layer was separated and the aqueous phase was extracted twice with DCM. The combined organic phase was washed twice with water. The solution was dried over $Na_2SO_4$, filtered and concentrated to afford 1.13 g (100%) of 1-(4-Fluoro-benzoyl)-piperidine-3-carboxylic acid as an orange oil which can be used without further purification.

1(C) N'-[1-(4-Fluoro-benzoyl)-piperidine-3-carbonyl]-hydrazinecarboxylic acid tert-butyl ester To a solution of 1-(4-Fluoro-benzoyl)-piperidine-3-carboxylic_acid (1.13 g, 4.50 mmol) in DCM (6.5 ml) was successively added Hydrazinecarboxylic acid tert-butyl ester (0.59 g, 4.50 mmol), HOBT (0.69 g, 4.50 g) and EDCI.HCl (1.29 g, 6.758 mmol). The mixture was stirred at R.T for 72 h. The solvent was removed under reduced pressure and the residue was diluted with DCM was added. The organic layer was washed twice with water, twice with HCl 1N and twice with water. The organic layer was dried over $Na_2SO_4$, filtered and evaporated to afford 1.19 g (73%) of N'-[1-(4-Fluoro-benzoyl)-piperidine-3-carbonyl]-hydrazinecarboxylic acid tert-butyl ester as a colorless semi-solid.

1(D) 1-(4-Fluoro-benzoyl)-piperidine-3-carboxylic acid hydrazide

N'-[1-(4-Fluoro-benzoyl)-piperidine-3-carbonyl]-hydrazinecarboxylic acid tert-butyl ester was dissolved in 8 ml of 4N HCl (dioxane solution). The resulting reaction mixture was stirred at R.T. for 1 h and concentrated to afford 0.88 g (100%) of 1-(4-Fluoro-benzoyl)-piperidine-3-carboxylic acid hydrazide hydrochloride as a white solid.

1(E) (4-Fluoro-phenyl)-{3-[5-(4-fluoro-phenyl)-4H-[1,2,4]triazol-3-yl]-piperidin-1-yl}-methanone A solution of 4-Fluorobenzonitrile (0.48 g, 4.02 mmol) in methanol (3 ml) was treated with sodium metal (77 mg, 0.35 mmol) and stirred at ambiante temperature for 1 h. After this time, the mixture was added to the solution of 1-(4-Fluoro-benzoyl)-piperidine-3-carboxylic acid hydrazide (0.89 g, 3.35 mmol) in methanol (2 ml), and the resulting solution was heated at reflux for 72 h.

The mixture was concentrated, dissolved in water and neutralized with HCl 1N. The aqueous phase was extracted with DCM, and the organic layer was dried over $Na_2SO_4$, filtered and concentrated. The purification by reverse phase SPE (water/ACN 45/55) afford 87 mg (7%) of (4-Fluoro-phenyl)-{3-[5-(4-fluoro-phenyl)-4H-[1,2,4]triazol-3-yl]-piperidin-1-yl}-methanone as a white solid.

Rf=0.16 (DCM/MeOH: 98/2); LCMS (Tr): 3.66 min (Method C); MS (ES+) gave m/z: 369.2 mp=95° C.;

$^1$H-NMR (CDCl3), δ (ppm): 8.50 (s, NH), 8.05 (m, 2H), 7.52 (m, 2H), 7.15-7.03 (m, 4H), 3.65-3.30 (m, 4H), 2.45 (m, H), 1.85-1.52 (m, 4H).).

Example 2

(4-Fluoro-phenyl)-[3-(4-fluoro-phenylethynyl)-piperidin-1-yl]-methanone

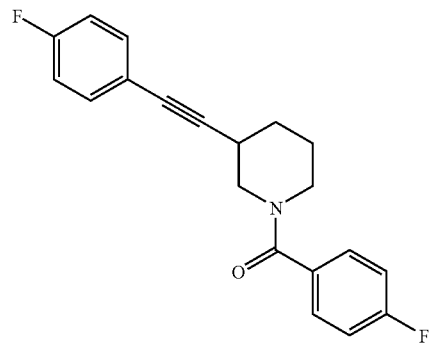

2(A) 3-(2,2-Dibromo-vinyl)-piperidine-1-carboxylic acid tert-butyl ester

To a mixture of $CBr_4$ (1.63 g, 4.92 mmol) and $PPh_3$ (1.29 g, 4.92 mmol 9 in DCM (25 ml) was added 1 g (4.69 mmol) 3-Formyl-piperidine-1-carboxylic acid tert-butyl ester (commercially available) at room temperature. The reaction mixture was stirred at R.T for 24 h and the solvent was removed.

The crude product was purified by flash chromatography (cyclohexane/AcOEt 90/10) to afford 0.15 g (9%) of 3-(2,2-Dibromo-vinyl)-piperidine-1-carboxylic acid tert-butyl ester as a colorless oil.

2(B) 3-Ethynyl-piperidine-1-carboxylic acid tert-butyl ester

To a solution of 3-(2,2-Dibromo-vinyl)-piperidine-1-carboxylic acid tert-butyl ester (0.15 g, 0.42 mmol) in THF (1 ml) wad added at −78° C., 0.5 ml of n-BuLi 2.5 M in hexane (1.23 mmol). After 1 h at −78° C., the reaction mixture was quenched with 1 ml of water and the aqueous phase was extracted with AcOEt. The combined organic phase was dried over $K_2CO_3$, filtered and evaporated to give 80 mg (93%) of 3-Ethynyl-piperidine-1-carboxylic acid tert-butyl ester as a white solid.

2(C) 3-(4-Fluoro-phenylethynyl)-piperidine-1-carboxylic acid tert-butyl ester To a suspension of CuI (4 mg, 0.02 mmol) in $Et_3N$ (1 ml) was added 3-Ethynyl-piperidine-1-carboxylic acid tert-butyl ester (80 mg, 0.38 mmol) followed by $PdCl_2(PPh_3)_2$ (13 mg, 0.02 mmol) and 1-Iodo-4-fluoro-benzene (85 mg, 0.38 mmol). The mixture was stirred 1 h at R.T then heated to 60° C. for 12 h. $Et_3N$ was removed by evaporation. The product was purified by flash chromatography (DCM 100%) to give 0.1 g (89%) of 3-(4-Fluoro-phenylethynyl)-piperidine-1-carboxylic acid tert-butyl ester as a yellow oil.

2(D) 3-(4-Fluoro-phenylethynyl)-piperidine

N'3-(4-Fluoro-phenylethynyl)-piperidine-1-carboxylic acid tert-butyl ester (80.1 mg, 0.34 mmol) was dissolved in 0.2 ml of 4N HCl (dioxane solution). The resulting reaction mixture was stirred at R.T. for 1 h and concentrated to afford 0.14 g (100%) of 3-(4-Fluoro-phenylethynyl)-piperidine hydrochloride as a brown solid.

2(E) (4-Fluoro-phenyl)-[3-(4-fluoro-phenylethynyl)-piperidin-1-yl]-methanone To a mixture of 3-(4-Fluoro-phenylethynyl)-piperidine hydrochloride (0.14 g, 0.58 mmol) in THF (2.3 ml, 0.5M) was added DIEA (0.5 ml, 2.92 mmol). The reaction mixture was cooled to 0° C. and 4-Fluoro-benzoyl chloride (0.139 g-0.87 mmol) was slowly added. The reaction was to go up to R.T and stirred for 24 h. The solution was concentrated and DCM was added following by HCl 1N. The aqueous phase was separated and organic phase was extracted twice with HCl 1N and twice with water, dried over $Na_2SO_4$, filtered and concentrated. The crude product was purified by flash chromatography (DCM/MeOH: 98/2) to afford 0.86 mg (45%) of (4-Fluoro-phenyl)-[3-(4-fluoro-phenylethynyl)-piperidin-1-yl]-methanone as a brown oil. Rf=0.39 (DCM/MeOH: 98/2); LCMS (Tr): 4.14 min (Method C); MS (ES+) gave m/z: 326.2;

$^1$H-NMR (CDCl3), δ (ppm): 8.10 (d, 2H), 7.60 (d, 2H), 7.15 (d, 2H), 6.94 (d, 2H), 3.47-3.30 (m, 4H), 2.54 (m, H), 1.63-1.50 (m, 4H).

Example 3

{3-[3-(4-Methoxy-phenyl)-[1,2,4]oxadiazol-5-yl]-piperidin-1-yl}-phenyl-methanone

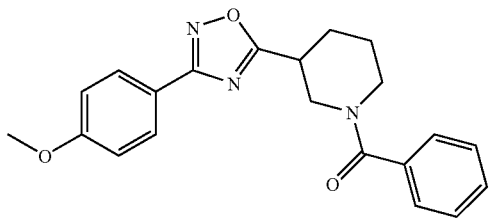

3(A) N-Hydroxy-4-methoxy-benzamidine

To a mixture of 4-Methoxy-benzonitrile (1.07 g, 8 mmol) and DIEA (4.11 ml, 24 mmol) in EtOH (12.5 ml) was added 1.7 g of Hydroxylamine hydrochloride (24 mmol) and the reaction was heated at 70° C. for 48 h. Half of the solvent was removed under reduced pressure. The mixture was poured in DCM (100 ml) and water (30 ml). 2.5 ml of NaOH 1N was added until pH=9-10. The organic layer was separated and the aqueous phase was extracted with DCM. The organics layers were combined, washed with water, dried over $MgSO_4$, filtered and evaporated under reduced pressure to afford 1.3 g (98%) of N-Hydroxy-4-methoxy-benzamidine as a colorless oil which can be used without further purification.

3(B) 3-[3-(4-Methoxy-phenyl)-[1,2,4]oxadiazol-5-yl]-piperidine-1-carboxylic acid tert-butyl ester A mixture of N-Hydroxy-4-methoxy-benzamidine (0.20 g, 1.50 mmol), 1-Boc-piperidine-3-carboxylic acid (0.34 g, 1.50 mmol), HOBT (0.23 g, 1.50 mmol) and EDCl.HCl (0.43 g, 2.25 mmol) in dioxane (2.5 ml) was stirred at R.T for 7 H. After this time the mixture was heated at 80° C. overnight with the carousel Radley's. The mixture was concentrated. The organic layer was washed with water, NaOH 1N and water. The organic layer was dried over $Na_2SO_4$, filtered and evaporated. The crude product was purified by flash chromatography (DCM/MeOH: 99/1) to afford 0.39 mg (72%) of 3-[3-(4-Methoxy-phenyl)-[1,2,4]oxadiazol-5-yl]-piperidine-1-carboxylic acid tert-butyl ester as white solid.

3(C) 3-[3-(4-Methoxy-phenyl)-[1,2,4]oxadiazol-5-yl]-piperidine

3-[3-(4-Methoxy-phenyl)-[1,2,4]oxadiazol-5-yl]-piperidine-1-carboxylic acid tert-butyl ester (0.39 g, 1.08 mmol) was dissolved in 2 ml of 4N HCl (dioxane solution). The resulting reaction mixture was stirred at R.T. for 1 h and concentrated to afford 0.320 g (100%) of 3-[3-(4-Methoxy-phenyl)-[1,2,4]oxadiazol-5-yl]-piperidine hydrochloride as a brown solid.

3(D) {3-[3-(4-Methoxy-phenyl)-[1,2,4]oxadiazol-5-yl]-piperidin-1-yl}-phenyl-methanone To a mixture of 3-[3-(4-Methoxy-phenyl)-[1,2,4]oxadiazol-5-yl]-piperidine hydrochloride (0.320 g, 1.08 mmol) in THF (2.3 ml, 0.5M) was added Pyridine (0.3 ml, 3.78 mmol). The reaction mixture was cooled to 0° C. and 4-Fluorobenzoyl chloride (0.172 g-0.87 mmol) was slowly added. The reaction was to go up to R.T and stirred for 24 h. The solution was concentrated and DCM was added following by HCl 1N. The aqueous phase was separated and organic phase was extracted twice with HCl 1N and twice with water, dried over $Na_2SO_4$, filtered and concentrated. The crude product was purified by flash chromatography (DCM/MeOH: 99/1) to afford 0.26 mg (66%) of {3-[3-(4-Methoxy-phenyl)-[1,2,4]oxadiazol-5-yl]-piperidin-1-yl}-phenyl-methanone as a white powder.

Rf=0.40 (DCM/MeOH: 99/2); LCMS (Tr): 4.35 min (Method C); mp=121° C.; MS (ES+) gave m/z: 364.5;

$^1$H-NMR (CDCl3), δ (ppm): 7.95 (d, 2H), 7.51 (m, H), 7.44-7.37 (m, 4H), 6.83 (d, 2H), 3.75 (s, 3H), 3.63-3.34 (m, 4H), 2.48 (m, H), 1.90-1.50 (m, 4H).

Example 4

(4-Fluoro-phenyl)-{3-[3-(4-fluoro-phenyl)-[1,2,4]oxadiazol-5-yl]-piperidin-1-yl}-methanone

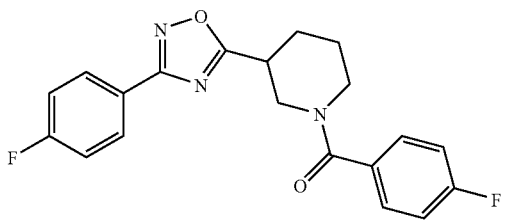

4(A) 3-[3-(4-Fluoro-phenyl)-[1,2,4]oxadiazol-5-yl]-piperidine-1-carboxylic acid tert-butyl ester The compound was prepared following the procedure described in the Example 3, using 4-Fluoro-N-hydroxy-benzamidine (commercially available) and the 1-Boc-piperidine-3-carboxylic acid (Yield: 60%)

4(B) 3-[3-(4-Fluoro-phenyl)-[1,2,4]oxadiazol-5-yl]-piperidine

The compound was prepared following the procedure described in the Example 3(C) (Yield: 100%).

4(C) (4-Fluoro-phenyl)-{3-[3-(4-fluoro-phenyl)-[1,2,4]oxadiazol-5-yl]-piperidin-1-yl}-methanone The compound was prepared following the procedure described in the Example 3(D), using 4-Fluoro-benzoyl chloride as the acyl chloride of choice.

Yield: 22%; mp=118.5-121.5° C. (White powder); Rf=0.30 (DCM/MeOH: 98/2); LCMS (Tr): 4.87 min (Method C); MS (ES+) gave m/z: 370.1;

$^1$H-NMR (CDCl3), δ (ppm): 8.10 (d, 2H), 7.51 (m, 2H), 7.15-7.0.3 (m, 4H), 3.63-3.34 (m, 4H), 2.48 (m, H), 1.90-1.50 (m, 4H).

Ana. Calc'd for $C_{20}H_{17}F_2N_3O_2$: C, 65.03; H, 4.64; N, 11.38; F, 10.29. Found: C, 64.89; H, 4.75; N, 11.26; F, 10.36.

Example 5

{3-[3-(4-Fluoro-phenyl)-[1,2,4]oxadiazol-5-yl]-piperidin-1-yl}-phenyl-methanone

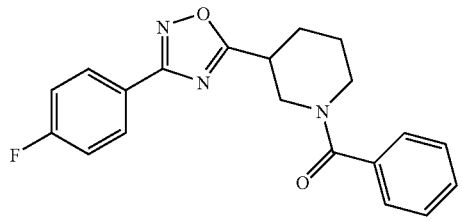

The compound was prepared following the procedure described in the Example 3(D), using 4-Fluoro-benzoyl chloride as the acyl chloride of choice and the 3-[3-(4-Fluoro-phenyl)-[1,2,4]oxadiazol-5-yl]-piperidine hydrochloride (already prepared before in the Example 4(B)). Yield: 30% (white powder); mp=82-83° C.; Rf=0.25 (DCM/MeOH: 98/2);

LCMS (Tr): 4.70 min (Method C); MS (ES+) gave m/z: 352.3

$^1$H-NMR (CDCl3), δ (ppm): 8.10 (d, 2H), 7.51 (m, 3H), 7.15-7.0.3 (m, 4H), 3.63-3.34 (m, 4H), 2.48 (m, H), 1.90-1.50 (m, 4H).

Example 6

(3-Fluoro-phenyl)-{3-[3-(4-fluoro-phenyl)-[1,2,4]oxadiazol-5-yl]-piperidin-1-yl}-methanone

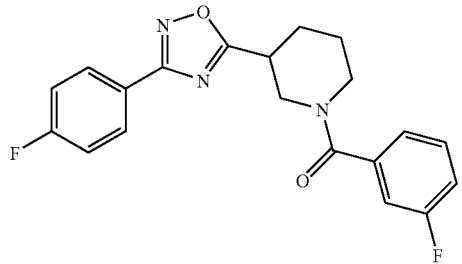

The compound was prepared following the procedure described in the Example 3(D), using 3-Fluoro-benzoyl chloride as the acyl chloride of choice and the 3-[3-(4-Fluoro-phenyl)-[1,2,4]oxadiazol-5-yl]-piperidine hydrochloride (prepared as in the Example 4(B)).

Yield: 42%; mp=139-140° C. (beige powder); Rf=0.32 (DCM/MeOH: 98/2);

LCMS (Tr): 4.87 min (Method C); MS (ES+) gave m/z: 370.1;

$^1$H-NMR (CDCl3), δ (ppm): 8.05 (d, 2H), 7.40-7.50 (m, 3H), 7.22-7.00 (m, 3H), 3.65-3.32 (m, 4H), 2.53 (m, H), 1.86-1.45 (m, 4H).

Example 7

(4-Fluoro-phenyl)-[3-(3-phenyl-[1,2,4]oxadiazol-5-yl)-piperidin-1-yl]-methanone

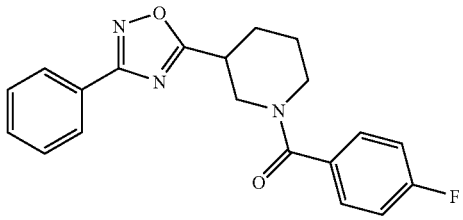

7(A) 3-(3-Phenyl-[1,2,4]oxadiazol-5-yl)-piperidine-1-carboxylic acid tert-butyl ester The compound was prepared following the procedure described in the Example 3(B), using N-hydroxy-benzamidine (commercially available) and the 1-Boc-piperidine-3-carboxylic acid (Yield: 58%).

7(B) 3-(3-Phenyl-[1,2,4]oxadiazol-5-yl)-piperidine

The compound was prepared following the procedure described in the Example 3(C) (Yield: 94%).

7(C) (4-Fluoro-phenyl)-[3-(3-phenyl-[1,2,4]oxadiazol-5-yl)-piperidin-1-yl]-methanone The compound was prepared following the procedure described in the Example 3(D), using 4-Fluoro-benzoyl chloride as the acyl chloride of choice.

Yield: 35%; mp=78-79° C. (white powder); Rf=0.24 (DCM/MeOH: 98/2); LCMS (Tr): 4.75 min (Method C); MS (ES+) gave m/z: 352.3.

$^1$H-NMR (CDCl3), δ (ppm): 8.10 (d, 2H), 7.48-7.32 (m, 4H), 7.22-7.15 (m, 3H), 3.65-3.32 (m, 4H), 2.53 (m, H), 1.86-1.45 (m, 4H).

Example 8

(3-Fluoro-phenyl)-[3-(3-phenyl-[1,2,4]oxadiazol-5-yl)-piperidin-1-yl]-methanone

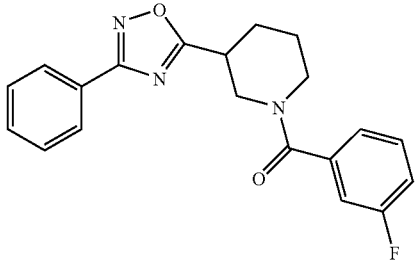

The compound was prepared following the procedure described in the Example 3(D), using 3-Fluoro-benzoyl chloride as the acyl chloride of choice and the 3-(3-Phenyl-[1,2,4]oxadiazol-5-yl)-piperidine hydrochloride (already prepared before in the Example 7). Yield: 53% (yellow oil); Rf=0.25 (DCM/MeOH: 98/2); LCMS (Tr): 4.77 min (Method C); MS (ES+) gave m/z: 352.3.

$^1$H-NMR (CDCl3), σ (ppm): 8.00-7.72 (m, 2H), 7.48-7.40 (m, 3H), 7.32-7.22 (m, 4H), 3.65-3.32 (m, 4H), 2.53 (m, H), 1.86-1.45 (m, 4H).

Example 9

(3-Fluoro-phenyl)-{3-[3-(3-fluoro-phenyl)-[1,2,4]oxadiazol-5-yl]-piperidin-1-yl}-methanone

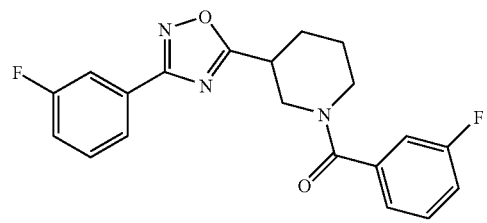

9(A) N-Hydroxy-3-fluoro-benzamidine

To a mixture of 3-Fluoro-benzonitrile (1.21 g, 10 mmol) and DIEA (5.20 ml, 30 mmol) in EtOH (20 ml) was added 2.08 g of Hydroxylamine hydrochloride (30 mmol) and the reaction was heated at 70° C. for 48 h. Half of the solvent was removed under reduced pressure. The mixture was poured in DCM (100 ml) and water (30 ml). 2.5 ml of NaOH 1N was added until pH=9-10. The organic layer was separated and the aqueous phase was extracted with DCM. The organics layers were combined, washed with water, dried over MgSO$_4$, filtered and evaporated under reduced pressure to afford 1.48 g (96%) of N-Hydroxy-3-fluoro-benzamidine as a white solid which can be used without filter purification.

9(B) 3-[3-(3-Fluoro-phenyl)-[1,2,4]oxadiazol-5-yl]-piperidine-1-carboxylic acid tert-butyl ester The compound was prepared following the procedure described in the Example 3(B), using N-Hydroxy-3-fluoro-benzamidine and the 1-Boc-piperidine-3-carboxylic acid (Yield: 78%)

9(C) 3-[3-(3-Fluoro-phenyl)-[1,2,4]oxadiazol-5-yl]-piperidine

The compound was prepared following the procedure described in the Example 3(C) (Yield: 96%).

9(D) (3-Fluoro-phenyl)-{3-[3-(3-fluoro-phenyl)-[1,2,4]oxadiazol-5-yl]-piperidin-1-yl}-methanone The compound was prepared following the procedure described in the Example 3(D), using 3-Fluoro-benzoyl chloride as the acyl chloride of choice (Yield: 54%).

Yield: 53% (yellow oil); Rf=0.31 (DCM/MeOH: 98/2); LCMS (Tr): 4.88 min (Method C); MS (ES+) gave m/z: 370.3;

¹H-NMR (CDCl3), δ (ppm): 7.96-7.72 (m, 2H), 7.66 (m, H), 7.42-7.30 (m, 2H), 7.30-7.25 (m, 2H), 7.00 (m, 1H), 3.65-3.32 (m, 4H), 2.53 (m, H), 1.86-1.45 (m, 4H).

Example 10

(4-Fluoro-phenyl)-{3-[3-(3-fluoro-phenyl)-[1,2,4]oxadiazol-5-yl]-piperidin-1-yl}-methanone

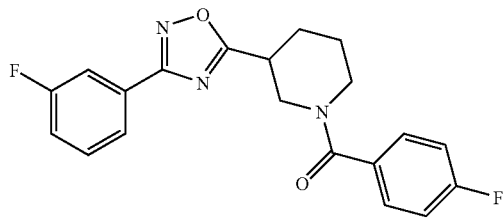

The compound was prepared following the procedure described in the Example 3(D), using 4-Fluoro-benzoyl chloride as the acyl chloride of choice and the 3-[3-(3-Fluoro-phenyl)-[1,2,4]oxadiazol-5-yl]-piperidine hydrochloride (already prepared before in the Example 9). Yield: 50% (yellow oil); Mp=86-89° C. (beige powder); Rf=0.28 (DCM/MeOH: 98/2); LCMS (Tr): 4.88 min (Method C); MS (ES+) gave m/z: 370.3;

¹H-NMR (CDCl3), δ (ppm): 8.05-7.90 (m, 2H), 7.30-7.23 (m, 2H), 7.25-7.15 (m, 3H), 7.00 (m, 1H), 3.65-3.32 (m, 4H), 2.53 (m, H), 1.86-1.45 (m, 4H).

Example 11

R-(4-Fluoro-phenyl)-{3-[3-(4-fluoro-phenyl)-[1,2,4]oxadiazol-5-yl]-piperidin-1-yl}-methanone

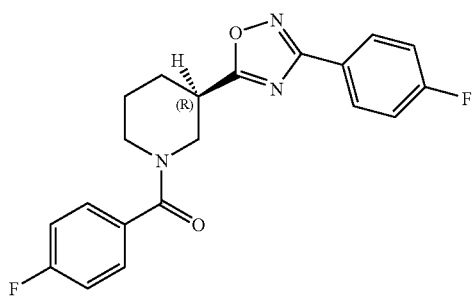

11(A) R-3-[3-(4-Fluoro-phenyl)-[1,2,4]oxadiazol-5-yl]-piperidine-1-carboxylic acid tert-butyl ester The compound was prepared following the procedure described in the Example 3(B), using 4-Fluoro-N-hydroxy-benzamidine (commercially available) and the R-1-Boc-piperidine-3-carboxylic acid (Yield: 79%)

11(B) R-3-[3-(4-Fluoro-phenyl)-[1,2,4]oxadiazol-5-yl]-piperidine

The compound was prepared following the procedure described in the Example 3(C) (Yield: 68%).

11 (C) R-(4-Fluoro-phenyl)-{3-[3-(4-fluoro-phenyl)-[1,2,4]oxadiazol-5-yl]-piperidin-1-yl}-methanone The compound was prepared following the procedure described in the Example 3(D), using 4-Fluoro-benzoyl chloride as the acyl chloride of choice.

Yield: 28%; mp=98° C. (White powder); Rf=0.30 (DCM/MeOH: 98/2);

LCMS (Tr): 4.87 min (Method C); MS (ES+) gave m/z: 370.1;

¹H-NMR (CDCl3), δ (ppm): 8.05 (d, 2H), 7.48 (m, 2H), 7.15-7.0.3 (m, 4H), 3.63-3.34 (m, 4H), 2.48 (m, H), 1.90-1.50 (m, 4H).

Example 12

S-(4-Fluoro-phenyl)-{3-[3-(4-fluoro-phenyl)-[1,2,4]oxadiazol-5-yl]-piperidin-1-yl}-methanone

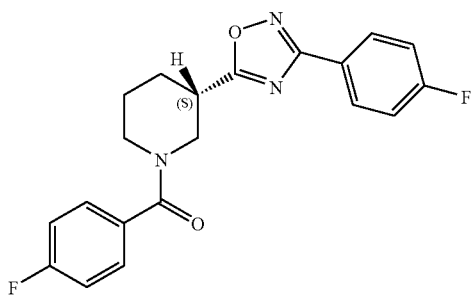

12(A) S-3-[3-(4-Fluoro-phenyl)-[1,2,4]oxadiazol-5-yl]-piperidine-1-carboxylic acid tert-butyl ester The compound was prepared following the procedure described in the Example 3(B), using 4-Fluoro-N-hydroxy-benzamidine (commercially available) and the S-1-Boc-piperidine-3-carboxylic acid (Yield: 84%)

12(B) S-3-[3-(4-Fluoro-phenyl)-[1,2,4]oxadiazol-5-yl]-piperidine

The compound was prepared following the procedure described in the Example 3(C) (Yield: 63%). 12(B) S-(4-Fluoro-phenyl)-{3-[3-(4-fluoro-phenyl)-[1,2,4]oxadiazol-5-yl]-piperidin-1-yl}-methanone The compound was prepared following the procedure described in the Example 3(D), using 4-Fluoro-benzoyl chloride as the acyl chloride of choice.

Yield: 51%; mp=99° C. (White powder); Rf=0.30 (DCM/MeOH: 98/2); [α]$_D^{20}$=+103° (c=1, CHCl$_3$); LCMS (Tr): 4.87 min (Method C); MS (ES+) gave m/z: 370.1. ¹H-NMR (CDCl3), δ (ppm): 8.05 (d, 2H), 7.48 (m, 2H), 7.15-7.0.3 (m, 4H), 3.63-3.34 (m, 4H), 2.48 (m, H), 1.90-1.50 (m, 4H).

Example 13

S-(thiophen-2-yl)-{3-[3-(4-fluoro-phenyl)-[1,2,4]
oxadiazol-5-yl]-piperidin-1-yl}-methanone

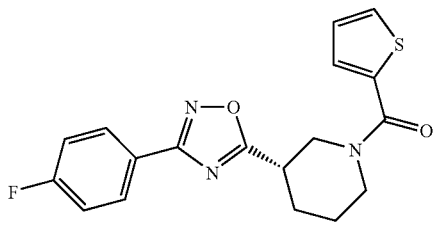

To a suspension of S-3-[3-(4-fluoro-phenyl)-[1,2,4]oxadiazol-5-yl]-piperidine hydrochloride (100 mg, 0.352 mmol, already prepared before in the Example 12) in dry dichloromethane (3 mL), triethylamine (123 uL, 0.881 mmol) and thiophene-2-carbonyl chloride (79 μL, 0.352 mmol) were added dropwise at 0° C. The reaction mixture was allowed to warm at room temperature and stirred overnight under nitrogen atmosphere. The solution was then treated with HCl 1N (5 mL) and the phases were separated. The organic layer was washed subsequently with HCl 1N (5 mL), a saturated aqueous solution of NaHCO$_3$ (5 mL) and water (5 mL), then was dried over Na$_2$SO$_4$ and evaporated under reduced pressure. The crude was passed through a silica gel cartridge (cartridge: VARIAN HF, Mega Bond Elut SI, 5 g; eluent gradient: from DCM 100% to DCM/MeOH 95/5), the solvent was evaporated under reduced pressure to afford 97 mg of S-(thiophen-2-yl)-{3-[3-(4-fluoro-phenyl)-[1,2,4]oxadiazol-5-yl]-piperidin-1-yl}-methanone as a white solid.

Yield: 78%; mp=82-83° C.; $[\alpha]_D^{20}$=+11° (c=1.08, CHCl$_3$); LCMS (Tr): 9.86 min (Method A); MS (ES+) gave m/z: 358.1.

$^1$H-NMR (CDCl$_3$, 338 K, 300 MHz), δ (ppm): 8.06 (dd, 2H); 7.43 (dd, 1H); 7.34 (dd, 1H); 7.14 (dd, 2H); 7.04 (dd, 1H); 4.62 (m, 1H); 4.24 (m, 1H); 3.56 (dd, 1H); 3.36-3.22 (m, 2H); 2.41-2.29 (m, 1H); 2.10-1.89 (m, 2H); 1.81-1.65 (m, 1H).

Example 14

{(S)-3-[3-(4-Fluoro-phenyl)-[1,2,4]oxadiazol-5-yl]-piperidin-1-yl}-(4-methyl-2-pyrazin-2-yl-thiazol-5-yl)-methanone

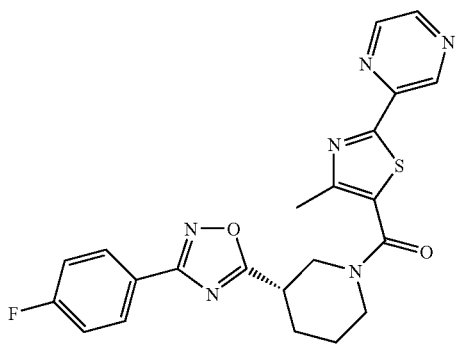

The compound was prepared following the procedure described in the Example 13, using 4-methyl-2-(2-pyrazinyl)-1,3-thiazole-5-carbonyl chloride as the acyl chloride of choice and S-3-[3-(4-fluoro-phenyl)-[1,2,4]oxadiazol-5-yl]-piperidine hydrochloride (prepared as described in the Example 12).

Yield: 47% (off-white solid); mp=147-148° C.; $[\alpha]_D^{20}$=+120° (c=0.34, CHCl$_3$); LCMS (Tr): 9.41 min (Method A); MS (ES+) gave m/z: 451.0.

$^1$H-NMR (CDCl$_3$, 338 K, 300 MHz), δ (ppm): 9.40 (d, 1H); 8.59 (d, 1H); 8.52 (dd, 1H); 8.07 (dd, 2H); 7.14 (dd, 2H); 4.45 (dd br, 1H); 4.04 (dt br, 1H); 3.62 (dd, 1H); 3.39-3.23 (m, 2H); 2.55 (s, 3H); 2.42-2.30 (m, 1 h); 2.12-1.91 (m, 2H); 1.80-1.64 (m, 1H).

Example 15

{(S)-3-[3-(4-Fluoro-phenyl)-[1,2,4]oxadiazol-5-yl]-piperidin-1-1}-(2-phenyl-thiazol-4-yl)-methanone

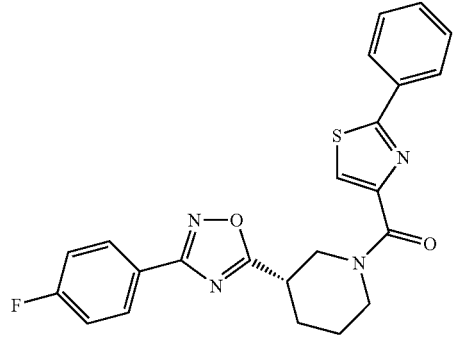

The compound was prepared following the procedure described in the Example 13, using 2-phenyl-1,3-thiazole-4-carbonyl chloride as the acyl chloride of choice and S-3-[3-(4-fluoro-phenyl)-[1,2,4]oxadiazol-5-yl]-piperidine hydrochloride (prepared as described in the Example 12).

Yield: 26% (orange oil); $[\alpha]_D^{20}$=+176° (c=1.13, CHCl$_3$); LCMS (Tr): 10.83 min (Method A); MS (ES+) gave m/z: 435.1.

$^1$H-NMR (CDCl$_3$, 338 K, 300 MHz), δ (ppm): 8.06 (dd, 2H); 7.96 (m, 2H); 7.95 (s, 1H); 7.43 (m, 3H); 7.14 (dd, 2H); 5.04 (d br, 1H); 4.59 (d br, 1H); 3.70-3.38 (m, 2H); 3.27 (dd, 1H); 2.46-2.34 (m, 1H); 2.15-1.92 (m, 2H); 1.91-1.74 (m, 1H).

Example 16

{{(S)-3-[3-(4-Fluoro-phenyl)-[1,2,4]oxadiazol-5-yl]-piperidin-1-yl}-(2-methyl-6-trifluoromethyl-pyridin-3-yl)-methanone

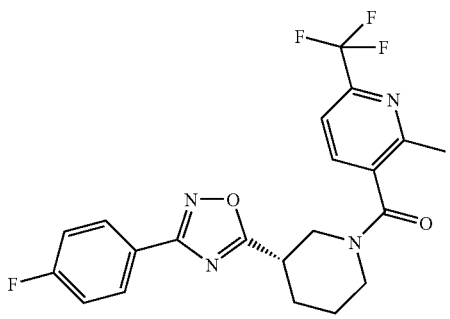

The compound was prepared following the procedure described in the Example 13, using 2-methyl-6-(trifluoromethyl)pyridine-3-carbonyl chloride as the acyl chloride of choice and S-3-[3-(4-fluoro-phenyl)-[1,2,4]oxadiazol-5-yl]-piperidine hydrochloride (prepared as described in the Example 12).

Yield: 54% (yellow waxy solid); $[\alpha]_D^{20}$=+80° (c=1.15, CHCl$_3$); LCMS (Tr): 10.06 min (Method A); MS (ES+) gave m/z: 435.1.

$^1$H-NMR (CDCl$_3$, 338 K, 300 MHz), δ (ppm): 8.05 (m, 2H); 7.63 (d, 1H); 7.52 (d, 1H); 7.15 (dd, 2H); 4.70 (m br, 1H); 4.22 (m br, 1H); 3.64 (m, 1H); 3.54-3.04 (m br, 2H); 2.60 (s, 3H); 2.40-2.26 (m, 1H); 2.17-2.00 (m, 1H); 2.00-1.81 (m br, 1H); 1.81-1.52 (m br, 1H).

Example 17

(3,5-Dimethyl-isoxazol-4-yl)-{(S)-3-[3-(4-fluoro-phenyl)-[1,2,4]oxadiazol-5-yl]-piperidin-1-yl}-methanone

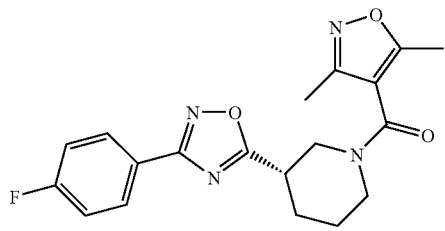

The compound was prepared following the procedure described in the Example 13, using 3,5-dimethylisoxazole-4-carbonyl chloride as the acyl chloride of choice and S-3-[3-(4-fluoro-phenyl)-[1,2,4]oxadiazol-5-yl]-piperidine hydrochloride (prepared as described in the Example 12).

Yield: 20% (colourless oil); $[\alpha]_D^{20}$=+82° (c=0.88, CHCl$_3$); LCMS (Tr): 9.10 min (Method A); MS (ES+) gave m/z: 371.1.

$^1$H-NMR (CDCl$_3$, 338 K, 300 MHz), δ (ppm): 8.06 (dd, 2H); 7.15 (dd, 2H); 4.34 (d br, 1H); 3.88 (d br, 1H); 3.59 (dd, 1H); 3.34-3.17 (m, 2H); 2.40 (s, 3H); 2.33 (m, 1H); 2.26 (s, 3H); 2.12-1.89 (m, 2H); 1.72-1.57 (m, 1H).

Example 18

{(S)-3-[3-(4-Fluoro-phenyl)-[1,2,4]oxadiazol-5-yl]-piperidin-1-yl}-[1,2,3]thiadiazol-4-yl-methanone

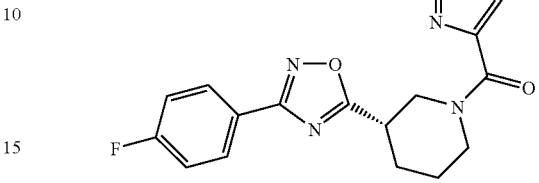

The compound was prepared following the procedure described in the Example 13, using 1,2,3-thiadiazole-4-carbonyl chloride as the acyl chloride of choice and S-3-[3-(4-fluoro-phenyl)-[1,2,4]oxadiazol-5-yl]-piperidine hydrochloride (prepared as described in the Example 12).

Yield: 44% (brownish solid); mp=90-91° C.; $[\alpha]_D^{20}$=+104° (c=0.67, CHCl$_3$); LCMS (Tr): 7.25 min (Method A); MS (ES+) gave m/z: 360.0.

$^1$H-NMR (CDCl$_3$, 343 K, 300 MHz), δ (ppm): 9.09 (s, 1H); 8.04 (m, 2H); 7.14 (dd, 2H); 4.82 (d br, 1H); 4.45 (d br, 1H); 3.78 (m br, 1H); 3.54-3.33 (m, 2H); 2.45-2.33 (m, 1H); 2.16-1.96 (m, 2H); 1.91-1.76 (m, 1H).

Example 19

Benzothiazol-2-yl-{(S)-3-[3-(4-fluoro-phenyl)-[1,2,4]oxadiazol-5-yl]-piperidin-1-yl}-methanone

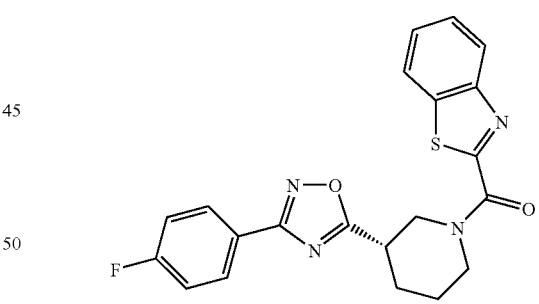

The compound was prepared following the procedure described in the Example 13, using 1,3-benzothiazole-2-carbonyl chloride as the acyl chloride of choice and S-3-[3-(4-fluoro-phenyl)-[1,2,4]oxadiazol-5-yl]-piperidine hydrochloride (prepared as described in the Example 12).

Yield: 70% (beige powder); mp=130-131° C.; $[\alpha]_D^{20}$=+155° (c=0.8, CHCl$_3$); LCMS (Tr): 8.11 min (Method A); MS (ES+) gave m/z: 409.1.

$^1$H-NMR (CDCl$_3$, 333K, 300 MHz), δ (ppm): 8.15-7.87 (m, 4H); 7.58-7.41 (m, 2H); 7.19-7.05 (dd, 2H); 5.59-3.84 (m br, 2H); 3.78-3.20 (m, 3H); 2.47-2.30 (m, 1H); 2.20-1.94 (m, 2H); 1.92-1.73 (m, 1H).

Example 20

{(S)-3-[3-(4-Fluoro-phenyl)-[1,2,4]oxadiazol-5-yl]-piperidin-1-yl}-(5-methyl-isoxazol-3-yl)-methanone

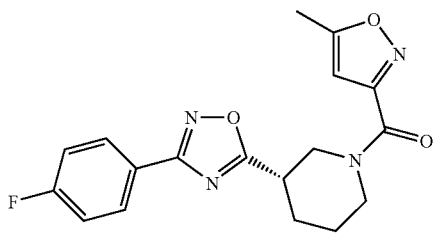

The compound was prepared following the procedure described in the Example 13, using 5-methylisoxazole-3-carbonyl chloride as the acyl chloride of choice and S-3-[3-(4-fluoro-phenyl)-[1,2,4]oxadiazol-5-yl]-piperidine hydrochloride (prepared as described in the Example 12).

Yield: 32% (colourless oil); $[\alpha]_D^{20}=+112°$ (c=1.2, CHCl$_3$); LCMS (Tr): 7.23 min (Method A); MS (ES+) gave m/z: 357.1.

$^1$H-NMR (CDCl$_3$, 333K, 300 MHz), δ (ppm): 8.14-7.96 (m, 2H); 7.20-7.09 (m, 2H); 6.26 (s, 1H); 5.04-4.24 (m br, 2H); 3.97-3.58 (m br, 1H); 3.46-3.13 (m, 2H); 2.45 (s, 3H); 2.41-2.27 (m, 1H); 2.11-1.88 (m, 2H); 1.83-1.67 (m, 1H).

Example 21

(1,5-Dimethyl-1H-pyrazol-3-yl)-{(S)-3-[3-(4-fluoro-phenyl)-[1,2,4]oxadiazol-5-yl]-piperidin-1-yl}-methanone

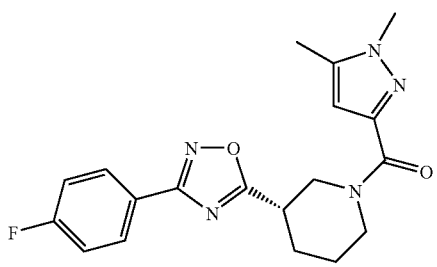

The compound was prepared following the procedure described in the Example 13, using 1,5-dimethyl-1H-pyrazole-3-carbonyl chloride as the acyl chloride of choice and S-3-[3-(4-fluoro-phenyl)-[1,2,4]oxadiazol-5-yl]-piperidine hydrochloride (prepared as described in the Example 12).

Yield: 69% (white solid); mp=108-109° C.; $[\alpha]_D^{20}=+128°$ (c=0.9, CHCl$_3$); LCMS (Tr): 7.00 min (Method A); MS (ES+) gave m/z: 370.2.

$^1$H-NMR (CDCl$_3$, 338 K, 300 MHz), δ (ppm): 8.12-8.02 (m, 2H); 7.20-7.09 (m, 2H); 6.42 (s, 1H); 5.06-4.95 (m, 1H); 4.70-4.54 (m br, 1H); 3.77 (s, 3H); 3.59-3.37 (m br, 1H); 3.36-3.03 (m, 2H); 2.40-2.24 (m br, 1H); 2.27 (s, 3H); 2.08-1.85 (m, 2H); 1.82-1.63 (m, 1H).

Example 22

{(S)-3-[3-(4-Fluoro-phenyl)-[1,2,4]oxadiazol-5-yl]-piperidin-1-yl}-(4-trifluoromethyl-phenyl)-methanone

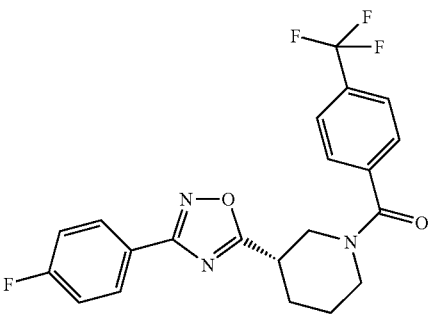

The compound was prepared following the procedure described in the Example 13, using 4-trifluoromethyl benzoyl chloride as the acyl chloride of choice and S-3-[3-(4-fluoro-phenyl)-[1,2,4]oxadiazol-5-yl]-piperidine hydrochloride (prepared as described in the Example 12).

Yield: 54% (white solid); mp=109-110° C.; $[\alpha]_D^{20}=+95°$ (c=0.7, CHCl$_3$); LCMS (Tr): 7.78 min (Method A); MS (ES+) gave m/z: 420.1.

$^1$H-NMR (CDCl$_3$, 333K, 300 MHz), δ (ppm): 8.11-8.0 (m, 2H); 7.67 (d, 2H); 7.52 (d, 2H); 7.20-7.09 (m, 2H); 4.58-4.17 (m br, 1H); 4.07-3.74 (m br 1H); 3.57 (dd, 1H); 3.38-3.17 (m, 2H); 2.40-2.25 (m, 1H); 2.15-1.85 (m, 2H); 1.78-1.58 (m, 1H).

Example 23

4-{(S)-3-[3-(4-Fluoro-phenyl)-[1,2,4]oxadiazol-5-yl]-piperidine-1-carbonyl}-benzonitrile

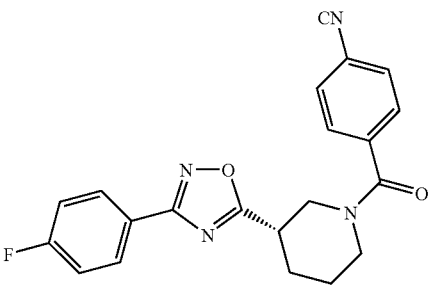

The compound was prepared following the procedure described in the Example 13, using 4-cyano benzoyl chloride as the acyl chloride of choice and S-3-[3-(4-fluoro-phenyl)-[1,2,4]oxadiazol-5-yl]-piperidine hydrochloride (prepared as described in the Example 12).

Yield: 61% (white solid); mp=129-130° C.; $[\alpha]_D^{20}=+127°$ (c=1.1, CHCl$_3$); LCMS (Tr): 7.25 min (Method A); MS (ES+) gave m/z: 377.1.

$^1$H-NMR (CDCl$_3$, 333K, 300 MHz), δ (ppm): 8.10-8.0 (m, 2H); 7.70 (dd, 2H); 7.51 (dd, 2H); 7.21-7.11 (m, 2H); 4.57-

4.11 (m br, 1H); 4.05-3.73 (m br, 1H); 3.58 (dd, 1H); 3.40-3.17 (m, 2H); 2.40-2.26 (m, 1H); 2.16-1.85 (m, 2H); 1.78-1.58 (m, 1H).

Example 24

{(S)-3-[3-(4-Fluoro-phenyl)-[1,2,4]oxadiazol-5-yl]-piperidin-1-yl}-isoxazol-5-yl-methanone

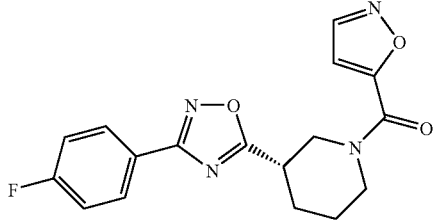

The compound was prepared following the procedure described in the Example 13, using isoxazole-5-carbonyl chloride as the acyl chloride of choice and S-3-[3-(4-fluoro-phenyl)-[1,2,4]oxadiazol-5-yl]-piperidine hydrochloride (prepared as described in the Example 12).

Yield: 50% (white solid); mp=93-94° C.; $[\alpha]_D^{20}$=+127° (c=0.8, CHCl$_3$); LCMS (Tr): 7.00 min (Method A); MS (ES+) gave m/z: 343.1.

$^1$H-NMR (CDCl$_3$, 333K, 300 MHz), δ (ppm): 8.28 (d, 1H); 8.10-8.0 (m, 2H); 7.20-7.09 (m, 2H); 6.75 (d, 1H); 4.87-4.27 (m br, 1H); 4.26-4.06 (m, 1H); 3.86-3.46 (m br, 1H); 3.46-3.20 (m, 2H); 2.46-2.27 (m, 1H); 2.18-1.88 (m, 2H); 1.86-1.67 (m, 1H).

Example 25

(2,4-Difluoro-phenyl)-{(S)-3-[3-(4-fluoro-phenyl)-[1,2,4]oxadiazol-5-yl]-piperidin-1-yl}-methanone

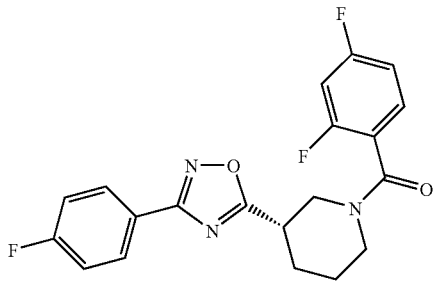

The compound was prepared following the procedure described in the Example 13, using 2,4-difluoro benzoyl chloride as the acyl chloride of choice and S-3-[3-(4-fluoro-phenyl)-[1,2,4]oxadiazol-5-yl]-piperidine hydrochloride (prepared as described in the Example 12).

Yield: 59% (colourless oil); $[\alpha]_D^{20}$=+104° (c=1.1 CHCl$_3$); LCMS (Tr): 7.51 min (Method A); MS (ES+) gave m/z: 388.1.

$^1$H-NMR (CDCl$_3$, 336 K, 300 MHz), δ (ppm): 8.05 (dd, 2H); 7.38 (dd, 1H); 7.15 (dd, 2H); 6.98-6.80 (m, 2H); 5.13-3.72 (m br, 2H); 3.57-3.41 (m, 1H); 3.32-3.14 (m, 2H); 2.41-2.26 (m, 1H); 2.09-1.57 (m, 3H).

Example 26

{(S)-3-[3-(4-Fluoro-phenyl)-[1,2,4]oxadiazol-5-yl]-piperidin-1-yl}-(3,4,5-trifluoro-phenyl)-methanone

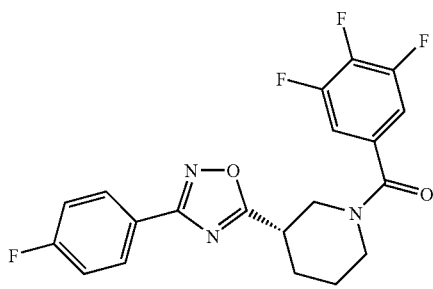

The compound was prepared following the procedure described in the Example 13, using 3,4,5-trifluoro benzoyl chloride as the acyl chloride of choice and S-3-[3-(4-fluoro-phenyl)-[1,2,4]oxadiazol-5-yl]-piperidine hydrochloride (prepared as described in the Example 12).

Yield: 63% (white solid); mp=139-140° C.; $[\alpha]_D^{20}$=+81° (c=1.0, CHCl$_3$); LCMS (Tr): 7.67 min (Method A); MS (ES+) gave m/z: 406.1.

$^1$H-NMR (CDCl$_3$, 336 K, 300 MHz), δ (ppm): 8.10-8.01 (m, 2H); 7.20-7.01 (m, 4H); 4.39-4.20 (m, 1H); 3.92-3.77 (m, 1H); 3.61 (dd, 1H); 3.42-3.18 (m, 2H); 2.38-2.25 (m, 1H); 2.15-1.85 (m, 2H); 1.77-1.59 (m, 1H).

Example 27

(3-Chloro-4-fluoro-phenyl)-{(S)-3-[3-(4-fluoro-phenyl)-[1,2,4]oxadiazol-5-yl]-piperidin-1-yl}-methanone

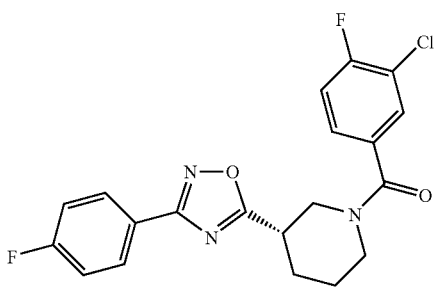

The compound was prepared following the procedure described in the Example 13, using 3-chloro-4-fluoro-benzoyl chloride as the acyl chloride of choice and S-3-[3-(4-fluoro-phenyl)-[1,2,4]oxadiazol-5-yl]-piperidine hydrochloride (prepared as described in the Example 12).

Yield: 56% (white solid); mp=123-124° C.; $[\alpha]_D^{20}$=+94° (c=1.1, CHCl$_3$); LCMS (Tr): 8.00 min (Method A); MS (ES+) gave m/z: 404.1.

$^1$H-NMR (CDCl$_3$, 338 K, 300 MHz), δ (ppm): 8.12-8.00 (m, 2H); 7.51 (dd, 1H); 7.34-7.27 (m, 1H); 7.21-7.10 (m, 3H);

4.445-4.25 (m, 1H); 3.97-3.80 (m, 1H); 3.59 (dd, 1H); 3.40-3.18 (m, 2H); 2.39-2.26 (m, 1H); 2.12-1.86 (m, 2H); 1.77-1.58 (m, 1H).

Example 28

{(S)-3-[3-(4-Fluoro-phenyl)-[1,2,4]oxadiazol-5-yl]-piperidin-1-yl}-(2-phenyl-2H-pyrazol-3-yl)-methanone

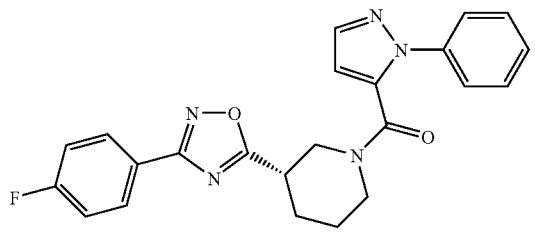

The compound was prepared following the procedure described in the Example 13, using 1-phenyl-1H-pyrazole-5-carbonyl chloride as the acyl chloride of choice and S-3-[3-(4-fluoro-phenyl)-[1,2,4]oxadiazol-5-yl]-piperidine hydrochloride (prepared as described in the Example 12).

Yield: 34% (colourless oil); $[\alpha]_D^{20}=+69°$ (c=0.5, CHCl$_3$); LCMS (Tr): 7.19 min (Method A); MS (ES+) gave m/z: 418.2.

$^1$H-NMR (CDCl$_3$, 338 K, 300 MHz), δ (ppm): 8.10-7.98 (m, 2H); 7.68 (d, 1H); 7.59-7.52 (m, 2H); 7.48-7.31 (m, 3H); 7.19-7.09 (m, 2H); 6.54 (d, 1H); 5.02-4.03 (m br, 1H); 3.91-2.53 (m br, 4H); 2.42-1.68 (m br, 3H); 1.20-0.78 (m br, 1H).

Example 29

{(S)-3-[3-(4-Fluoro-phenyl)-[1,2,4]oxadiazol-5-yl]-piperidin-1-yl}-(5-methyl-2-phenyl-2H-[1,2,3]triazolyl)-methanone

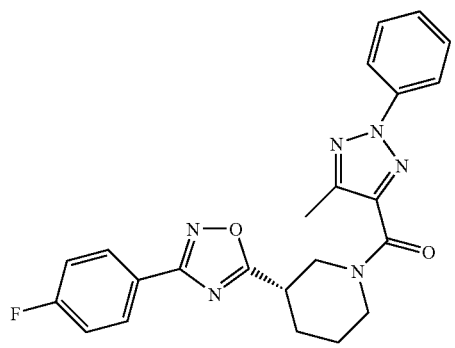

The compound was prepared following the procedure described in the Example 13, using 5-methyl-2-phenyl-2H-1,2,3-triazole-4-carbonyl chloride as the acyl chloride of choice and S-3-[3-(4-fluoro-phenyl)-[1,2,4]oxadiazol-5-yl]-piperidine hydrochloride (prepared as described in the Example 12).

Yield: 20% (off-white oil); $[\alpha]_D^{20}=+86°$ (c=0.3, CHCl$_3$); LCMS (Tr): 8.20 min (Method A); MS (ES+) gave m/z: 433.2.

$^1$H-NMR (CDCl$_3$, 338 K, 300 MHz), δ (ppm): 8.15-7.95 (m, 4H); 7.55-7.28 (m, 3H); 7.22-7.07 (m, 2H); 5.05-4.75 (m br, 1H), 4.57-4.40 (m br, 1H); 3.83-3.65 (m, 1H); 3.56-3.15 (m, 2H); 2.54 (s, 3H); 2.47-2.29 (m, 1H), 2.23-1.66 (m, 3H).

Example 30

(4-Fluoro-3-methyl-phenyl)-{(S)-3-[3-(4-fluoro-phenyl)-[1,2,4]oxadiazol-5-yl]-piperidin-1-yl}-methanone

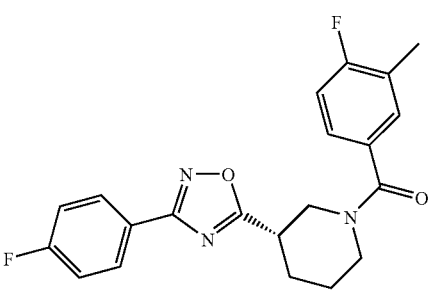

The compound was prepared following the procedure described in the Example 13, using 3-methyl-4-fluoro-benzoyl chloride as the acyl chloride of choice and S-3-[3-(4-fluoro-phenyl)-[1,2,4]oxadiazol-5-yl]-piperidine hydrochloride (prepared as described in the Example 12).

Yield: 52% (white solid); mp=106-107° C.; $[\alpha]_D^{20}=+99°$ (c=1.2, CHCl$_3$); LCMS (Tr): 7.76 min (Method A); MS (ES+) gave m/z: 384.2.

$^1$H-NMR (CDCl$_3$, 338 K, 300 MHz), δ (ppm): 8.11-8.00 (m, 2H); 7.31-7.08 (m, 4H); 7.02 (dd, 1H); 4.49-4.32 (m, 1H); 4.06-3.91 (m, 1H); 3.51 dd, 1H); 3.33-3.17 (m, 2H); 2.38-2.30 (m, 1H); 2.28 (s, 3H); 2.10-1.84 (m, 2H); 1.77-1.58 (m, 1H).

Example 31

{(S)-3-[3-(4-Fluoro-phenyl)-1,2,4-oxadiazol-5-yl]-piperidin-1-yl}-(5-pyridin-2-yl-thiophen-2-yl)-methanone

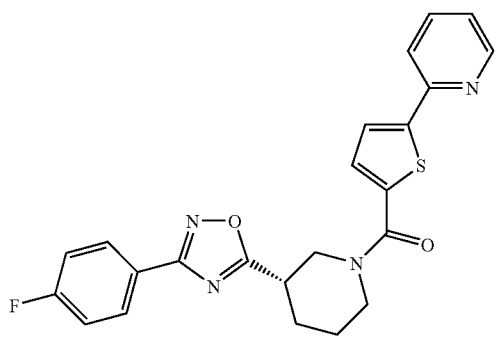

The compound was prepared following the procedure described in the Example 13, using 5-(2-pyridinyl)-2-thiophenecarbonyl chloride as the acyl chloride of choice and S-3-[3-(4-fluoro-phenyl)-[1,2,4]oxadiazol-5-yl]-piperidine hydrochloride (prepared as described in the Example 12).

Yield: 13% (off-white powder); mp=115-117° C.; LCMS (Tr): 5.25 min (Method A); MS (ES+) gave m/z: 435.2.

¹H-NMR (CDCl₃, 300 MHz), δ (ppm): 8.59 (d br, 1H); 8.06 (dd, 2H); 7.73 (dd, 1H); 7.67 (d, 1H); 7.55 (d, 1H); 7.37 (d, 1H); 7.22 (m, 1H); 7.15 (dd, 2H); 4.69 (m, 1H); 4.32 (m, 1H); 3.57 (m, 1H); 3.36-3.24 (m, 2H); 2.37 (m, 1H); 2.09-1.89 (m, 2H); 1.83-1.67 (m, 1H).

Example 32

{(S)-3-[3-(4-Fluoro-phenyl)-1,2,4-oxadiazol-5-yl]-piperidin-1-yl}-(3-methyl-thiophen-2-yl)-methanone

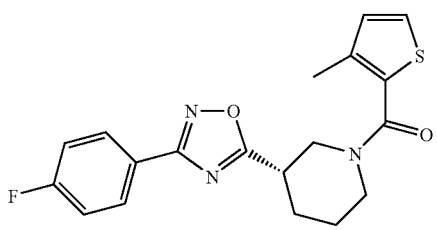

The compound was prepared following the procedure described in the Example 13, using 3-methyl-thiophene-2-carbonyl chloride as the acyl chloride of choice and S-3-[3-(4-fluoro-phenyl)-[1,2,4]oxadiazol-5-yl]-piperidine hydrochloride (prepared as described in the Example 12).

Yield: 54% (white solid); mp=90-92° C.; [α]$_D^{20}$=+75° (c=0.95, CHCl₃); LCMS (Tr): 5.58 min (Method A); MS (ES+) gave m/z: 372.2.

¹H-NMR (CDCl₃, 300 MHz), δ (ppm): 8.06 (dd, 2H); 7.27 (d, 1H); 7.15 (dd, 2H); 6.83 (d, 1H); 4.49 (m, 1H); 4.10 (m, 1H); 3.47 (dd, 1H); 3.30-3.15 (m, 2H); 2.33 (m, 1H); 2.27 (s, 3H); 2.04-1.85 (m, 2H); 1.80-1.62 (m, 1H).

Example 33

{(S)-3-[3-(4-Fluoro-phenyl)-1,2,4-oxadiazol-5-yl]-piperidin-1-yl}-(1-methyl-1H-pyrrol-2-yl)-methanone

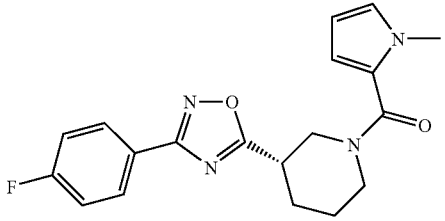

The compound was prepared following the procedure described in the Example 13, using 1-methyl-1H-pyrrole-2-carbonyl chloride as the acyl chloride of choice and S-3-[3-(4-fluoro-phenyl)-[1,2,4]oxadiazol-5-yl]-piperidine hydrochloride (prepared as described in the Example 12).

Yield: 64% (beige powder); mp=84-85° C.; [α]$_D^{20}$=+101° (c=1.2, CHCl₃); LCMS (Tr): 5.53 min (Method A); MS (ES+) gave m/z: 355.2.

¹H-NMR (CDCl₃, 300 MHz), δ (ppm): 8.06 (dd, 2H); 7.16 (dd, 2H); 6.70 (dd, 1H); 6.37 (dd, 1H); 6.09 (dd; 1H); 4.69 (m, 1H); 4.32 (m, 1H); 3.77 (s, 3H); 3.52 (dd, 1H); 3.24 (m, 2H); 3.34 (m, 1H); 2.08-1.86 (m, 2H); 1.77-1.61 (m, 1H).

Example 34

Cyclopentyl-{(S)-3-[3-(4-fluoro-phenyl)-[1,2,4]oxadiazol-5-yl]-piperidin-1-yl}-methanone

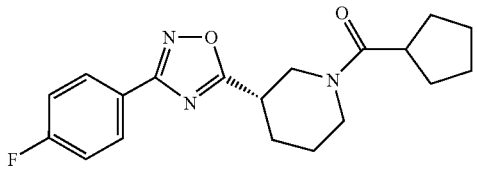

The compound was prepared following the procedure described in the Example 13, using cyclopentane-carbonyl chloride as the acyl chloride of choice and S-3-[3-(4-fluoro-phenyl)-[1,2,4]oxadiazol-5-yl]-piperidine hydrochloride (prepared as described in the Example 12).

Yield: 91% (thick oil); [α]$_D^{20}$=+95° (c=1.2, CHCl₃); LCMS (Tr): 7.41 min (Method A); MS (ES+) gave m/z: 344.2.

¹H-NMR (CDCl₃, 343 K, 300 MHz), δ (ppm): 8.07 (dd, 2H); 7.15 (dd, 2H); 4.48 (m, 1H); 4.08 (m, 1H); 3.38 (m, 1H); 3.21-3.07 (m, 2H); 2.96 (m, 1H); 2.36-2.24 (m, 1H); 2.05-1.51 (m, 11H).

Example 35

(3,4-Difluoro-phenyl)-{(S)-3-[3-(4-fluoro-phenyl)-[1,2,4]oxadiazol-5-yl]-piperidin-1-yl}-methanone

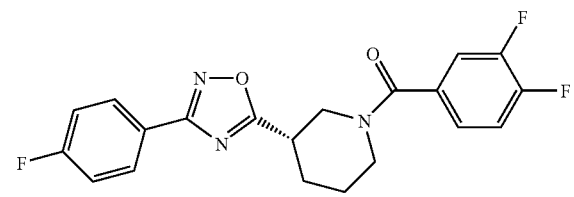

The compound was prepared following the procedure described in the Example 13, using 3,4-difluoro-benzoyl chloride as the acyl chloride of choice and S-3-[3-(4-fluoro-phenyl)-[1,2,4]oxadiazol-5-yl]-piperidine hydrochloride (prepared as described in the Example 12).

Yield: 59% (white solid); mp=120-121° C.; [α]$_D^{20}$=+105° (c=1.0, CHCl₃); LCMS (Tr): 7.6 min (Method A); MS (ES+) gave m/z: 388.0.

¹H-NMR (CDCl₃, 333K, 300 MHz), δ (ppm): 8.06 (dd, 2H); 7.28 (m, 1H); 7.22-7.11 (m, 4H); 4.36 (d br, 1H); 2.92 (d br, 1H); 3.57 (dd, 1H); 3.37-3.19 (m, 2H); 2:33 (m, 1H); 2.12-1.86 (m, 2H); 1.68 (m, 1H).

Example 36

Benzothiazol-6-yl-{(S)-3-[3-(4-fluoro-phenyl)-1,2,4-oxadiazol-5-yl]-piperidin-1-yl}-methanone

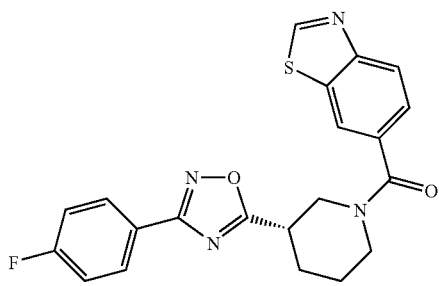

A mixture of S-3-[3-(4-fluoro-phenyl)-[1,2,4]oxadiazol-5-yl]-piperidine hydrochloride (100 mg, 0.35 mmol, already prepared before in the Example 12), benzothiazole-6-carboxylic acid (70 mg, 0.38 mmol), HOAT (72 mg, 0.52 mmol), PS-DCC (ex Argonaut Technologies, 0.59 g, 0.70 mmol, loading=1.2 mmol/g) and DIEA (90 mL, 0.52 mmol) in dry dichloromethane (6 mL) was kept overnight under orbital shaking (IKA Vibrax VXR). The resin was filtered off and washed repeatedly with dichloromethane; the filtrate was washed with HCl 1N (10 mL×2 times) and with $K_2CO_3$ 5% (aq.) (10 mL×2 times), then was dried over sodium sulphate and evaporated under reduced pressure. The crude was purified by flash chromatography (silica gel, eluent: DCM/MeOH 95/5) to give 50 mg of benzothiazol-6-yl-{(S)-3-[3-(4-fluoro-phenyl)-1,2,4-oxadiazol-5-yl]-piperidin-1-yl}-methanone.

Yield: 35% (white powder); mp=63-64° C.; $[\alpha]_D^{20}$=+105° (c=1.0, CHCl$_3$); LCMS (Tr): 5.39 min (Method A); MS (ES+) gave m/z: 409.1.

$^1$H-NMR (CDCl$_3$, 300 MHz), δ (ppm): 9.08 (s, 1H); 8.17 (d, 1H); 8.07 (d, 1H); 8.05 (m, 2H); 7.57 (dd, 1H); 7.16 (dd, 2H); 5.00-3.71 (m br, 2H); 3.58 (m, 1H); 3.31 (m, 2H); 2.35 (m, 1H); 2.10-1.87 (m, 2H); 1.72 (m, 1H).

Example 37

{(S)-3-[3-(4-Fluoro-phenyl)-1,2,4-oxadiazol-5-yl]-piperidin-1-yl}-thiazol-2-yl-methanone

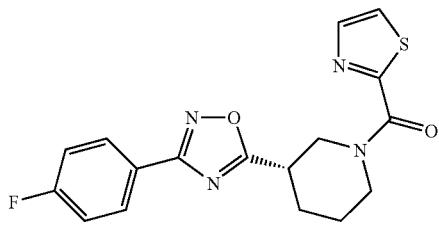

The compound was prepared following the procedure described in the Example 36, using 2-thiazolecarboxylic acid as the acid of choice and S-3-[3-(4-fluoro-phenyl)-[1,2,4]oxadiazol-5-yl]-piperidine hydrochloride (prepared as described in the Example 12).

Yield: 55% (off-white powder); mp=94-95° C.; $[\alpha]_D^{20}$=+127° (c=0.9, CHCl$_3$); LCMS (Tr): 5.54 min (Method A); MS (ES+) gave m/z: 359.1.

$^1$H-NMR (CDCl$_3$, 300 MHz), δ (ppm): 8.05 (m br, 2H); 7.89 (m br, 1H); 7.53 (m br, 1H); 7.15 (dd, 2H); 5.41, 4.94, 4.38, 4.04 and 3.44 (m br, 3H); 3.34 (m br, 2H); 2.36 (m, 1H); 2.13-1.92 (m br, 2H); 1.78 (m, 1H).

Example 38

{(S)-3-[3-(4-Fluoro-phenyl)-1,2,4-oxadiazol-5-yl]-piperidin-1-yl}-(4-methyl-thiazol-5-yl)-methanone

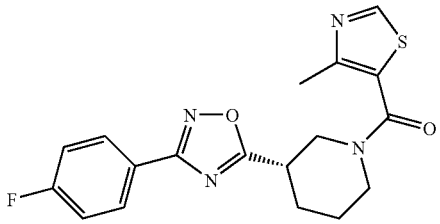

The compound was prepared following the procedure described in the Example 36, using 4-methyl-thiazole-5-carboxylic acid as the acid of choice and S-3-[3-(4-fluoro-phenyl)-[1,2,4]oxadiazol-5-yl]-piperidine hydrochloride (prepared as described in the Example 12).

Yield: 76% (yellow powder); mp=122-124° C.; $[\alpha]_D^{20}$=+101° (c=0.55, CHCl$_3$); LCMS (Tr): 5.08 min (Method A); MS (ES+) gave m/z: 373.1.

$^1$H-NMR (CDCl$_3$, 300 MHz), δ (ppm): 8.75 (s, 1H); 8.06 (dd, 2H); 7.16 (dd, 2H); 4.42 (m, 1H); 3.97 (m, 1H); 3.56 (dd, 1H); 3.35-3.19 (m, 2H); 2.50 (s, 3H); 2.34 (m, 1H); 2.08-1.88 (m, 2H); 1.70 (m, 1H).

Example 39

{(S)-3-[3-(4-Fluoro-phenyl)-1,2,4-oxadiazol-5-yl]-piperidin-1-yl}-(6-morpholin-4-yl-pyridin-3-yl)-methanone

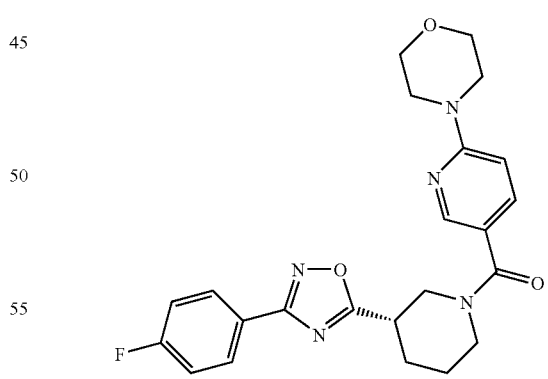

The compound was prepared following the procedure described in the Example 36, using 6-morpholinonicotinic acid as the acid of choice and S-3-[3-(4-fluoro-phenyl)-[1,2,4]oxadiazol-5-yl]-piperidine hydrochloride (prepared as described in the Example 12).

Yield: 20% (off-white powder); mp=112-114° C.; $[\alpha]_D^{20}$=+101° (c=0.55, CHCl$_3$); LCMS (Tr): 4.96 min (Method A); MS (ES+) gave m/z: 438.2.

¹H-NMR (CDCl₃, 300 MHz), δ (ppm): 8.31 (d, 1H); 8.06 (dd, 2H); 7.65 (dd, 1H); 7.16 (dd, 2H); 6.63 (d, 1H); 4.51 (m, 1H); 4.11 (m, 1H); 3.81 (dd, 4H); 3.59 (dd, 4H); 3.50 (m, 1H); 3.24 (m, 2H); 2.35 (m, 1H); 2.05-1.86 (m, 2H); 1.69 (m, 1H).

Example 40

{(S)-3-[3-(4-Fluoro-phenyl)-1,2,4-oxadiazol-5-yl]-piperidin-1-yl}-1H-indol-5-yl)-methanone

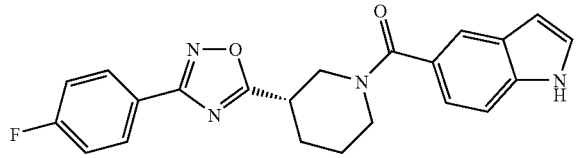

The compound was prepared following the procedure described in the Example 36, using indole-5-carboxylic acid as the acid of choice and S-3-[3-(4-fluoro-phenyl)-[1,2,4]oxadiazol-5-yl]-piperidine hydrochloride (prepared as described in the Example 12).

Yield: 44% (white solid); mp=191-192° C.; [α]$_D^{20}$+107° (c=0.85, CHCl₃); LCMS (Tr): 5.44 min Method A); MS (ES+) gave m/z: 391.2.

¹H-NMR (CDCl₃, 333K, 300 MHz), δ (ppm): 8.19 (s br, 1H); 8.06 (dd, 2H); 7.75 (s br, 1H); 7.39 (d, 1H); 7.28 (dd, 1H); 7.24 (m, 1H); 7.14 (dd, 2H); 6.59 (m, 1H); 4.56 (m, 1H); 4.15 (m, 1H); 3.50 (dd, 1H); 3.33-3.18 (m, 2H); 2.34 (m, 1H); 2.07-1.85 (m, 2H); 1.73 (m, 1H).

Example 41

2-(4-Fluoro-phenyl)-1-{(S)-3-[3-(4-fluoro-phenyl)-1,2,4-oxadiazol-5-yl]-piperidin-1-yl}-ethanone

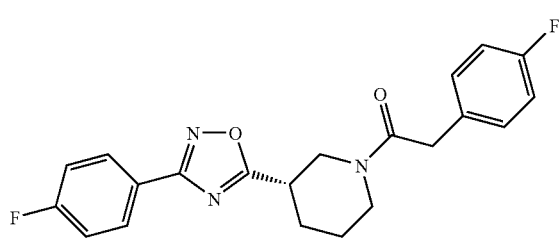

The compound was prepared following the procedure described in the Example 36, using 4-fluorophenylacetic acid as the acid of choice and S-3-[3-(4-fluoro-phenyl)-[1,2,4]oxadiazol-5-yl]-piperidine hydrochloride (prepared as described in the Example 12).

Yield: 37% (transparent oil); [α]$_D^{20}$=+68° (c=0.6, CHCl₃); LCMS (Tr): 5.58 min (Method A); MS (ES+) gave m/z: 384.2.

¹H-NMR (CDCl₃, 333K, 300 MHz), δ (ppm): 8.06 (dd, 2H); 7.22 (dd, 2H); 7.16 (dd, 2H); 6.99 (dd, 2H); 4.65, 4.03, 3.47 and 3.00 (m br, 4H); 3.75 (s, 2H); 3.19 (ddd, 1H); 2.23 (m, 1H); 1.97 (m, 1H); 1.79 (m, 1H); 1.49 (m, 1H).

Example 42

3-(4-Fluoro-phenyl)-1-{(S)-3-[3-(4-fluoro-phenyl)-1,2,4-oxadiazol-5-yl]-piperidin-1-yl}-propan-1-one

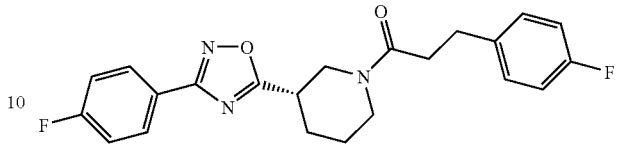

The compound was prepared following the procedure described in the Example 36, using 3-(4-fluorophenyl)propionic acid as the acid of choice and S-3-[3-(4-fluoro-phenyl)-[1,2,4]oxadiazol-5-yl]-piperidine hydrochloride (prepared as described in the Example 12).

Yield: 50% (white powder); mp=83-84° C.; [α]$_D^{20}$=+80° (c=1.32, CHCl₃); LCMS (Tr): 5.68 min (Method A); MS (ES+) gave m/z: 398.4.

¹H-NMR (CDCl₃, 333K, 300 MHz), δ (ppm): 8.06 (dd, 2H); 7.17 (dd, 2H); 7.15 (dd, 2H); 6.95 (dd, 2H); 4.71, 3.93 and 3.44 (m br, 2H); 3.17 (m, 1H); 3.06 (m br, 1H); 2.98 (dd, 2H); 2.67 (dd, 2H); 2.26 (m, 1H); 1.97 (m, 1H); 1.83 (m, 1H); 1.55 (m, 1H).

Example 43

{(S)-3-[3-(4-Fluoro-phenyl)-1,2,4-oxadiazol-5-yl]-piperidin-1-yl}-isoquinolin-3-yl-methanone

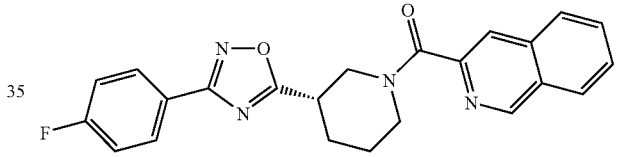

The compound was prepared following the procedure described in the Example 36, using isoquinoline-3-carboxylic acid as the acid of choice and S-3-[3-(4-fluoro-phenyl)-[1,2,4]oxadiazol-5-yl]-piperidine hydrochloride (prepared as described in the Example 12).

Yield: 56% (white oil); [α]$_D^{20}$=+150° (c=0.8, CHCl₃); LCMS (Tr): 5.59 min (Method A); MS (ES+) gave m/z: 403.2.

¹H-NMR (CDCl₃, 333K, 300 MHz), δ (ppm): 8.23 (d, 1H); 8.12 (d, 1H); 8.02 (m br, 2H); 7.84 (d, 1H); 7.76 (d, 1H); 7.74 (m, 1H); 7.59 (dd, 1H); 7.13 (dd br, 2H); 5.01, 4.51 and 4.18 (m br, 2H); 3.77-3.26 (m br, 3H); 2.39 (m, 1H); 2.18-1.78 (m br, 3H).

Example 44

{(S)-3-[3-(4-Fluoro-phenyl)-1,2,4-oxadiazol-5-yl]-piperidin-1-yl}-quinoxalin-6-yl-methanone

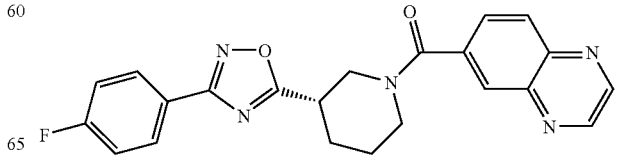

The compound was prepared following the procedure described in the Example 36, using 6-quinoxalinecarboxylic acid as the acid of choice and S-3-[3-(4-fluoro-phenyl)-[1,2,4]oxadiazol-5-yl]-piperidine hydrochloride (prepared as described in the Example 12). {(S)-3-[3-(4-Fluoro-phenyl)-1,2,4-oxadiazol-5-yl]-piperidin-1-yl}-quinoxalin-6-yl-methanone was obtained pure after purification through a silica gel cartridge (eluent: DCM/MeOH/NH$_4$OH 98/2/0.2).

Yield: 83% (white solid); $[\alpha]_D^{20}$=+120° (c=1.0, CHCl$_3$); LCMS (Tr): 7.0 min (method A); MS (ES+) gave m/z: 404.0.

$^1$H-NMR (CDCl$_3$, 330 K, 300 MHz), δ (ppm): 8.88 (s, 2H); 8.18 (dd, 2H); 8.06 (m, 2H); 7.82 (dd, 1H); 7.15 (dd, 2H); 4.47 (m br, 1H); 4.02 (m br, 1H); 3.65 (dd, 1H); 3.44-3.23 (m, 2H); 2.36 (m, 1H); 2.14-1.88 (m, 2H); 1.74 (m, 1H).

Example 45

{(S)-3-[3-(4-Fluoro-phenyl)-1,2,4-oxadiazol-5-yl]-piperidin-1-yl}-benzoimidazol-6-yl-methanone

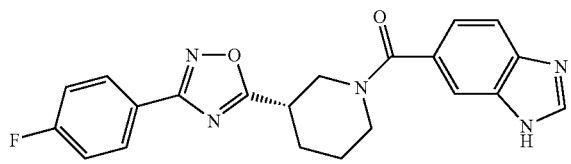

The compound was prepared following the procedure described in the Example 36, using benzimidazole-5-carboxylic acid as the acid of choice and S-3-[3-(4-fluoro-phenyl)-[1,2,4]oxadiazol-5-yl]-piperidine hydrochloride (prepared as described in the Example 12). {(S)-3-[3-(4-Fluoro-phenyl)-1,2,4-oxadiazol-5-yl]-piperidin-1-yl}-benzoimidazol-6-yl-methanone was obtained pure after purification by flash chromatography (silica gel, eluent: DCM/MeOH/NH$_4$OH 98/2/0.2).

Yield: 5% (white solid); mp=110-115° C.; $[\alpha]_D^{20}$=+115° (c=1.0, CHCl$_3$); LCMS (Tr): 6.28 min (Method A); MS (ES+) gave m/z: 392.0.

$^1$H-NMR (CDCl$_3$, 300 MHz), δ (ppm): 9.56 and 8.38 (s, 1H); 8-11-7.97 (m, 4H); 7.97-7.82 (m, 1H); 7.60-7.46 (m, 1H); 7.13 (m, 2H); 4.42 (m br, 1H); 3.97 (m, 1H); 3.59 (m, 1H); 3.31 (m, 2H); 2.34 (m, 1H); 2.11-1.84 (m, 2H); 1.72 (m, 1H).

Example 46

(4-Fluoro-phenyl)-{(S)-3-[3-(2,4,6-trifluoro-phenyl)-[1,2,4]oxadiazol-5-yl]-piperidin-1-yl}-methanone

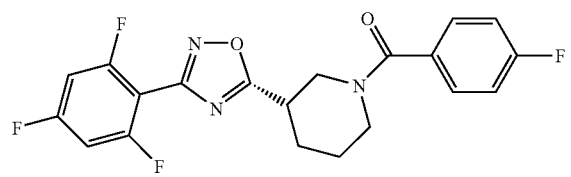

46(A) S-3-[3-(2,4,6-Trifluoro-phenyl)-[1,2,4]oxadiazol-5-yl]-piperidine-1-carboxylic acid tert-butyl ester To a solution of 2,4,6-trifluorobenzonitrile (1.5 g, 9.6 mmol) in EtOH (5 mL), hydroxylamine (50% wt. aqueous solution, 2.5 mL, 38 mmol) was added at room temperature and the solution was stirred under reflux for 1 h. The solvent was removed under reduced pressure to afford N-hydroxy-2,4,6-trifluoro-benzamidine that was used immediately for the next step.

A mixture of N-hydroxy-2,4,6-trifluoro-benzamidine (9.6 mmol), S-1-Boc-piperidine-3-carboxylic acid (2.3 g, 9.6 mmol), EDCI.HCl (2.87 g, 15 mmol), HOBT (1.35 g, 9.6 mmol) and DIEA (3.4 mL, 20 mmol) in dioxane (10 mL) was stirred overnight at room temperature, under nitrogen atmosphere. Another portion of HOBT (1.35 g), EDCI.HCl (2.87 g) and DIEA (3.4 mL) was added and the reaction mixture was heated at 60° C. for 2 h. Then, the reaction mixture was refluxed for 18 h and the solvent was evaporated under reduced pressure. The residue was diluted with water (50 mL) and ethyl acetate (50 mL), the phases were separated and the organic layer was washed sequentially with water (50 mL×2 times) and with NaOH 1N (50 mL×2 times). The organic layer was dried over Na$_2$SO$_4$ and concentrated under reduced pressure. Purification of the crude by flash chromatography (silica gel, eluent: DCM/hexane/MeOH 50/50/0.2) gave 0.7 g of S-3-[3-(2,4,6-trifluoro-phenyl)-[1,2,4]oxadiazol-5-yl]-piperidine-1-carboxylic acid tert-butyl ester.

Yield: 20%; LCMS (Tr): 10.10 min (Method B); MS (ES+) gave m/z: 384.4.

$^1$H-NMR (CDCl$_3$, 300 MHz, 333 K), δ (ppm): 6.80 (m, 2H); 4.29 (d br, 1H); 3.93 (ddd, 1H); 3.32 (dd, 1H); 3.19 (tt, 1H); 3.02 (ddd, 1H); 2.26 (m, 1H); 1.99-1.79 (m, 2H); 1.70-1.56 (m, 1H); 1.47 (s, 9H).

46(B) S-3-[3-(2,4,6-Trifluoro-phenyl)-[1,2,4]oxadiazol-5-yl]-piperidine hydrochloride S-3-[3-(2,4,6-Trifluoro-phenyl)-[1,2,4]oxadiazol-5-yl]-piperidine-1-carboxylic acid tert-butyl ester (0.2 g, 0.52 mmol) was dissolved in dichloromethane (3 mL) and 5 mL of HCl 4N (dioxane solution) were added dropwise. The resulting mixture was stirred at room temperature for 2 h. The solvent was evaporated under reduced pressure to afford 165 mg (yield: 100%) of S-3-[3-(2,4,6-trifluoro-phenyl)-[1,2,4]oxadiazol-5-yl]-piperidine hydrochloride as a white solid. LCMS (Tr): 4.80 min (Method B); MS (ES+) gave m/z: 284.4.

46(C) (4-Fluoro-phenyl)-{(S)-3-[3-(2,4,6-trifluoro-phenyl)-[1,2,4]oxadiazol-5-yl]-piperidin-1-yl}-methanone To a suspension of S-3-[3-(2,4,6-trifluoro-phenyl)-[1,2,4]oxadiazol-5-yl]-piperidine hydrochloride (165 mg, 0.52 mmol) in dry dichloromethane (3 mL), triethylamine (154 mL, 1.09 mmol) and 4-fluorobenzoyl chloride (62 mL, 0.52 mmol) were added dropwise at 0° C. The reaction mixture was allowed to warm at room temperature and stirred overnight under nitrogen atmosphere. The solution was then treated with HCl 0.5N (5 mL) and the phases were separated. The organic layer was washed subsequently with HCl 0.5N (5 mL), NaOH 1N (5 mL) and water (5 mL), then was dried over Na$_2$SO$_4$ and evaporated under reduced pressure. The crude was purified by flash chromatography (silica gel, eluent: hexane/ethyl acetate 8:2) to give 50 mg of the title compound. Further purification by preparative HPLC (column: SymmetryPrep C18, 7 uM, 19×300 mm; mobile phase A: water/acetonitrile/TFA 900/100/0.5, mobile phase B: water/acetonitrile/TFA 100/900/0.5, flow: 20 mL/min) afforded 25 mg of (4-fluoro-phenyl)-{(S)-3-[3-(2,4,6-trifluoro-phenyl)-[1,2,4]oxadiazol-5-yl]-piperidin-1-yl}-methanone.

Yield: 12% (thick oil); LCMS (Tr): 7.0 min (Method A); MS (ES+) gave m/z: 406.0.

¹H-NMR (CDCl₃, 333K, 300 MHz), δ (ppm): 7.45 (m 2H); 7.18-7.00 (m, 2H), 6.90-6.75 (m, 2H); 4.40 (d br, 1H); 3.95 (d br, 1H); 3.52 (dd, 1H); 3.37-3.20 (m, 2H); 2.40-2.20 (m, 1H); 2.15-1.85 (m, 2H); 1.78-1.55 (m, 1H).

Example 47

(4-Fluoro-phenyl)-[(S)-3-(3-pyridin-3-yl-[1,2,4]oxadiazol-5-yl)-piperidin-1-yl]-methanone

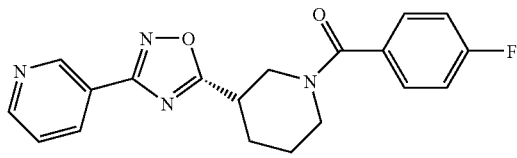

47(A) S-3-(3-Pyridin-3-yl-[1,2,4]oxadiazol-5-yl)-piperidine-1-carboxylic acid tert-butyl ester The compound was prepared following the procedure described in the Example 46(A), starting from 3-cyanopyridine. S-3-(3-Pyridin-3-yl-[1,2,4]oxadiazol-5-yl)-piperidine-1-carboxylic acid tert-butyl ester was obtained pure after trituration from diethylether/pentane 1:1 (Yield: 29%).

LCMS (Tr): 6.49 min (Method A); MS (ES+) gave m/z: 331.1.

¹H-NMR (CDCl₃, 333K, 300 MHz), δ (ppm): 9.32 (d, 1H); 8.74 (dd, 1H); 8.37 (ddd, 1H); 7.43 (dd, 1H); 4.28 (d br, 1H); 3.93 (ddd, 1H); 3.34 (dd, 1H); 3.18 (tt, 1H); 3.05 (ddd, 1H); 2.27 (m, 1H); 2.00-1.81 (m, 2H); 1.68-1.57 (m, 1H).

47(B) S-3-(5-Piperidin-3-yl-[1,2,4]oxadiazol-3-yl)-pyridine dihydrochloride

The compound was prepared following the procedure described in the Example 46(B), starting from S-3-(3-pyridin-3-yl-[1,2,4]oxadiazol-5-yl)-piperidine-1-carboxylic acid tert-butyl ester (yield: 100%).

LCMS (Tr): 1.78 min (Method B); MS (ES+) gave m/z: 231.1.

47(C) (4-Fluoro-phenyl)-[(S)-3-(3-pyridin-3-yl-[1,2,4]oxadiazol-5-yl)-piperidin-1-yl]-methanone The compound was prepared following the procedure described in the Example 46(C), staring from S-3-(5-piperidin-3-yl-[1,2,4]oxadiazol-3-yl)-pyridine dihydrochloride and using 4-fluorobenzoyl chloride as the acyl chloride of choice. (4-Fluoro-phenyl)-[(S)-3-(3-pyridin-3-yl-[1,2,4]oxadiazol-5-yl)-piperidin-1-yl]-methanone was obtained pure after purification by flash chromatography (silica gel, eluent: DCM/MeOH/NH₄OH 99/1/0.1).

Yield: 98% (white gummy solid); [α]_D^20=+105° (c=1.05, CHCl₃); LCMS (Tr): 5.8 min (Method A); MS (ES+) gave m/z: 353.0.

¹H-NMR (CDCl₃, 333K, 300 MHz), δ (ppm): 9.30 (s, 1H); 8.8 (d, 1H); 8.3 (m, 1H); 7.55-7.35 (m, 3H); 7.20-7.0 (m, 2H); 4.50 (d br, 1H); 4.0 (d br, 1H); 3.50 (dd, 1H); 3.35-3.15 (m, 2H); 2.45 (m, 1H); 2.15-1.80 (m, 2H); 1.80-1.60 (m, 1H).

Example 48

(4-Fluoro-phenyl)-[(S)-3-(3-pyridin-4-yl-[1,2,4]oxadiazol-5-yl)-piperidin-1-yl]-methanone

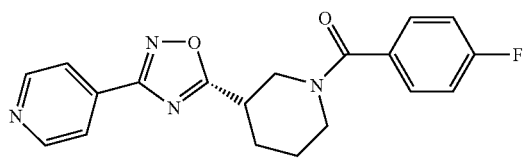

48(A) S-3-(3-Pyridin-4-yl-[1,2,4]oxadiazol-5-yl)-piperidine-1-carboxylic acid tert-butyl ester The compound was prepared following the procedure described in the Example 46(A), starting from 4-cyanopyridine. S-3-(3-Pyridin-4-yl-[1,2,4]oxadiazol-5-yl)-piperidine-1-carboxylic acid tert-butyl ester was obtained pure after trituration from hexane/diethyl ether 1:1 (Yield: 68%).

LCMS (Tr): 6.56 min (Method A); MS (ES+) gave m/z: 331.1.

48(B) S-4-(5-Piperidin-3-yl-[1,2,4]oxadiazol-3-yl)-pyridine dihydrochloride

The compound was prepared following the procedure described in the Example 46(B), starting from S-3-(3-Pyridin-4-yl-[1,2,4]oxadiazol-5-yl)-piperidine-1-carboxylic acid tert-butyl ester (yield: 100%).

LCMS (Tr): 1.44 min (Method B); MS (ES+) gave m/z: 231.1

48(C) (4-Fluoro-phenyl)-[(S)-3-(3-pyridin-4-yl-[1,2,4]oxadiazol-5-yl)-piperidin-1-yl]-methanone The compound was prepared following the procedure described in the Example 46(C), starting from S-4-(5-Piperidin-3-yl-[1,2,4]oxadiazol-3-yl)-pyridine dihydrochloride and using 4-fluorobenzoyl chloride as the acyl chloride of choice. (4-Fluoro-phenyl)-[(S)-3-(3-pyridin-4-yl-[1,2,4]oxadiazol-5-yl)-piperidin-1-yl]-methanone was obtained pure after purification by flash chromatography (2 successive columns were necessary under the following conditions: silica gel, eluent: DCM/MeOH/NH₄OH 99/1/0.1).

Yield: 38% (white solid); mp=113-115° C.; [α]_D^20=+112° (c=1.62, CHCl₃); LCMS (Tr): 5.55 min (Method A); MS (ES+) gave m/z: 353.0.

¹H-NMR (CDCl₃, 333K, 300 MHz), δ (ppm): 8.79 (m, 2H); 7.99 (m, 2H); 7.43 (dd, 2H); 7.10 (dd, 2H); 4.45 (d br, 1H); 3.97 (m, 1H); 3.54 (dd, 1H); 3.35-3.21 (m, 2H); 2.35 (m, 1H); 2.11-1.86 (m, 2H); 1.70 (m, 1H).

Example 49

{(S)-3-[3-(2,4-Difluoro-phenyl)-[1,2,4]oxadiazol-5-yl]-piperidin-1-yl}-(4-fluoro-phenyl)-methanone

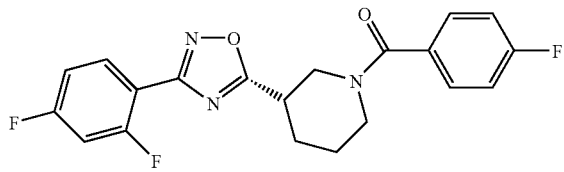

49(A) S-3-[3-(2,4-Difluoro-phenyl)-[1,2,4]oxadiazol-5-yl]-piperidine-1-carboxylic acid tert-butyl ester To a mixture of 2,4-difluorobenzonitrile (1.39 g, 10 mmol) and DIEA (5.13 ml, 30 mmol) in EtOH (15 ml) was added 2.12 g of hydroxylamine hydrochloride (30 mmol) and the reaction was heated at 70° C. for 48 h. Half of the solvent was removed under reduced pressure. The mixture was poured in DCM (100 ml) and water (30 ml). 2.5 ml of NaOH 1N was added until pH=9-10. The organic layer was separated and the aqueous phase was extracted with DCM. The organic layers were combined, washed with water, dried over MgSO$_4$, filtered and evaporated under reduced pressure to afford N-hydroxy-2,4-difluoro-benzamidine which was used without further purification for the next step.

A mixture of N-hydroxy-2,4-difluoro-benzamidine (10 mmol), S-1-Boc-piperidine-3-carboxylic acid (2.3 g, 10 mmol), EDCI.HCl (2.87 g, 15 mmol), HOBT (1.35 g, 10 mmol) and DIEA (3.4 mL, 20 mmol) in dioxane (10 mL) was stirred overnight at room temperature, under nitrogen atmosphere. Then, the reaction mixture was refluxed for 18 h and the solvent was evaporated under reduced pressure. The residue was diluted with water (50 mL) and ethyl acetate (50 mL), the phases were separated and the organic layer was washed sequentially with water (50 mL×2 times) and with NaOH 1N (50 mL×2 times). The organic layer was dried over Na$_2$SO$_4$ and concentrated under reduced pressure. Purification of the crude by flash chromatography (silica gel, eluent: DCM/hexane/MeOH 50/50/0.2) gave 2.4 g of S-3-[3-(2,4-difluoro-phenyl)-[1,2,4]oxadiazol-5-yl]-piperidine-1-carboxylic acid tert-butyl ester.

Yield: 66%; LCMS (Tr): 7.93 min (Method A); MS (ES+) gave m/z: 366.2.

$^1$H-NMR (CDCl$_3$, 333K, 300 MHz), δ (ppm): 8.05 (m, 1H); 6.98 (m, 2H); 4.27 (d br, 1H); 3.92 (m, 1H); 3.31 (dd, 1H); 3.17 (tt, 1H); 3.03 (ddd, 1H); 2.25 (m, 1H); 1.95-1.78 (m, 2H); 1.77-1.53 (m, 1H); 1.46 (s, 9H).

49(B) S-3-[3-(2,4-Difluoro-phenyl)-[1,2,4]oxadiazol-5-yl]-piperidine hydrochloride S-3-[3-(2,4-Difluoro-phenyl)-[1,2,4]oxadiazol-5-yl]-piperidine-1-carboxylic acid tert-butyl ester (0.22 g, 0.6 mmol) was dissolved in dichloromethane (3 mL) and 5 mL of HCl 4N (dioxane solution) were added dropwise. The resulting mixture was stirred at room temperature for 2 h. The solvent was evaporated under reduced pressure to afford 180 mg (yield: 100%) of S-3-[3-(2,4-difluoro-phenyl)-[1,2,4]oxadiazol-5-yl]-piperidine hydrochloride as a white solid.

LCMS (Tr): 4.67 min (Method B); MS (ES+) gave m/z: 266.2.

49(C) {(S)-3-[3-(2,4-Difluoro-phenyl)-[1,2,4]oxadiazol-5-yl]-piperidin-1-yl}-(4-fluoro-phenyl)-methanone To a suspension of S-3-[3-(2,4-difluoro-phenyl)-[1,2,4]oxadiazol-5-yl]-piperidine hydrochloride (180 mg, 0.6 mmol) in dry dichloromethane (5 mL), triethylamine (180 mL, 1.26 mmol) and 4-fluorobenzoyl chloride (71 mL, 0.6 mmol) were added dropwise at 0° C. The reaction mixture was allowed to warm at room temperature and stirred overnight under nitrogen atmosphere. The solution was then treated with HCl 0.5N (5 mL) and the phases were separated. The organic layer was washed subsequently with HCl 0.5N (5 mL), NaOH 1N (5 mL) and water (5 mL), then was dried over Na$_2$SO$_4$ and evaporated under reduced pressure. The crude was purified by flash chromatography (silica gel, eluent: DCM/hexane/MeOH 50/50/0.2) to give 50 mg of the title compound.

Yield: 86% (white gummy solid); [α]$_D^{20}$=+106° (c=1.05, CHCl$_3$); LCMS (Tr): 7.13 min (Method A); MS (ES+) gave m/z: 388.0.

$^1$H-NMR (CDCl$_3$, 333K, 300 MHz), δ (ppm): 8.00 (m, 1H); 7.50-7.35 (m, 2H); 7.15-6.90 (m, 4H); 4.4 (d br, 1H); 3.95 (d br, 1H); 3.50 (dd, 1H); 3.35-3.15 (m, 2H); 2.40-2.20 (m, 1H); 2.10-1.80 (m, 2H); 1.80-1.60 (m, 1H).

Example 50

(4-Fluoro-phenyl)-[(S)-3-(3-naphthalen-1-yl-[1,2,4]oxadiazol-5-yl)-piperidin-1-yl]-methanone

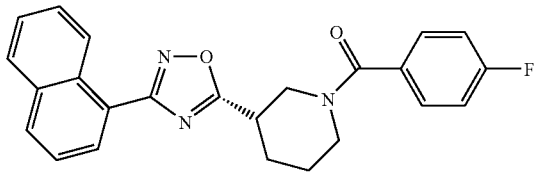

50(A) S-3-(3-Naphthalen-1-yl-[1,2,4]oxadiazol-5-yl)-piperidine-1-carboxylic acid tert-butyl ester The compound was prepared following the procedure described in the Example 49(A), starting from 1-cyanonaphtalene. S-3-(3-Naphthalen-1-yl-[1,2,4]oxadiazol-5-yl)-piperidine-1-carboxylic acid tert-butyl ester was obtained pure after trituration from diethylether/hexane 1:1 and successive flash chromatography (silica gel, eluent: DCM/MeOH 99.8/0.2) (Yield: 66%).

LCMS (Tr): 8.64 min (Method A); MS (ES+) gave m/z: 380.1.

50(B) S-3-(3-Naphthalen-1-yl-[1,2,4]oxadiazol-5-yl)-piperidine hydrochloride The compound was prepared following the procedure described in the Example 49(B), starting from S-3-(3-naphthalen-1-yl-[1,2,4]oxadiazol-5-yl)-piperidine-1-carboxylic acid tert-butyl ester (yield: 100%).

LCMS (Tr): 5.42 min (Method B); MS (ES+) gave m/z: 280.1.

50(C) (4-Fluoro-phenyl)-[(S)-3-(3-naphthalen-1-yl-[1,2,4]oxadiazol-5-yl)-piperidin-1-yl]-methanone The compound was prepared following the procedure described in the Example 49(C), starting from S-3-(3-naphthalen-1-yl-[1,2,4]oxadiazol-5-yl)-piperidine hydrochloride and using 4-fluorobenzoyl chloride as the acyl chloride of choice. (4-Fluoro-phenyl)-[(S)-3-(3-naphthalen-1-yl-[1,2,4]oxadiazol-5-yl)-piperidin-1-yl]-methanone was obtained pure after flash chromatography (silica gel, eluent: DCM/hexane/MeOH 50/50/0.2).

Yield: 83% (white gummy solid); $[\alpha]_D^{20}$=+88° (c=1.28, CHCl$_3$); LCMS (Tr): 7.6 min (Method A); MS (ES+) gave m/z: 402.1.

$^1$H-NMR (CDCl$_3$, 333K, 300 MHz), δ (ppm): 8.90 (d, 1H); 8.20 (d, 1H); 7.90 (dd, 2H); 7.60-7.40 (m, 5H); 7.15-7.00 (m, 2H); 4.50 (d br, 1H); 4.00 (d br, 1H); 3.60 (dd, 1H); 3.40-3.15 (m, 2H); 2.45-2.30 (m, 1H); 2.20-1.85 (m, 2H); 1.80-1.60 (m, 1H).

Example 51

{(S)-3-[3-(2,6-Difluoro-phenyl)-[1,2,4]oxadiazol-5-yl]-piperidin-1-yl}-(4-fluoro-phenyl)-methanone

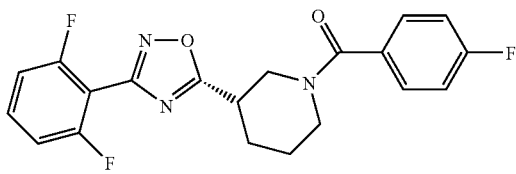

51(A) S-3-[3-(2,6-Difluoro-phenyl)-[1,2,4]oxadiazol-5-yl]-piperidine-1-carboxylic acid tert-butyl ester The compound was prepared following the procedure described in the Example 49(A), starting from 2,6-difluorobenzonitrile. S-3-[3-(2,6-difluoro-phenyl)-[1,2,4]oxadiazol-5-yl]-piperidine-1-carboxylic acid tert-butyl ester was obtained pure after flash chromatography (silica gel, eluent: DCM/MeOH 99.8/0.2) (Yield: 55%).

LCMS (Tr): 7.68 min (Method A); MS (ES+) gave m/z: 366.1.

$^1$H-NMR (CDCl$_3$, 333K, 300 MHz), δ (ppm): 7.44 (tt, 1H); 7.02 (dd, 2H); 4.29 (d br, 1H); 3.94 (ddd, 1H); 3.32 (dd, 1H); 3.19 (tt, 1H); 3.01 (ddd, 1H); 2.27 (m, 1H); 199-1.78 (m, 2H); 1.74-1.54 (m, 1H); 1.46 (s, 9H).

51(B) S-3-[3-(2,6-Difluoro-phenyl)-[1,2,4]oxadiazol-5-yl]-piperidine hydrochloride The compound was prepared following the procedure described in the Example 49(B), starting from S-3-[3-(2,6-difluoro-phenyl)-[1,2,4]oxadiazol-5-yl]-piperidine-1-carboxylic acid tert-butyl ester (yield: 100%).

LCMS (Tr): 4.24 min (Method B); MS (ES+) gave m/z: 266.1.

51(C) {(S)-3-[3-(2,6-Difluoro-phenyl)-[1,2,4]oxadiazol-5-yl]-piperidin-1-yl}-(4-fluoro-phenyl)-methanone The compound was prepared following the procedure described in the Example 49(C), starting from S-3-[3-(2,6-difluoro-phenyl)-[1,2,4]oxadiazol-5-yl]-piperidine hydrochloride and using 4-fluorobenzoyl chloride as the acyl chloride of choice. {(S)-3-[3-(2,6-Difluoro-phenyl)-[1,2,4]oxadiazol-5-yl]-piperidin-1-yl}-(4-fluoro-phenyl)-methanone was obtained pure after flash chromatography (2 successive columns under the following conditions: silica gel, eluent: DCM/hexane/MeOH 50/50/0.2).

Yield: 60% (thick oil); $[\alpha]_D^{20}$=+97° (c=1.14, CHCl$_3$); LCMS (Tr): 7.10 min (Method A); MS (ES+) gave m/z: 388.1.

$^1$H-NMR (CDCl$_3$, 328K, 300 MHz), δ (ppm): 7.50-7.39 (m, 3H); 7.12-6.98 (m, 4H); 4.41 (d br, 1H); 3.99 (d br, 1H); 3.54 (dd, 1H); 3.35-3.21 (m, 2H); 2.35 (m, 1H); 2.11-1.87 (m, 2H); 1.75-1.60 (m, 1H).

Example 52

(4-Fluoro-phenyl)-{(S)-3-[3-(2-methoxy-phenyl)-[1,2,4]oxadiazol-5-yl]-piperidin-1-yl}-methanone

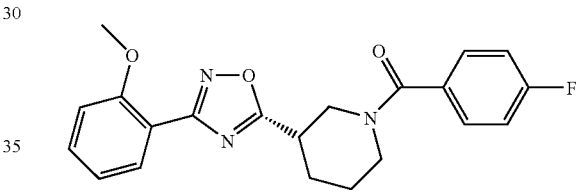

52(A) S-3-[3-(2-Methoxy-phenyl)-[1,2,4]oxadiazol-5-yl]-piperidine-1-carboxylic acid tert-butyl ester The compound was prepared following the procedure described in the Example 49(A), starting from 2-methoxybenzonitrile. S-3-[3-(2-Methoxy-phenyl)-[1,2,4]oxadiazol-5-yl]-piperidine-1-carboxylic acid tert-butyl ester was obtained pure after flash chromatography (silica gel, eluent: hexane/ethyl acetate 8/2) (Yield: 39%).

LCMS (Tr): 7.19 min (Method A); MS (ES+) gave m/z: 360.1.

$^1$H-NMR (CDCl$_3$, 333K, 300 MHz), δ (ppm): 7.97 (dd, 1H); 7.45 (ddd, 1H); 7.06 (ddd, 1H); 7.04 (dd, 1H); 4.33 (d br, 1H); 3.97 (ddd, 1H); 3.95 (s, 3H); 3.28 (dd, 1H); 3.15 (tt, 1H); 2.98 (ddd, 1H); 2.27 (m, 1H); 1.98-1.79 (m, 2H); 1.69-1.53 (m, 1H); 1.47 (s, 9H).

52(B) S-3-[3-(2-Methoxy-phenyl)-[1,2,4]oxadiazol-5-yl]-piperidine hydrochloride The compound was prepared following the procedure described in the Example 49(B), starting from S-3-[3-(2-methoxy-phenyl)-[1,2,4]oxadiazol-5-yl]-piperidine-1-carboxylic acid tert-butyl ester (yield: 100%).

LCMS (Tr): 4.40 min (Method B); MS (ES+) gave m/z: 260.1.

52(C) (4-Fluoro-phenyl)-{(S)-3-[3-(2-methoxy-phenyl)-[1,2,4]oxadiazol-5-yl]-piperidin-1-yl}-methanone The compound was prepared following the procedure described in the Example 49(C), starting from S-3-[3-(2-methoxy-phenyl)-[1,2,4]oxadiazol-5-yl]-piperidine hydrochloride and using 4-fluorobenzoyl chloride as the acyl chloride of choice. (4-Fluoro-phenyl)-{(S)-3-[3-(2-methoxy-phenyl)-[1,2,4]oxadiazol-5-yl]-piperidin-1-yl}-methanone was obtained pure after flash chromatography (silica gel, eluent: hexane/ethyl acetate 6/4).

Yield: 47% (gummy solid); $[\alpha]_D^{20}=+88°$ (c=0.98, CHCl$_3$); LCMS (Tr): 7.33 min (Method A); MS (ES+) gave m/z: 382.1.

$^1$H-NMR (CDCl$_3$, 333K, 300 MHz), δ (ppm): 7.93 (dd, 1H); 7.49-7.39 (m, 3H); 7.12-7.01 (m, 4H); 4.40 (d br, 1H); 4.00 (d br, 1H); 3.94 (s, 3H); 3.52 (dd, 1H); 3.25 (m, 2H); 2.34 (m, 1H); 2.09-1.86 (m, 2H); 1.68 (m, 1H).

Example 53

(4-Fluoro-phenyl)-[(S)-3-(3-naphthalen-2-yl-[1,2,4]oxadiazol-5-yl)-piperidin-1-yl]-methanone

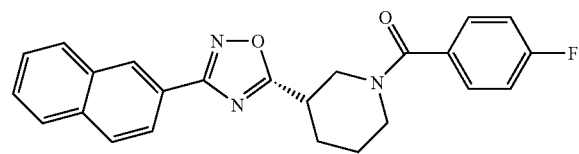

53(A) S-3-(3-Naphthalen-2-yl-[1,2,4]oxadiazol-5-yl)-piperidine-1-carboxylic acid tert-butyl ester The compound was prepared following the procedure described in the Example 49(A), starting from 2-cyanonaphtalene. S-3-(3-Naphthalen-2-yl-[1,2,4]oxadiazol-5-yl)-piperidine-1-carboxylic acid tert-butyl ester was obtained pure after flash chromatography (silica gel, eluent: DCM/hexane/MeOH 50/50/0.2) (Yield: 58%).

LCMS (Tr): 8.72 min (Method A); MS (ES+) gave m/z: 380.1.

$^1$H-NMR (CDCl$_3$, 333K, 300 MHz), δ (ppm): 8.61 (s br, 1H); 8.148 dd, 1H); 7.97-7.82 (m, 3H); 7.57-7.48 (m, 2H); 4.32 (d br, 1H); 3.95 (ddd, 1H); 3.36 (dd, 1H); 3.19 (tt, 1H); 3.05 (ddd, 1H); 2.29 (m, 1H); 2.02-1.82 (m, 2H); 1.71-1.58 (m, 1H).

53(B) S-3-(3-Naphthalen-2-yl-[1,2,4]oxadiazol-5-yl)-piperidine hydrochloride The compound was prepared following the procedure described in the Example 49(B), starting from S-3-(3-naphthalen-2-yl-[1,2,4]oxadiazol-5-yl)-piperidine-1-carboxylic acid tert-butyl ester (yield: 100%).

LCMS (Tr): 5.96 min (Method B); MS (ES+) gave m/z: 280.1.

53(C) (4-Fluoro-phenyl)-[(S)-3-(3-naphthalen-2-yl-[1,2,4]oxadiazol-5-yl)-piperidin-1-yl]-methanone The compound was prepared following the procedure described in the Example 49(C), starting from S-3-(3-naphthalen-2-yl-[1,2,4]oxadiazol-5-yl)-piperidine hydrochloride and using 4-fluorobenzoyl chloride as the acyl chloride of choice. (4-Fluoro-phenyl)-[(S)-3-(3-naphthalen-2-yl-[1,2,4]oxadiazol-5-yl)-piperidin-1-yl]-methanone was obtained pure after flash chromatography (silica gel, eluent: hexane/ethyl acetate 8/2).

Yield: 14% (white solid); mp=142-143° C.; $[\alpha]_D^{20}=+123°$ (c=1.025, CHCl$_3$); LCMS (Tr): 7.97 min (Method A); MS (ES+) gave m/z: 402.1.

$^1$H-NMR (CDCl$_3$, 333K, 300 MHz), δ (ppm): 8.59 (s br, 1H); 8.12 (dd, 1H); 7.97-7.84 (m, 3H); 7.59-7.49 (m, 2H); 7.45 (dd, 2H); 7.10 (dd, 2H); 4.45 (d br, 1H); 4.01 (d br, 1H); 3.58 (dd, 1H); 3.29 (m, 2H); 2.38 (m, 1H); 2.14-1.89 (m, 2H); 1.78-1.65 (m, 1H).

Example 54

(4-Fluoro-phenyl)-[(S)-3-(3-p-tolyl-[1,2,4]oxadiazol-5-yl)-piperidin-1-yl]-methanone

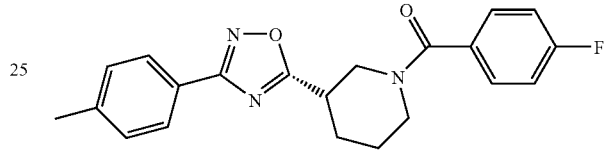

54(A) S-3-(3-p-Tolyl-[1,2,4]oxadiazol-5-yl)-piperidine-1-carboxylic acid tert-butyl ester The compound was prepared following the procedure described in the Example 49(A), starting from 4-methylbenzonitrile. S-3-(3-p-Tolyl-[1,2,4]oxadiazol-5-yl)-piperidine-1-carboxylic acid tert-butyl ester was obtained pure after trituration from hexane/diethyl ether 1/1 (Yield: 78%).

LCMS (Tr): 11.0 min (Method B); MS (ES+) gave m/z: 344.4.

$^1$H-NMR (CDCl$_3$, 333K, 300 MHz), δ (ppm): 7.96 (d, 2H); 7.26 (d, 2H); 4.28 (d br, 1H); 3.93 (ddd, 1H); 3.30 (dd, 1H); 3.13 (tt, 1H); 3.01 (ddd, 1H); 2.41 (s, 3H); 2.25 (m, 1H); 1.97-1.788 m, 2H); 1.69-1.52 (m, 1H); 1.47 (s, 9H).

54(B) S-3-(3-p-Tolyl-[1,2,4]oxadiazol-5-yl)-piperidine hydrochloride

The compound was prepared following the procedure described in the Example 49(B), starting from S-3-(3-p-Tolyl-[1,2,4]oxadiazol-5-yl)-piperidine-1-carboxylic acid tert-butyl ester (yield: 100%).

LCMS (Tr): 5.3 min (Method B); MS (ES+) gave m/z: 244.4.

54(C) (4-Fluoro-phenyl)-[(S)-3-(3-p-tolyl-[1,2,4]oxadiazol-5-yl)-piperidin-1-yl]-methanone The compound was prepared following the procedure described in the Example 49(C), starting from S-3-(3-p-Tolyl-[1,2,4]oxadiazol-5-yl)-piperidine hydrochloride and using 4-fluorobenzoyl chloride as the acyl chloride of choice. (4-Fluoro-phenyl)-[(S)-3-(3-p-tolyl-[1,2,4]oxadiazol-5-yl)-piperidin-1-yl]-methanone was obtained pure after flash chromatography (silica gel, eluent: hexane/ethyl acetate 8/2).

Yield: 33% (thick oil); $[\alpha]_D^{20}=+106°$ (c=1.0, CHCl$_3$); LCMS (Tr): 9.5 min (Method B); MS (ES+) gave m/z: 366.0.

¹H-NMR (CDCl₃, 333K, 300 MHz), δ (ppm): 7.94 (d, 2H); 7.43 (dd, 2H); 7.27 (d, 2H); 7.09 (dd, 2H); 4.40 (d br, 1H); 3.99 (d br, 1H); 3.52 (dd, 1H); 3.31-3.188 m, 2H); 2.41 (s, 3H); 2.33 (m, 1H); 2.09-1.86 (m, 2H); 1.75-1.59 (m, 1H).

Example 55

(4-Fluoro-phenyl)-{(S)-3-[3-(2-fluoro-phenyl)-[1,2,4]oxadiazol-5-yl]-piperidin-1-yl}-methanone

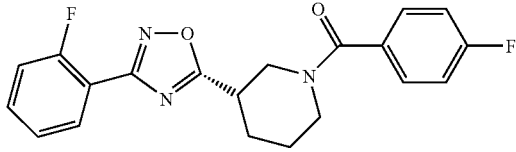

55(A) S-3-[3-(2-Fluoro-phenyl)-[1,2,4]oxadiazol-5-yl]-piperidine-1-carboxylic acid tert-butyl ester The compound was prepared following the procedure described in the Example 49(A), starting from 2-fluorobenzonitrile. S-3-[3-(2-Fluoro-phenyl)-[1,2,4]oxadiazol-5-yl]-piperidine-1-carboxylic acid tert-butyl ester was obtained pure after trituration from hexane/diethyl ether 1/1 (Yield: 83%).

LCMS (Tr): 7.79 min (Method A); MS (ES+) gave m/z: 348.1.

¹H-NMR (CDCl₃, 333K, 300 MHz), δ (ppm): 8.04 (ddd, 1H); 7.47 (m, 1H); 7.25 (ddd, 1H); 7.21 (m, 1H); 4.30 (d br, 1H); 3.94 (ddd, 1H); 3.32 (dd, 1H); 3.18 (tt, 1H); 3.02 (ddd, 1H); 2.26 (m, 1H); 1.99-1.79 (m, 2H); 1.69-1.53 (m, 1H); 1.47 (s, 9H).

55(B) S-3-[3-(2-Fluoro-phenyl)-[1,2,4]oxadiazol-5-yl]-piperidine hydrochloride

The compound was prepared following the procedure described in the Example 49(B), starting from S-3-[3-(2-fluoro-phenyl)-[1,2,4]oxadiazol-5-yl]-piperidine-1-carboxylic acid tert-butyl ester (yield: 100%).

LCMS (Tr): 4.7 min (Method B); MS (ES+) gave m/z: 248.1.

55(C) (4-Fluoro-phenyl)-{(S)-3-[3-(2-fluoro-phenyl)-[1,2,4]oxadiazol-5-yl]-piperidin-1-yl}-methanone The compound was prepared following the procedure described in the Example 49(C), starting from S-3-[3-(2-fluoro-phenyl)-[1,2,4]oxadiazol-5-yl]-piperidine hydrochloride and using 4-fluorobenzoyl chloride as the acyl chloride of choice. (4-Fluoro-phenyl)-{(S)-3-[3-(2-fluoro-phenyl)-[1,2,4]oxadiazol-5-yl]-piperidin-1-yl}-methanone was obtained pure after flash chromatography (silica gel, eluent: hexane/ethyl acetate 8/2).

Yield: 22% (thick oil); [α]_D^{20}=+102° (c=1.045, CHCl₃); LCMS (Tr): 7.31 min (Method A); MS (ES+) gave m/z: 370.1.

¹H-NMR (CDCl₃, 333K, 300 MHz), δ (ppm): 8.01 (ddd, 1H); 7.52-7.41 (m, 1H); 7.43 (dd, 2H); 7.29-7.18 (m, 2H); 7.09 (dd, 2H); 4.41 (d br, 1H); 3.99 (d br, 1H); 3.54 (dd, 1H); 3.27 (m, 2H); 2.34 (m, 1H); 2.10-1.87 (m, 2H); 1.76-1.61 (m, 1H).

Example 56

(4-Fluoro-phenyl)-[(S)-3-(3-pyridin-2-yl-[1,2,4]oxadiazol-5-yl)-piperidin-1-yl]-methanone

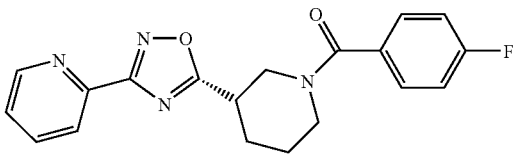

56(A) S-3-(3-Pyridin-2-yl-[1,2,4]oxadiazol-5-yl)-piperidine-1-carboxylic acid tert-butyl ester The compound was prepared following the procedure described in the Example 49(A), starting from 2-cyanopyridine. S-3-(3-Pyridin-2-yl-[1,2,4]oxadiazol-5-yl)-piperidine-1-carboxylic acid tert-butyl ester was obtained pure after purification by flash chromatography (silica gel, eluent: DCM/MeOH/NH₄OH 98/2/0.2) (Yield: 54%).

LCMS (Tr): 6.87 min (Method A); MS (ES+) gave m/z: 331.2.

¹H-NMR (CDCl₃, 333K, 300 MHz), δ (ppm): 8.80 (ddd, 1H); 8.11 (ddd, 1H); 7.82 (ddd, 1H); 7.40 (ddd, 1H); 4.33 (d br, 1H); 3.98 (ddd, 1H); 3.33 (dd, 1H); 3.20 (tt, 1H); 2.99 (ddd, 1H); 2.28 (m, 1H); 2.03-1.79 (m, 2H); 1.69-1.54 (m, 1H); 1.48 (s, 9H).

56(B) S-2-(5-Piperidin-3-yl-[1,2,4]oxadiazol-3-yl)-pyridine dihydrochloride

The compound was prepared following the procedure described in the Example 49(B), starting from S-3-(3-pyridin-2-yl-[1,2,4]oxadiazol-5-yl)-piperidine-1-carboxylic acid tert-butyl ester (yield: 100%).

LCMS (Tr): 3.12 min (Method B); MS (ES+) gave m/z: 231.2.

56(C) (4-Fluoro-phenyl)-[(S)-3-(3-pyridin-2-yl-[1,2,4]oxadiazol-5-yl)-piperidin-1-yl]-methanone The compound was prepared following the procedure described in the Example 49(C), starting from S-2-(5-piperidin-3-yl-[1,2,4]oxadiazol-3-yl)-pyridine dihydrochloride and using 4-fluorobenzoyl chloride as the acyl chloride of choice.

Yield: 78% (yellowish thick oil); [α]_D^{20}=+103° (c=1.05, CHCl₃); LCMS (Tr): 6.56 min (Method A); MS (ES+) gave m/z: 353.0.

¹H-NMR (CDCl₃, 333K, 300 MHz), δ (ppm): 8.79 (m, 1H); 8.09 (ddd, 1H); 7.82 (ddd, 1H); 7.47-7.37 (m, 3H); 7.08 (dd, 2H); 4.44 (d br, 1H); 4.05 (d br, 1H); 3.54 (dd, 1H); 3.29 (tt, 1H); 3.21 (ddd, 1H); 2.36 (m, 1H); 2.13-1.86 (m, 2H); 1.76-1.61 (m, 1H).

Example 57

S-(4-Fluoro-phenyl)-{3-[5-(4-fluoro-phenyl)-4-methyl-4H-1,2,4-triazol-3-yl]-piperidin-1-yl}-methanone

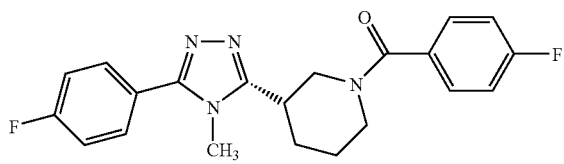

57(A) 1-(4-Fluoro-benzoyl)-(S)-piperidine-3-carboxylic acid

To a suspension of (S)-piperidine-3-carboxylic acid hydrochloride (0.75 g, 4.53 mmol) in dry dichloromethane (30 mL), triethylamine (1.97 mL, 14.0 mmol) and 4-fluorobenzoyl chloride (543 mL, 4.53 mmol) were added dropwise at 0° C. The resulting solution was kept under stirring overnight at room temperature, under nitrogen atmosphere, then HCl 1N (30 mL) was added and the phases were separated. The organic layer was washed with HCl 1N (30 mL), with water (30 mL), dried over $Na_2SO_4$ and evaporated under reduced pressure to provide 1.05 g of 1-(4-fluoro-benzoyl)-(S)-piperidine-3-carboxylic acid as a yellow oil, used for the next step without further purification.

Yield: 92%; LCMS (Tr): 6.55 min (Method B); MS (ES+) gave m/z: 252.3.

57(B) N'-[1-(4-Fluoro-benzoyl)-(S)-piperidine-3-carbonyl]-hydrazinecarboxylic acid-tert-butyl ester A mixture of 1-(4-fluoro-benzoyl)-(S)-piperidine-3-carboxylic acid (1.05 g, 4.17 mmol), tert-butyl carbazate (0.55 g, 4.17 mmol), HOBT (0.562 g, 4.17 mmol), EDCI.HCl (1.2 g, 6.25 mmol) in dry dichloromethane (8 mL) was kept under stirring overnight at ambient temperature, under nitrogen atmosphere. HCl 1N (30 mL) was then added and the phases separated. The organic layer was washed with HCl 1N (30 mL), with NaOH 1N (30 mL×2 times), then with water (30 mL). Evaporation of the organic solvent afforded a crude yellow oil which was purified by flash chromatography (silica gel, eluent: DCM/MeOH 70/1) to give 0.715 g of N'-[1-(4-fluoro-benzoyl)-(S)-piperidine-3-carbonyl]-hydrazinecarboxylic acid-tert-butyl ester.

Yield: 47% (yellow oil); LCMS (Tr): 6.40 min (Method A); MS (ES+) gave m/z: 366.2.

$^1$H-NMR (CDCl$_3$, 333K, 300 MHz), δ (ppm): 8.04 (s br, 1H); 7.47-7.36 (m, 2H); 7.12-7.01 (m, 2H); 6.42 (s br, 1H); 4.12-3.90 (m br, 1H); 3.88-3.51 (m br, 2H); 3.34-3.09 (m br, 1H); 2.62-2.36 (m br, 1H); 2.18-1.84 (m, 2H); 1.81-1.64 (m, 1H); 1.47 (s, 9H); 1.52-1.43 (m, 1H)

57(C) 1-(4-Fluoro-benzoyl)-(S)-piperidine-3-carboxylic acid hydrazide hydrochloride 0.55 g (1.5 mmol) of N'-[1-(4-fluoro-benzoyl)-(S)-piperidine-3-carbonyl]-hydrazinecarboxylic acid-tert-butyl ester were suspended in 5 mL of dichloromethane and, at 0° C., 4 mL of HCl 4N (dioxane solution) were added. The solution was allowed to warm at room temperature and stirred for 1 h 30. The solvent was evaporated under reduced pressure to afford 0.412 g of 1-(4-fluoro-benzoyl)-(S)-piperidine-3-carboxylic acid hydrazide as a white solid extremely igroscopic.

Yield: 91%; LCMS (Tr): 5.4 min (Method B); MS (ES+) gave m/z: 266.2.

$^1$H-NMR (CDCl$_3$, 333K+D$_2$O, 300 MHz), δ (ppm): 7.41 (dd, 2H); 7.08 (dd, 2H); 4.45 (m, 1H); 4.11 (m, 1H); 3.84 (m, 1H); 3.39 (dd, 1H); 3.13 (m, 1H); 2.39 (m, 1H); 1.95 (m, 2H); 1.85-1.75 (m, 1H).

57(D) 4-Fluoro-N-methyl-benzimidoyl chloride

A suspension of 4-fluoro-N-methyl-benzamide (CAS: 701-49-5, 0.106 g, 0.69 mmol) in thionyl chloride (202 mL, 2.78 mmol) was refluxed for 1 h 30 min. The solvent was removed under reduced pressure, then toluene was added and the solvent was evaporated under reduced pressure to afford a yellow oil used immediately for the next step.

57(E) S-(4-Fluoro-phenyl)-{3-[5-(4-fluoro-phenyl)-4-methyl-4H-1,2,4-triazol-3-yl]-piperidin-1-yl}-methanone To a solution of 4-fluoro-N-methyl-benzimidoyl chloride, prepared as described in 58 (D), in dry toluene (8 mL), 1-(4-fluoro-benzoyl)-(S)-piperidine-3-carboxylic acid hydrazide hydrochloride (0.21 g, 0.69 mmol) and anhydrous triethylamine (204 mL, 1.46 mmol) were added under nitrogen atmosphere and the resulting mixture was refluxed for 2 h. The solvent was removed under reduced pressure, diluted with dichloromethane and washed with NaHCO$_3$ (aq.). The organic layer was dried over Na$_2$SO$_4$ and evaporated under reduced pressure. The crude was then purified by 2 successive flash chromatography (first column: silica gel, eluent gradient: from DCM/MeOH 20:1 to DCM/MeOH 4:1; second column: silica gel, eluent gradient: from acetone/ethyl acetate 1:1 to acetone/ethyl acetate 2:1) to give 20 mg of S-(4-fluorophenyl)-{3-[5-(4-fluoro-phenyl)-4-methyl-4H-1,2,4-triazol-3-yl]-piperidin-1-yl}-methanone.

Yield: 8% (white solid); LCMS (Tr): 6.26 min (Method A); MS (ES+) gave m/z: 383.1.

$^1$H-NMR (CDCl$_3$, 300 MHz), δ (ppm): 7.65 (dd, 2H); 7.46 (dd, 2H); 7.20 (dd, 2H); 7.10 (dd, 2H); 4.46 (m br, 1H); 4.01 (m br, 1H); 3.66 (s, 3H); 3.39 (m, 1H); 3.19 (m, 1H); 2.98 (m br, 1H); 2.28-1.89 (m, 3H); 1.60 (m, 1H).

Example 58

(4-Fluoro-phenyl)-{(S)-3-[5-(4-fluoro-phenyl)-[1,3,4]oxadiazol-2-yl]-piperidin-1-yl}-methanone

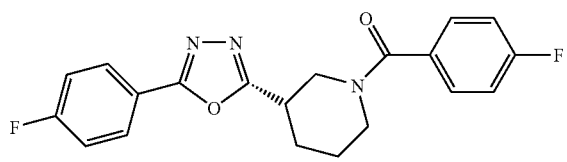

58(A) 4-Fluoro-benzoic acid N'-[(S)-1-(4-fluoro-benzoyl)-piperidine-3-carbonyl]-hydrazide A mixture of 1-(4-fluoro-benzoyl)-(S)-piperidine-3-carboxylic acid hydrazide hydrochloride, already prepared as described in Example 57 (C) (2.97 g, 11.2 mmol), 4-fluorobenzoic acid (1.68 g, 11.2 mmol), HOBT (1.5 g, 11.2 mmol), EDCI.HCl (3.2 g, 16.8 mmol) and dry triethylamine (5.43 mL, 39.5 mmol) in dry dichloromethane (80 mL) was kept under stirring overnight at ambient temperature, under nitrogen atmosphere. HCl 1N (80 mL) was then added and the phases separated. The organic layer was washed with HCl 1N (80 mL), with NaOH 1N (80 mL×2 times), then with water (80 mL). Evaporation of the organic solvent afforded a crude oil which was purified by flash chromatography (silica gel, eluent: DCM/MeOH/NH$_4$OH 98/2/0.2). The compound obtained after column chromatography was purified again by flash chromatography (silica gel, eluent: DCM/MeOH/NH$_4$OH 98/2/0.2) to provide the pure 4-fluoro-benzoic acid N'-[(S)-1-(4-fluoro-benzoyl)-piperidine-3-carbonyl]-hydrazide as a white solid (250 mg).

Yield: 6%, LCMS (Tr): 5.88 min (Method A); MS (ES+) gave m/z: 388.0.

$^1$H-NMR (CDCl$_3$, 333K, 300 MHz), δ (ppm): 8.91 (s br, 1H); 8.35 (s br, 1H); 7.83 (dd, 2H); 7.47 (dd, 2H); 7.13 (dd, 2H); 7.09 (dd, 2H); 4.03-3.76 (m, 3H); 3.32 (m, 1H); 2.61 (m, 1H); 2.22-1.93 (m, 2H); 1.77 (m, 1H); 1.55 (m, 1H).

58(B) (4-Fluoro-phenyl)-{3-[5-(4-fluoro-phenyl)-[1,3,4]oxadiazol-2-yl]-piperidin-1-yl}-methanone A mixture of 4-fluoro-benzoic acid N'-[(S)-1-(4-fluorobenzoyl)-piperidine-3-carbonyl]-hydrazide (100 mg, 0.26 mmol), 4-toluenesulfonyl chloride (60 mg, 0.31 mmol), solid supported 2-tert-Butylimino-2-diethylamino-1,3-dimethyl-perhydro-1,3,2-diaza-phosphorine (PS-BEMP, ex Fluka, 586 mg, 1.3 mmol, loading 2.2 mmol/g) in dry tetrahydrofuran (6 mL) was irradiated by microwaves under the following conditions: MW cycle: t=1 min, P=100 W, cooling time=2 min. After 5 MW cycles, the resin was filtered off and washed repeatedly with dichloromethane. The solvent was evaporated under reduced pressure to give a crude solid that was purified by flash chromatography (silica gel, eluent: hexane/ethyl acetate 1:1). The title compound was obtained as a white solid (82 mg).

Yield: 85%; LCMS (Tr): 6.75 min (Method A); MS (ES+) gave m/z: 370.1.

$^1$H-NMR (CDCl$_3$, 300 K, 300 MHz), δ (ppm): 8.02 (m, 2H); 7.41 (m, 2H); 7.31-6.93 (m, 4H); 4.96-3.37 (m, 3H); 3.22 (m, 2H), 2.32 (m, 1H); 2.20-1.63 (m, 3H).

Example 59

(2-Fluoro-phenyl)-{(S)-3-[2-(3,4-difluoro-phenyl)-1,2,4]oxadiazol-5-yl]-piperidin-1-yl}-methanone

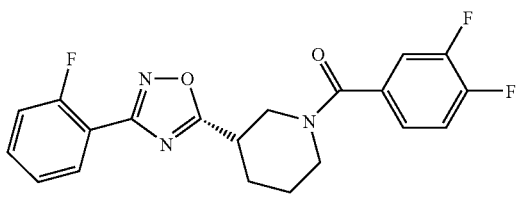

The compound was prepared following the procedure described in the Example 49(C), starting from S-3-[3-(2-fluoro-phenyl)-[1,2,4]oxadiazol-5-yl]-piperidine hydrochloride and using 3,4-difluorobenzoyl chloride as the acyl chloride of choice. (2-Fluoro-phenyl)-{(S)-3-[2-(3,4-difluoro-phenyl)-1,2,4]oxadiazol-5-yl]-piperidin-1-yl}-methanone was obtained pure after flash chromatography (silica gel, eluent:DCM//MeOH/NH$_4$OH 99/1/0.1).

Yield: 61% (gummy solid); mp=115-119° C.; [α]$_D^{20}$=+92.2° (c=1.14, CHCl$_3$); LCMS (Tr): 7.25 min (Method A); MS (ES+) gave m/z: 388.0.

$^1$H-NMR (CDCl$_3$, 333K, 300 MHz), δ (ppm): 8.01 (ddd, 1H); 7.48 (m, 1H); 7.33-7.15 (m, 5H); 4.37 (m, 1H); 3.93 (m, 1H); 3.59 (dd, 1H); 3.37-3.23 (m, 2H); 2.35 (m, 1H); 2.13-1.87 (m, 2H); 1.76-1.61 (m, 1H).

Example 60

(4-Fluoro-phenyl)-{2-[3-(4-fluoro-phenyl)-[1,2,4]oxadiazol-5-yl]-morpholin-4-yl}-methanone

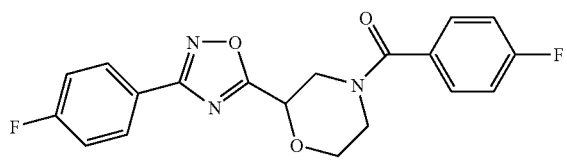

60(A) 2-[3-(4-Fluoro-phenyl)-[1,2,4]oxadiazol-5-yl]-morpholine-4-carboxylic acid tert-butyl ester A mixture of (R,S)—N-Boc-2-carboxymorpholine (0.5 g, 2.16 mmol), N-hydroxy-4-fluoro-benzamidine (0.333 g, 2.16 mmol), EDCI.HCl (0.621 g, 3.24 mmol), HOBT (0.292 g, 2.16 mmol) and anhydrous triethylamine (605 mL, 4.32 mmol) in dioxane (7 mL) was stirred overnight at room temperature, under nitrogen atmosphere. The mixture was then refluxed for 4 h and concentrated under reduced pressure. The residue was diluted with ethyl acetate (15 mL) and water (15 mL) and the phases were separated. The organic layer was washed with NaOH 1N (15 mL) and brine, dried over sodium sulphate and evaporated under reduced pressure. The crude was purified by flash chromatography (silica gel, eluent: hexane/ethyl acetate 9/1) to afford 325 mg (yield: 43%) of 2-[3-(4-fluoro-phenyl)-[1,2,4]oxadiazol-5-yl]-morpholine-4-carboxylic acid tert-butyl ester as a white oil.

LCMS (Tr): 7.51 min (Method A); MS (ES+) gave m/z: 350.1.

$^1$H-NMR (CDCl$_3$, 300 MHz), δ (ppm): 8.11 (dd, 2H); 7.16 (dd, 2H); 4.83 (dd, 1H); 4.27 (m br, 1H); 4.09 (m, 1H); 3.87 (m, 1H); 3.74 (ddd, 1H); 3.41 (m br, 1H); 3.23 (ddd, 1H); 1.48 (s, 9H).

60(B) 2-[3-(4-Fluoro-phenyl)-[1,2,4]oxadiazol-5-yl]-morpholine hydrochloride

2-[3-(4-Fluoro-phenyl)-[1,2,4]oxadiazol-5-yl]-morpholine-4-carboxylic acid tert-butyl ester (0.325 g, 0.93 mmol) was dissolved in dichloromethane (3 mL) and 5 mL of HCl 4N (dioxane solution) were added dropwise. The resulting mixture was stirred at room temperature for 2 h. The solvent was evaporated under reduced pressure to afford 265 mg (yield: 100%) of 2-[3-(4-fluoro-phenyl)-[1,2,4]oxadiazol-5-yl]-morpholine hydrochloride as a white solid.

LCMS (Tr): 5.68 min (Method A); MS (ES+) gave m/z: 250.1.

$^1$H-NMR (DMSO, 300 MHz), δ (ppm): 9.58 (s br, 1H); 8.09 (dd, 2H); 7.43 (dd, 2H); 5.38 (dd, 1H); 4.19-3.97 (m, 2H); 3.71 (dd, 1H); 3.45 (dd, 1H), 3.30-3.12 (m, 2H).

60(C) (4-Fluoro-phenyl)-{2-[3-(4-fluoro-phenyl)-[1,2,4]oxadiazol-5-yl]-morpholin-4-yl}-methanone To a suspension of 2-[3-(4-fluoro-phenyl)-[1,2,4]oxadiazol-5-yl]-morpholine hydrochloride (0.15 g, 0.53 mmol) in anhydrous dichloromethane (6 mL), under nitrogen atmosphere, triethylamine (155 mL, 1.1 mmol) and 4-fluorobenzoyl chloride (62 mL, 0.53 mmol) were subsequently added at 0° C. The reaction mixture was allowed to warm at room temperature and stirred overnight. HCl 1N (6 mL) was added and the phases were separated. The organic layer was washed sequentially with HCl 1N (6 mL), NaOH 1N (6 mL×2 times) and with water, then was dried over sodium sulphate and evaporated under reduced pressure. The crude was purified by flash chromatography (silica gel, eluent: hexane/ethyl acetate 7/3) to afford 120 mg of (4-fluoro-phenyl)-{2-[3-(4-fluoro-phenyl)-[1,2,4]oxadiazol-5-yl]-morpholin-4-yl}-methanone as a white solid.

Yield: 61%; mp=116-117° C.; LCMS (Tr): 7.33 min (Method A); MS (ES+) gave m/z: 372.0.

$^1$H-NMR (CDCl$_3$, 300 MHz, 330 K), δ (ppm): 8.08 (dd, 2H); 7.47 (dd, 2H); 7.16 (dd, 2H); 7.12 (dd, 2H); 4.90 (dd, 1H); 4.39 (d br, 1H); 4.12 (ddd, 1H); 3.95 (d br, 1H); 3.79 (ddd, 1H); 3.71 (dd, 1H); 3.53 (ddd, 1H).

Example 61

(4-Fluoro-phenyl)-{3-[3-(4-fluoro-phenyl)-[1,2,4]oxadiazol-5-yl]-4-methyl-piperazine-1-yl}-methanone

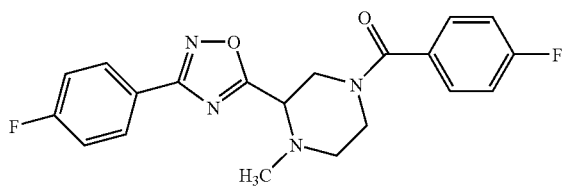

61(A) Piperazine-1,3-dicarboxylic acid-1-tert-butyl ester

To a solution of 2-piperazine-carboxylic acid dihydrochloride (1.0 g, 4.92 mmol) in 20 mL of water/dioxane 1:1, NaOH 6N was added to adjust the pH to 11. A solution of BOC-ON® (1.34 g, 5.41 mmol) in dioxane (5 mL) was then added dropwise, while maintaining the pH=11 during the addition and the resulting solution was stirred overnight at room temperature. Another 0.134 g of BOC-ON® were added and the reaction mixture was stirred for 2 h. The solvent was evaporated under reduced pressure and the residue was diluted with diethyl ether/water (60 mL). The phases were separated and the pH of the aqueous layer was adjusted to 7 by slow addition of HCl 1N. Evaporation of water under reduced pressure afforded the title compound as a white solid which was dried in a vacuum oven at 50° C. and used without further purification for the next step.

LCMS (Tr): 3.3 min (Method B); MS (ES+) gave m/z: 231.0.

61(B) 4-Methyl-piperazine-1,3-dicarboxylic acid 1-tert-butyl ester

The crude piperazine-1,3-dicarboxylic acid-1-tert-butyl ester (4.92 mmol), prepared as described in 62(A), was suspended in dry acetonitrile (30 mL) under nitrogen atmosphere and formaldehyde (37% wt. aqueous solution, 367 mL, 4.92 mmol) and Na(OAc)$_3$BH (2.3 g, 10.82 mmol) were added. The resulting mixture was stirred at R.T. for 3 h, then a saturated aqueous solution of NaHCO$_3$ was slowly added until the pH was adjusted to 7. The mixture was concentrated to dryness under reduced pressure to give a yellow solid that was used without further purification for the next step.

LCMS (Tr): 3.19 min (Method B); MS (ES+) gave m/z: 245.0.

61(C) 3-[3-(4-Fluoro-phenyl)-[1,2,4]oxadiazol-5-yl]-4-methyl-piperazine-1-carboxylic acid tert-butyl ester A mixture of N-hydroxy-4-fluoro-benzamidine (0.758 g, 4.92 mmol), 4-methyl-piperazine-1,3-dicarboxylic acid 1-tert-butyl ester (4.92 mmol), prepared as described in 62(B), EDCI.HCl (1.41 g, 7.38 mmol), HOBT (0.665 g, 4.92 mmol) and anhydrous triethylamine (1.38 mL, 9.84 mmol) in dioxane (80 mL) was stirred at room temperature for a weekend, under nitrogen atmosphere. Then, the reaction mixture was refluxed for 7 h and the solvent was evaporated under reduced pressure. The residue was diluted with water (50 mL) and ethyl acetate (50 mL), the phases were separated and the organic layer was washed sequentially with water (50 mL×2 times) and with NaOH 1N (50 mL×2 times). The organic layer was dried over Na$_2$SO$_4$ and concentrated under reduced pressure to give a yellow oil. Purification of the crude by flash chromatography (silica gel, eluent gradient: from hexane/ethyl acetate 8/2 to hexane/ethyl acetate 7/3) afforded 0.312 g of 3-[3-(4-fluoro-phenyl)-[1,2,4]oxadiazol-5-yl]-4-methyl-piperazine-1-carboxylic acid tert-butyl ester as a yellow oil.

Overall yield of the three steps 22(A), 22(B) and 22(C): 18%.

LCMS (Tr): 7.34 min (Method B); MS (ES+) gave m/z: 363.1.

$^1$H-NMR (CDCl$_3$, 300 MHz, 328 K), δ (ppm): 8.11 (dd, 2H); 7.16 (dd, 2H); 4.01-3.90 (m, 2H); 3.83-3.62 (m, 3H); 3.17 (m, 1H); 2.55 (m, 1H); 2.43 (s, 3H); 1.41 (s, 9H).

61(D) 2-[3-(4-Fluoro-phenyl)-[1,2,4]oxadiazol-5-yl]-1-methyl-piperazine dihydrochloride HCl 4N (3 mL dioxane solution) was dropped into a solution of -[3-(4-fluoro-phenyl)-[1,2,4]oxadiazol-5-yl]-4-methyl-piperazine-1-carboxylic acid tert-butyl ester (0.312 g, 0.86 mmol) in methanol (8 mL) and the solution was kept under stirring overnight at R.T. Evaporation of the volatiles under reduced pressure provided 2-[3-(4-fluoro-phenyl)-[1,2,4]oxadiazol-5-yl]-1-methyl-piperazine dihydrochloride as a white solid (0.285 g).

Yield: 100%; LCMS (Tr): 5.63 min (Method A); MS (ES+) gave m/z: 263.2.

$^1$H-NMR (CDCl$_3$, 300 MHz, 328 K), δ (ppm): 8.11 (dd, 2H); 7.16 (dd, 2H); 4.01-3.90 (m, 2H); 3.83-3.62 (m, 3H); 3.17 (m, 1H); 2.55 (m, 1H); 2.43 (s, 3H); 1.41 (s, 9H).

61(E) (4-Fluoro-phenyl)-{3-[3-(4-fluoro-phenyl)-[1,2,4]oxadiazol-5-yl]-4-methyl-piperazine-1-yl}-methanone To a suspension of 2-[3-(4-fluoro-phenyl)-[1,2,4]oxadiazol-5-yl]-1-methyl-piperazine dihydrochloride (0.285 g, 0.86 mmol) in anhydrous dichloromethane (6 mL), under nitrogen atmosphere, triethylamine (374 mL, 2.7 mmol) and 4-fluorobenzoyl chloride (102 mL, 0.86 mmol) were subsequently added at 0° C. The reaction mixture was allowed to warm at room temperature and stirred for 2 h. NaOH 1N (6 mL) was added and the phases were separated. The organic layer was washed sequentially with NaOH 1N (6 mL) and with water, then was dried over sodium sulphate and evaporated under reduced pressure. Purification of the crude by flash chromatography (silica gel, eluent: DCM/MeOH/NH$_4$OH 99/1/0.1) afforded (4-fluoro-phenyl)-{3-[3-(4-fluoro-phenyl)-[1,2,4] oxadiazol-5-yl]-4-methyl-piperazine-1-yl}-methanone (0.12 g).

Yield: 36%; LCMS (Tr): 6.36 min (Method A); MS (ES+) gave m/z: 385.1.

$^1$H-NMR (CDCl$_3$, 328 K, 300 MHz), δ (ppm): 8.10 (dd, 2H); 7.40 (dd, 2H); 7.18 (dd, 2H); 7.06 (dd, 2H); 4.14-3.92 (m, 3H); 3.91-3.73 (m, 2H); 3.17 (m, 1H); 2.58 (m, 1H); 2.42 (s, 3H).

Example 62

(S)-1-(4-Fluoro-benzoyl)-piperidine-3-carboxylic acid (4-fluoro-phenyl)-amide

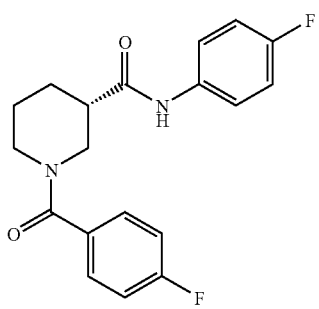

62(A) (S)-3-(4-Fluoro-phenylcarbamoyl)-piperidine-1-carboxylic acid tert-butyl ester A mixture of S-1-Boc-piperidine-3-carboxylic acid (0.3 g, 1.30 mmol), EDCI.HCl (0.376 g, 1.96 mmol), HOBT (0.198 g, 1.30 mmol) in dry dichloromethane (6 mL) was stirred at R.T. for 1 h, under nitrogen atmosphere. 4-Fluoroaniline (124 mL, 1.30 mmol) was then added and the reaction mixture was stirred overnight at ambient temperature. The solvent was evaporated under reduced pressure and the residue was diluted with water and ethyl acetate. The phases were separated, the organic layer was washed with Na$_2$CO$_3$ 2M (aq.), dried over sodium sulphate and concentrated under reduced pressure. The crude was purified by filtration through a silica gel cartridge (silica gel: 10 g, eluent gradient: from petroleum ether/ethyl acetate 9/1 to petroleum ether/ethyl acetate 8/2) to provide 0.35 g of (S)-3-(4-Fluoro-phenylcarbamoyl)-piperidine-1-carboxylic acid tert-butyl ester.

Yield: 84%; LCMS (Tr): 7.08 min (Method A); MS (ES+) gave m/z: 323.2.

$^1$H-NMR (CDCl$_3$, 300 MHz), δ (ppm): 8.26 (s br, 1H); 7.53 (dd, 2H); 6.98 (dd, 2H); 3.82 (m, 1H); 3.67-3.46 (m, 2H); 3.23 (m, 1H); 2.49 (m, 1H); 2.06 (m, 1H); 1.89 (m, 1H); 1.63 (m, 1H); 1.50 (m, 1H); 1.46 (s, 9H).

62(B) (S)-Piperidine-3-carboxylic acid (4-fluoro-phenyl)-amide hydrochloride

To a cooled solution of (S)-3-(4-fluoro-phenylcarbamoyl)-piperidine-1-carboxylic acid tert-butyl ester (0.34 g, 1.05 mmol) in dichloromethane (5 mL) was added dropwise 5.2 mL of HCl 4N (dioxane solution) and the solution was stirred at R.T. for 45 min. The solvent was evaporated under reduced pressure to give the title compound as a white solid (0.252 g).

Yield: 92%; LCMS (Tr): 5.39 min (Method A); MS (ES+) gave m/z: 223.2.

$^1$H-NMR (DMSO, 300 MHz), δ (ppm): 10.34 (s, 1H); 8.95 (s br, 2H); 7.63 (dd, 2H); 7.14 (dd, 2H); 3.18 (m, 2H); 3.02 (dd, 1H); 2.88 (m, 2H); 2.04 (m, 1H); 1.88-1.55 (m, 3H).

62(C) (S)-1-(4-Fluoro-benzoyl)-piperidine-3-carboxylic acid (4-fluoro-phenyl)-amide 4-Fluorobenzoyl chloride (53 mL, 0.45 mmol) was added at 0° C. to a solution of (S)-piperidine-3-carboxylic acid (4-fluoro-phenyl)-amide hydrochloride (0.116 g, 0.45 mmol) and triethylamine (131 mL, 0.94 mmol) in dichloromethane (3 mL), under nitrogen atmosphere. The reaction mixture was kept under stirring at R.T. for 2.5 h, the solvent was evaporated and the residue was diluted with water and ethyl acetate. The phases were separated and the organic layer was washed with HCl 1N (10 mL), with Na$_2$CO$_3$ 2M (aq.) (10 mL) and with brine (10 mL). The organic layer was dried over sodium sulphate and concentrated under reduced pressure to give 0.127 g of (S)-1-(4-fluoro-benzoyl)-piperidine-3-carboxylic acid (4-fluoro-phenyl)-amide as a white solid.

Yield: 82%; mp=163-164° C.; $[\alpha]_D^{20}$=+54.7° (c=0.995, CHCl$_3$); LCMS (Tr): 6.68 min (Method A); MS (ES+) gave m/z: 345.0.

$^1$H-NMR (CDCl$_3$, 333 K, 300 MHz), δ (ppm): 8.28 (s br, 1H); 7.56 (dd, 2H); 7.41 (dd, 2H); 7.09 (dd, 2H); 7.01 (dd, 2H); 4.05 (m br, 1H); 3.89 (dd, 1H); 3.65 (m, br, 1H); 3.40 (m br, 1H); 2.63 (m, 1H); 2.26 (m, 1H); 1.95 (m, 1H); 1.64 (m, 1H); 1.56 (m, 1H).

Example 63

(S)-1-(4-Fluoro-benzoyl)-piperidine-3-carboxylic acid (4-fluoro-phenyl)-methyl-amide

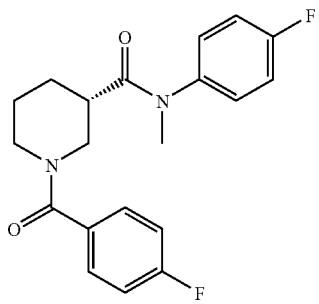

63(A) (S)-3-[(4-Fluoro-phenyl)-methyl-carbamoyl]-piperidine-1-carboxylic acid tert-butyl ester A mixture of S-1-Boc-piperidine-3-carboxylic acid (0.3 g, 1.30 mmol), EDCI.HCl (0.376 g, 1.96 mmol), HOBT (0.198 g, 1.30 mmol) in dioxane (4 mL) was stirred at R.T. for 1 h, under nitrogen atmosphere. N-Methyl-4-fluoro-aniline (164 mg, 1.30 mmol) was then added and the reaction mixture was heated at 80° C. for 2 h and then kept under stirring at room temperature for 2 days. The solvent was evaporated under reduced pressure and the residue was diluted with water and ethyl acetate. The phases were separated, the organic layer was washed with Na$_2$CO$_3$ 2M (aq.), dried over sodium sulphate and concentrated under reduced pressure. The crude was purified by filtration through a silica gel cartridge (silica gel: 10 g, eluent gradient: from petroleum ether/ethyl acetate 9/1 to petroleum ether/ethyl acetate 7/3) to provide 0.209 g of (S)-3-[(4-Fluoro-phenyl)-methyl-carbamoyl]-piperidine-1-carboxylic acid tert-butyl ester.

Yield: 47%; LCMS (Tr): 7.0 min (Method A); MS (ES+) gave m/z: 337.2.

$^1$H-NMR (CDCl$_3$, 300 MHz), δ (ppm): 7.22-7.07 (m, 4H); 4.00 (m, 2H); 3.22 (s, 3H); 2.89 dd, 1H); 2.63 (m, 1H); 2.27 (m, 1H); 1.78-1.65 (m, 2H); 1.61-1.50 (m, 2H); 1.40 (s, 9H).

63(B) (S)-Piperidine-3-carboxylic acid (4-fluoro-phenyl)-methyl-amide hydrochloride To a cooled solution of (S)-3-[(4-fluoro-phenyl)-methyl-carbamoyl]-piperidine-1-carboxylic acid tert-butyl ester (0.205 g, 0.61 mmol) in dichloromethane (4 mL) was added dropwise 3 mL of HCl 4N (dioxane solution) and the solution was stirred at R.T. for 1 h. The solvent was evaporated under reduced pressure to give the title compound as a white solid (0.16 g).

Yield: 96%.

LCMS (Tr): 5.37 min (Method A); MS (ES+) gave m/z: 237.1.

$^1$H-NMR (DMSO+TFA, 333 K, 300 MHz), δ (ppm): 8.98-8.45 (m, 2H); 7.43 (dd, 2H); 7.28 (dd, 2H); 3.16 (s, 3H); 3.16-2.67 (m, 5H); 1.80-1.34 (m, 4H).

63(C) (S)-1-(4-Fluoro-benzoyl)-piperidine-3-carboxylic acid (4-fluoro-phenyl)-methyl-amide 4-Fluorobenzoyl chloride (47 mL, 0.40 mmol) was added at 0° C. to a solution of (S)-piperidine-3-carboxylic acid (4-fluoro-phenyl)-methyl-amide hydrochloride (0.11 g, 0.40 mmol) and triethylamine (112 mL, 0.80 mmol) in dichloromethane (3 mL), under nitrogen atmosphere. The reaction mixture was kept under stirring at R.T. for 2 h, the solvent was evaporated and the residue was diluted with water and ethyl acetate. The phases were separated and the organic layer was washed with HCl 1N (10 mL), with Na$_2$CO$_3$ 2M (aq.) (10 mL) and with brine (10 mL). The organic layer was dried over sodium sulphate and concentrated under reduced pressure to give 0.121 g of (S)-1-(4-fluoro-benzoyl)-piperidine-3-carboxylic acid (4-fluoro-phenyl)-methyl-amide as a gummy solid.

Yield: 84%; [α]$_D^{20}$=+48.9° (c=1.020, CHCl$_3$); LCMS (Tr): 6.61 min (Method A); MS (ES+) gave m/z: 359.1.

$^1$H-NMR (CDCl$_3$, 333 K, 300 MHz), δ (ppm): 7.28 (dd, 2H); 7.13-7.00 (m, 6H); 4.06 (m br, 2H); 3.20 (s, 3H); 3.17 (m, 1H); 2.89 (m, 1H); 2.40 (m, 1H); 1.94-1.66 (m, 3H); 1.28 (m, 1H).

Example 64

(E)-3-(4-Fluoro-phenyl)-1-{(S)-3-[3-(4-fluoro-phenyl)-[1,2,4]oxadiazol-5-yl]-piperidin-1-yl}-propenone

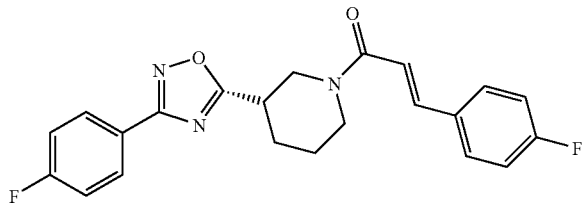

The compound was prepared following the procedure described in the Example 36, using 4-fluorocinnamic acid as the acid of choice and S-3-[3-(4-fluoro-phenyl)-[1,2,4]oxadiazol-5-yl]-piperidine hydrochloride (prepared as described in the Example 12). (E)-3-(4-Fluoro-phenyl)-1-{(S)-3-[3-(4-fluoro-phenyl)-[1,2,4]oxadiazol-5-yl]-piperidin-1-yl}-propenone was obtained pure after trituration from diethyl ether.

Yield: 77% (white solid); mp=137-139° C.; [α]$_D^{20}$=+191.7° (c=1.49, CHCl$_3$); LCMS (Tr): 7.62 min (Method A); MS (ES+) gave m/z: 396.1.

$^1$H-NMR (CDCl$_3$, 300 MHz), δ (ppm): 8.06 (dd, 2H); 7.63 (d, 1H); 7.50 (dd, 2H); 7.13 (dd, 2H); 7.06 (dd, 2H); 6.87 (d, 1H); 4.52 (m, 1H); 4.08 (ddd, 1H); 3.59 (m, 1H); 3.37 (ddd, 1H); 3.24 (m, 1H); 2.33 (m, 1H); 2.07 (m, 1H); 1.93 (m, 1H); 1.78-1.62 (m, 1H).

Example 65

1-(4-{(S)-3-[3-(4-Fluoro-phenyl)-[1,2,4]oxadiazol-5-yl]-piperidine-1-carbonyl}-piperidin-1-yl)-ethanone

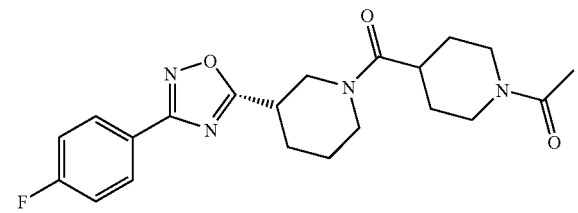

The compound was prepared following the procedure described in the Example 36, using 1-acetylpiperidine-4-carboxylic acid as the acid of choice and S-3-[3-(4-fluoro-phenyl)-[1,2,4]oxadiazol-5-yl]-piperidine hydrochloride (prepared as described in the Example 12). 1-(4-{(S)-3-[3-(4-Fluoro-phenyl)-[1,2,4]oxadiazol-5-yl]-piperidine-1-carbonyl}-piperidin-1-yl)-ethanone was obtained pure after flash chromatography (silica gel, eluent: DCM/MeOH/NH$_4$OH 98/2/0.2).

Yield: 57% (yellow gummy solid); [α]$_D^{20}$=+88.3° (c=2.23, CHCl$_3$); LCMS (Tr): 6.5 min (Method A); MS (ES+) gave m/z: 401.2.

$^1$H-NMR (CDCl$_3$+D$_2$O, 330 K, 300 MHz), δ (ppm): 8.06 (dd, 2H); 7.15 (dd, 2H); 4.68-3.73 (m, 5H); 3.65-2.97 (m, 3H); 2.80 (m, 2H); 2.29 (m, 1H); 2.13-1.56 (m, 10H).

Example 66

{(S)-3-[3-(4-Fluoro-phenyl)-[1,2,4]oxadiazol-5-yl]-piperidin-1-yl}-thiophen-3-yl-methanone

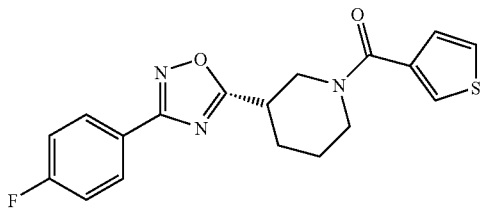

The compound was prepared following the procedure described in the Example 36, using thiophene-3-carboxylic acid as the acid of choice and S-3-[3-(4-fluoro-phenyl)-[1,2,4]oxadiazol-5-yl]-piperidine hydrochloride (prepared as described in the Example 12). {(S)-3-[3-(4-Fluoro-phenyl)-[1,2,4]oxadiazol-5-yl]-piperidin-1-yl}-thiophen-3-yl-methanone was obtained pure after flash chromatography (silica gel, eluent: DCM/MeOH 99.5/0.5).

Yield: 57% (gummy solid); $[\alpha]_D^{20}$=+79.8° (c=0.9, CHCl$_3$); LCMS (Tr): 7.19 min (Method A); MS (ES+) gave m/z: 358.1.

$^1$H-NMR (CDCl$_3$, 300 MHz), δ (ppm): 8.07 (dd, 2H); 7.54 (dd, 1H); 7.34 (dd, 1H); 7.20 (dd, 1H); 7.15 (dd, 2H); 4.53 (m, 1H); 4.11 (m, 1H); 3.51 (dd, 1H); 3.32-3.19 (m, 2H); 2.35 (m, 1H); 2.09-1.87 (m, 2H); 1.77-1.61 (m, 1H).

Example 67

{(S)-3-[3-(4-Fluoro-phenyl)-[1,2,4]oxadiazol-5-yl]-piperidin-1-yl}-(4-imidazol-1-yl-phenyl)-methanone

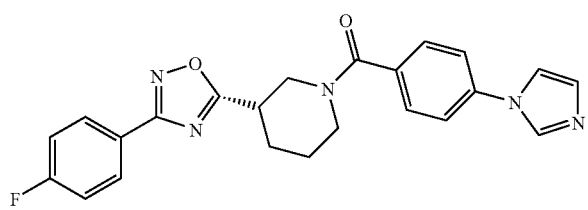

The compound was prepared following the procedure described in the Example 36, using 4-(1H-imidazol-1-yl)benzoic acid as the acid of choice and S-3-[3-(4-fluoro-phenyl)-[1,2,4]oxadiazol-5-yl]-piperidine hydrochloride (prepared as described in the Example 12). {(S)-3-[3-(4-Fluoro-phenyl)-[1,2,4]oxadiazol-5-yl]-piperidin-1-yl}-(4-imidazol-1-yl-phenyl)-methanone was obtained pure after flash chromatography (silica gel, eluent: DCM/MeOH/NH$_4$OH 98.5/1.5/0.15).

Yield: 64% (off-white solid); $[\alpha]_D^{20}$=+125.7° (c=1.707, CHCl$_3$); LCMS (Tr): 6.66 min (Method A); MS (ES+) gave m/z: 418.1.

$^1$H-NMR (CDCl$_3$, 300 MHz), δ (ppm): 8.19 (m br, 1H); 8.07 (dd, 2H); 7.59 (d, 2H); 7.49 (d, 2H); 7.32 (m, 2H); 7.16 (dd, 2H); 4.42 (m, 1H); 3.99 (m, 1H); 3.59 (dd, 1H); 3.39-3.21 (m, 2H); 2.36 (m, 1H); 2.14-1.90 (m, 2H); 1.72 (m, 1H).

Example 68

(4-Fluoro-phenyl)-[3-(5-phenyl-tetrazol-2-yl)-piperidin-1-yl]-methanone

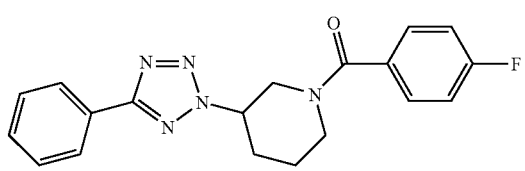

68(A) (4-Fluoro-phenyl)-(3-hydroxy-piperidin-1-yl)-methanone

A mixture of 3-hydroxypiperidine (0.6 g, 5.93 mmol), 4-fluorobenzoic acid (0.83 g, 5.93 mmol), HOBT (0.8 g, 5.93 mmol), EDCI.HCl (1.7 g, 8.9 mmol) and dry triethylamine (1.66 mL, 11.86 mmol) in dry dichloromethane (30 mL) was kept under stirring overnight at ambient temperature, under nitrogen atmosphere. HCl 1N (30 mL) was then added and the phases separated. The organic layer was washed with HCl 1N (30 mL), with NaOH 1N (30 mL×2 times), then with water (30 mL). Evaporation of the organic solvent afforded (4-fluoro-phenyl)-(3-hydroxy-piperidin-1-yl)-methanone as a white oil (0.7 g).

Yield: 53%; LCMS (Tr): 5.49 min (Method A); MS (ES+) gave m/z: 224.1.

$^1$H-NMR (CDCl$_3$, 300 MHz), δ (ppm): 7.43 (dd, 2H); 7.08 (dd, 2H); 3.83 (m, 1H); 3.73 (m, 1H); 3.56 (m, 1H); 3.43 (m, 2H); 1.99-1.79 (m, 2H); 1.74-1.42 (m, 2H).

68(B) (4-Fluoro-phenyl)-[3-(5-phenyl-tetrazol-2-yl)-piperidin-1-yl]-methanone To a solution of (4-fluoro-phenyl)-(3-hydroxy-piperidin-1-yl)-methanone (0.2 g, 0.89 mmol) in dry tetrahydrofuran (8 mL), triphenylphosphine (0.235 g, 0.89 mmol) was added in one portion at 0° C., under nitrogen atmosphere. Diisopropyl-azadicarboxylate (DIAD, 175 uL, 0.89 mmol) was added dropwise to the reaction mixture while cooling at 0° C. The reaction mixture was allowed to warm at room temperature and stirred at R.T. for 24 h Triphenylphosphine (0.118 g, 0.45 mmol) and diisopropyl-azadicarboxylate (DIAD, 87 uL, 0.45 mmol) were then added at 0° C. and the reaction mixture was stirred at R.T. overnight. The solvent was evaporated under reduced pressure to give a yellow oil which was purified by flash chromatography (silica gel, eluent: hexane/ethyl acetate 6/4). (4-Fluoro-phenyl)-[3-(5-phenyl-tetrazol-2-yl)-piperidin-1-yl]-methanone was obtained as a thick oil (132 mg).

Yield: 42%; LCMS (Tr): 7.04 min (Method A); MS (ES+) gave m/z: 352.1.

$^1$H-NMR (CDCl$_3$, 300 MHz, 323 K), δ (ppm): 8.12 (dd, 2H); 7.55-7.35 (m, 5H); 7.07 (dd, 2H); 4.90 (m, 1H); 4.50 (m, 1H); 4.33-3.69 (m, 3H); 3.36 (m, 1H); 2.57-2.28 (m, 1H); 2.14-1.96 (m, 1H); 1.84-1.66 (m, 1H).

Example 69

(4-Fluoro-phenyl)-[(S)-3-(3-phenyl-[1,2,4]oxadiazol-5-yl)-piperidin-1-yl]-methanone

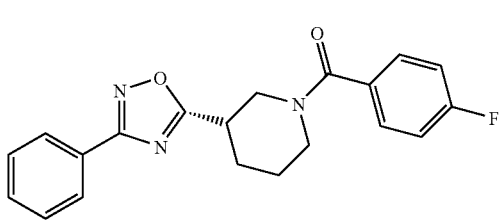

Example 70

(3,4-Difluoro-phenyl)-[(S)-3-(3-phenyl-[1,2,4]oxadiazol-5-yl)-piperidin-1-yl]-methanone

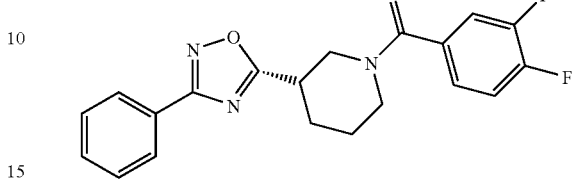

The compound was prepared following the procedure described in the Example 46(C), starting from S-3-(3-Phenyl-[1,2,4]oxadiazol-5-yl)-piperidine hydrochloride and using 3,4-difluorobenzoyl chloride as the acyl chloride of choice. (3,4-Difluoro-phenyl)-[(S)-3-(3-phenyl-[1,2,4]oxadiazol-5-yl)-piperidin-1-yl]-methanone was obtained pure after purification by chromatography through silica gel cartridge (eluent gradient: from hexane/ethyl acetate 8/2 to hexane/ethyl acetate 6/4).

Yield: 31% (white solid); mp=149-151° C.; $[\alpha]_D^{20}$=+ 111.7° (c=0.55, $CHCl_3$); LCMS (Tr): 7.33 min (Method A); MS (ES+) gave m/z: 370.2.

$^1$H-NMR ($CDCl_3$, 300 MHz, 323 K), δ (ppm): 8.06 (dd, 2H); 7.53-7.42 (m, 3H); 7.35-7.11 (m, 3H); 4.36 (m, 1H); 3.93 (m, 1H); 3.57 (dd, 1H); 3.40-3.16 (m, 2H); 2.(m, 1H); 2.14-1.56 (m, 3H).

69(A) S-3-(3-Phenyl-[1,2,4]oxadiazol-5-yl)-piperidine-1-carboxylic acid tert-butyl ester The compound was prepared following the procedure described in the Example 46(A), starting from benzonitrile. S-3-(3-Phenyl-[1,2,4]oxadiazol-5-yl)-piperidine-1-carboxylic acid tert-butyl ester was obtained as a beige oil which was used for the next step without further purification (Yield: 85%).

LCMS (Tr): 7.83 min (Method A); MS (ES+) gave m/z: 330.2.

69(B) S-3-(3-Phenyl-[1,2,4]oxadiazol-5-yl)-piperidine hydrochloride

The compound was prepared following the procedure described in the Example 46(B), starting from S-3-(3-phenyl-[1,2,4]oxadiazol-5-yl)-piperidine-1-carboxylic acid tert-butyl ester (yield: 100%).

69(C) (4-Fluoro-phenyl)-[(S)-3-(3-phenyl-[1,2,4]oxadiazol-5-yl)-piperidin-1-yl]-methanone The compound was prepared following the procedure described in the Example 46(C), starting from S-3-(3-phenyl-[1,2,4]oxadiazol-5-yl)-piperidine hydrochloride and using 4-fluorobenzoyl chloride as the acyl chloride of choice. (4-Fluoro-phenyl)-[(S)-3-(3-phenyl-[1,2,4]oxadiazol-5-yl)-piperidin-1-yl]-methanone was obtained pure after purification by chromatography through silica gel cartridge (eluent gradient: from hexane/ethyl acetate 8/2 to hexane/ethyl acetate 6/4).

Yield: 60% (White solid); mp=116-118° C.; $[\alpha]_D^{20}$=+ 99.3° (c=0.64, $CHCl_3$); LCMS (Tr): 7.21 min (Method A); MS (ES+) gave m/z: 352.2.

$^1$H-NMR ($CDCl_3$, 300 MHz, 323 K), δ (ppm): 8.06 (m, 2H); 7.54-7.37 (m, 5H); 7.08 (m, 2H); 4.42 (m, 1H); 3.99 (m, 1H); 3.52 (dd, 1H); 3.26 (ddd, 2H); 2.34 (m, 1H); 2.12-1.59 (m, 3H)

Example 71

(4-Fluoro-phenyl)-{(S)-3-[3-(4-nitro-phenyl)-[1,2,4]oxadiazol-5-yl]-piperidin-1-yl}-methanone

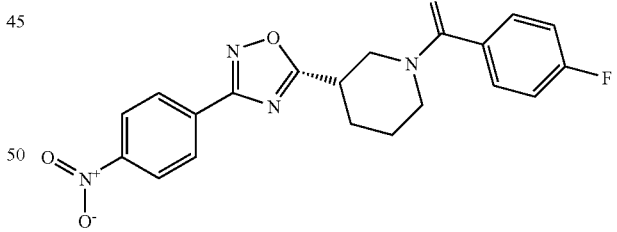

71(A) S-3-[3-(4-Nitro-phenyl)-[1,2,4]oxadiazol-5-yl]-piperidine-1-carboxylic acid tert-butyl ester The compound was prepared following the procedure described in the Example 46(A), starting from 4-nitrobenzonitrile. S-3-[3-(4-Nitro-phenyl)-[1,2,4]oxadiazol-5-yl]-piperidine-1-carboxylic acid tert-butyl ester was obtained as a yellow solid and used for the next step without further purification (Yield: 83%).

LCMS (Tr): 7.93 min (Method A); MS (ES+) gave m/z: 375.1.

71(B) S-3-[3-(4-Nitro-phenyl)-[1,2,4]oxadiazol-5-yl]-piperidine hydrochloride The compound was prepared following the procedure described in the Example 46(B), starting from S-3-[3-(4-Nitro-phenyl)-[1,2,4]oxadiazol-5-yl]-piperidine-1-carboxylic acid tert-butyl ester (yield: 100%).

71(C) (4-Fluoro-phenyl)-{(S)-3-[3-(4-nitro-phenyl)-[1,2,4]oxadiazol-5-yl]-piperidin-1-yl}-methanone The compound was prepared following the procedure described in the Example 46(C), starting from S-3-[3-(4-Nitro-phenyl)-[1,2,4]oxadiazol-5-yl]-piperidine hydrochloride and using 4-fluorobenzoyl chloride as the acyl chloride of choice. (4-Fluoro-phenyl)-{(S)-3-[3-(4-nitro-phenyl)-[1,2,4]oxadiazol-5-yl]-piperidin-1-yl}-methanone was obtained pure after purification by chromatography through silica gel cartridge (eluent gradient: from hexane/ethyl acetate 8/2 to hexane/ethyl acetate 6/4).

Yield: 48% (yellow solid); mp=162-164° C.; $[\alpha]_D^{20}$=+111.5° (c=0.59, CHCl$_3$); LCMS (Tr): 7.29 min (Method A); MS (ES+) gave m/z: 397.1.

$^1$H-NMR (CDCl$_3$, 300 MHz, 323 K), δ (ppm): 8.29 (dd, 4H); 7.43 (dd, 2H); 7.10 (dd, 2H); 4.47 (m, 1H); 3.98 (m, 1H); 3.54 (dd, 1H); 3.37-3.19 (m, 2H) 2.36 (m, 1H); 2.11-1.57 (m, 3H).

Example 72

(3,4-Difluoro-phenyl)-{(S)-3-[3-(4-nitro-phenyl)-[1,2,4]oxadiazol-5-yl]-piperidin-1-yl}-methanone

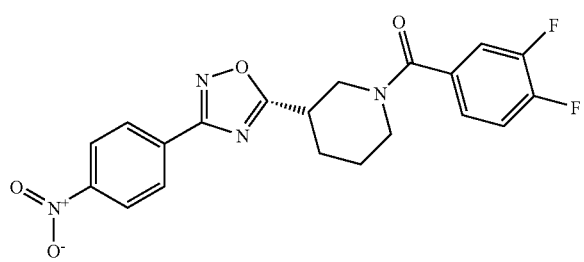

The compound was prepared following the procedure described in the Example 46(C), starting from S-3-[3-(4-Nitro-phenyl)-[1,2,4]oxadiazol-5-yl]-piperidine hydrochloride using 3,4-difluorobenzoyl chloride as the acyl chloride of choice. (3,4-Difluoro-phenyl)-{(S)-3-[3-(4-nitro-phenyl)-[1,2,4]oxadiazol-5-yl]-piperidin-1-yl}-methanone was obtained pure after purification by chromatography through silica gel cartridge (eluent gradient: from hexane/ethyl acetate 8/2 to hexane/ethyl acetate 6/4).

Yield: 44% (yellow solid); mp=138-140° C.; $[\alpha]_D^{20}$=+112.4° (c=0.50, CHCl$_3$); LCMS (Tr): 7.39 min (Method A); MS (ES+) gave m/z: 415.1.

$^1$H-NMR (CDCl$_3$, 300 MHz, 328 K), δ (ppm): 8.38-8.19 (m, 4H); 7.35-7.10 (m, 3H); 4.41 (m, 1H); 3.92 (m, 1H); 3.58 (dd, 1H); 3.32 (m, 2H); 2.48-1.59 (m, 4H).

Pharmacology:

The compounds provided in the present invention are positive allosteric modulators of mGluR5. As such, these compounds do not appear to bind to the orthosteric glutamate recognition site, and do not activate the mGluR5 by themselves. Instead, the response of mGluR5 to a concentration of glutamate or mGluR5 agonist is increased when compounds of Formula I are present. Compounds of Formula I are expected to have their effect at mGluR5 by virtue of their ability to enhance the function of the receptor.

Example A mGluR5 Binding Assay on Rat Brain Membrane Preparation

Activity of compounds of the invention was examined following a radioligand binding technique using rat cortical membranes and tritiated 2-methyl-6-(phenylethynyl)-pyridine ([$^3$H]-MPEP) as a ligand following similar methods than those described in Gasparini et al. (2002) Bioorg. Med. Chem. Lett 12: 407-409 and in Anderson et al. (2002) J. Pharmacol. Exp. Ther. 303: 1044-1051.

Membrane Preparation:

Cortices were dissected out from brains of 200-300 g Sprague-Dawley rats (Charles River Laboratories, L'Arbresle, France). Tissues were homogenized in 10 volumes (vol/wt) of ice-cold 50 mM HEPES-NaOH (pH 7.4) using a Polytron disrupter (Kinematica AG, Luzern, Switzerland) and centrifuged for 30 min at 40,000 g. (4° C.). The supernatant was discarded and the pellet washed twice by resuspension in 10 volumes 50 mM HEPES-NaOH. Membranes were then collected by centrifugation and washed before final resuspension in 10 volumes of 20 mM HEPES-NaOH, pH 7.4. Protein concentration was determined by the Bradford method (Bio-Rad protein assay, Reinach, Switzerland) with bovine serum albumin as standard.

[$^3$H]-MPEP Binding Experiments:

Membranes were thawed and resuspended in binding buffer containing 20 mM HEPES-NaOH, 3 mM MgCl$_2$, 3 mM CaCl$_2$, 100 mM NaCl, pH 7.4. Competition studies were carried out by incubating for 1 h at 4° C.: 3 nM [$^3$H]-MPEP (39 Ci/mmol, Tocris, Cookson Ltd, Bristol, U.K.), 50 μg membrane and a concentration range of 0.003 nM-30 μM of compounds, for a total reaction volume of 300 μl. The non-specific binding was defined using 30 μM MPEP. Reaction was terminated by rapid filtration over glass-fiber filter plates (Unifilter 96-well GF/B filter plates, Perkin-Elmer, Schwerzenbach, Switzerland) using 4×400 μl ice cold buffer using cell harvester (Filtermate, Perkin-Elmer, Downers Grove, USA). Radioactivity was determined by liquid scintillation spectrometry using a 96-well plate reader (TopCount, Perkin-Elmer, Downers Grove, USA).

Data Analysis:

The inhibition curves were generated using the Prism GraphPad program (Graph Pad Software Inc, San Diego, USA). IC$_{50}$ determinations were made from at least three independent experiments and data were obtained from 8 point-concentration response curves using a non linear regression analysis.

Compounds within the present invention have the ability to inhibit [$^3$H]-MPEP binding in rat cortical membrane with IC$_{50}$ less than about 100 uM, or less than about 30 uM and 10 uM and preferentially less than about 3 uM.

Example B mGluR5 Assay on Rat Cultured Cortical Astrocytes

Under exposure to growth factors (basic fibroblast growth factor, epidermal growth factor), rat cultured astrocytes express group I-Gq coupled mGluR transcripts, namely mGluR5, but none of the splice variants of mGluR1, and as a consequence, a functional expression of mGluR5 receptors (Miller et al. (1995) J. Neurosci. 15:6103-9): The stimulation of mGluR5 receptors with selective agonist CHPG and the fall blockade of the glutamate-induced phosphoinositide (PI) hydrolysis and subsequent intracellular calcium mobilization with specific antagonist as MPEP confirm the unique expression of mGluR5 receptors in this preparation. This preparation was established and used in order to assess the properties of the compounds of the present invention to increase the $Ca^{2+}$ mobilization-induced by glutamate without showing any significant activity when applied in the absence of glutamate.

Primary Cortical Astrocytes Culture:

Primary glial cultures were prepared from cortices of Sprague-Dawley 15 days old embryos using a modification of methods described by Mc Carthy and de Vellis (1980) J. Cell Biol. 85:890-902 and Miller et al. (1995) J. Neurosci. 15(9): 6103-9. The cortices were dissected and then dissociated by trituration in a sterile buffer containing 5.36 mM KCl, 0.44 mM $NaHCO_3$, 4.17 mM $KH_2PO_4$, 137 mM NaCl, 0.34 mM $NaH_2PO_4$, 1 g/L glucose. The resulting cell homogenate was plated onto poly-D-lysine precoated T75 flasks (BIOCOAT, Becton Dickinson Biosciences, Erembodegem, Belgium) in Dubelcco's Modified Eagle's Medium (D-MEM GlutaMAX™ I, Invitrogen, Basel, Switzerland) buffered with 25 mM HEPES and 22.7 mM $NaHCO_3$, and supplemented with 4.5 g/L glucose, 1 mM pyruvate and 15% fetal calf serum (FCS, Invitrogen, Basel, Switzerland), penicillin and streptomycin and incubated at 37° C. with 5% $CO_2$. For subsequent seeding, the FCS supplementation was reduced to 10%. After 12 days, cells were subplated by trypsinisation onto poly-D-lysine precoated 384-well plates at a density of 20.000 cells per well in culture buffer supplemented with 5 ng/ml βFGF (basic fibroblast growth factor) (Invitrogen, Basel, Switzerland) and 10 ng/ml EGF (epidermal growth factor) (Invitrogen, Basel, Switzerland).

$Ca^{2+}$ Mobilization Assay Using Rat Cortical Astrocytes:

After 2 days incubation, cells were washed with Assay buffer containing: 142 mM NaCl, 6 mM KCl, 1 mM $Mg_2SO_4$, 1 mM $CaCl_2$, 20 mM HEPES, 1 g/L glucose, 0.125 mM sulfinpyrazone, pH 7.4. After 60 min of loading with 4 uM Fluo-4 (TefLabs, Austin, Tex.), the cells were washed three times with 50 oil of PBS Buffer and resuspended in 45 μl of Assay Buffer. The plates were then transferred to a Fluorometric Imaging Plate Reader (FLIPR, Molecular Devices, Sunnyvale, Calif.) for the assessment of intracellular calcium flux. After monitoring the fluorescence for 15 s in order to establish a baseline, DMSO solutions containing various concentrations of representative compounds of the present invention diluted in Assay Buffer (15 μl of 4× dilutions) were added to the cell plate in absence or in presence of 1 μM of glutamate: 1 μM glutamate, the concentration that gives 20% of the maximal response of glutamate ($EC_{20}$) in our experimental conditions and in accordance to published data, was the concentration used to detect the positive allosteric modulator properties of the compounds from the present invention. The final DMSO concentration in the assay was 0.3%. In each experiment, fluorescence was then monitored as a function of time for 3 minutes and the data analyzed using Microsoft Excel and GraphPad Prism. Each data point was also measured two times.

Data Analysis:

The concentration-response curves of representative compounds of the present invention in the presence of $EC_{20}$ of glutamate were generated using the Prism GraphPad program (Graph Pad Software Inc, San Diego, USA). The curves were fitted to a four-parameter logistic equation (Y=Bottom+(Top−Bottom)/(1+10^((LogEC50−X)*HillSlope)) permitting the determinations of $EC_{50}$ values. Each curve was performed using triplicate sample per data point and 8 concentrations.

Data presented in the FIG. 1 represent the ability of 3 μM of the examples # 12, # 55 and # 56 to increase the stimulation induced by 1 μM of glutamate in primary cortical mGluR5-expressing cell culture. Examples # 12, # 55 and # 56 have no statistically significant agonistic activity when tested in the absence of glutamate, as compared to buffer value.

Each bargraph is the mean and S.E.M of triplicate data points and is representative of three independent experiments FIG. 1 shows an increase of 1 μM glutamate-induced $Ca^{2+}$ mobilization in rat cultured astrocytes in the presence of 3 μM of examples # 12, 55 and 56 of the present invention.

The results shown in Example A and Example B demonstrate that the compounds described in the present invention do not have an effect per se on mGluR5. Instead, when compounds are added together with an mGluR5 agonist like glutamate or CHPG, the effect measured is significantly potentiated compared to the effect of the agonist alone at the same concentration. In addition, the compounds of the present invention have the ability to inhibit the binding of a mGluR5 negative allosteric modulator in rat cortical membrane preparation, a property recently described for 3,3'-Difluorobenzaldazine (DFB), another mGluR5 positive allosteric modulator (O'Brien J A et al (2003) Mol Pharmacol. 64:731-40). In addition, DFB is not able to inhibit the binding of [3H]-quisqualate to the orthosteric glutamate site (O'Brien J A et al (2003) Mol Pharmacol. 64:731-40). Taken together, these data indicate that the compounds of the present invention are positive allosteric modulator of mGluR5 receptor in native preparation and do not appear to bind to the orthosteric binding site of the receptor.

Thus, the positive allosteric modulators provided in the present invention are expected to increase the effectiveness of glutamate or mGluR5 agonists at mGluR5 receptor. Therefore, these positive allosteric modulators are expected to be useful for treatment of various neurological and psychiatric disorders associated with glutamate dysfunction described to be treated herein and others that can be treated by such positive allosteric modulators.

Example C

Animal Models of Schizophrenia

Phencyclidine (PCP) Model of Schizophrenia

PCP-induced increases in locomotor ambulation are a widely accepted animal model of schizophrenia. This model is based on the evidence that phencyclidine induces a schizophrenia-like syndrome in humans including increased motor behaviors, disruption of cognition and impairment of working memory (Steinpreis R E (1996) Behav Br Res. 74:45-55; Abi-Saab et al. (1998) Pharmacopsychiatry, 31:104-109). Further, it has also been shown that antipsychotic drugs that are effective in the treatment of schizophrenia reduce the locomotor activating effect of PCP (Gleason & Shannon (1997) Psychopharmacology, 129:79-84). These results demonstrate that locomotor activation induced by PCP is a useful model for screening of compounds which may be useful in the treatment of schizophrenia Amphetamine Model of Schizophrenia Amphetamine-induced increases in locomotor ambulation are well known and are widely used as a model of the positive symptoms of schizophrenia. This model is based on evidence that amphetamine increases motor behaviors and can induce a psychotic state in humans (Yui et al. (2000) Ann NY Acad Sci 914:1-12). Further, it is well known that amphetamine-induced increases in locomotor activity are blocked by antipsychotics drugs that are effective in the treatment of schizophrenia (Arnt (1995) Eur J Pharmacol 283:55-62). These results demonstrate that locomotor activation induced by amphetamine is a useful model for screening of compounds which may be useful in the treatment of schizophrenia.

Subjects: The present studies were performed in accordance with the animal care and use policies of Addex Pharmaceuticals and the laws and directives of Switzerland governing the care and use of animals. Male C57BL6/j mice (20-30 g) 7 weeks of age at the time of delivery were group housed in a temperature and humidity controlled facility on a 12 hour light/dark cycle for at least 7 days before use. Mice had access to food and water ad libitum except during locomotor activity experiments.

Assessment of locomotor (ambulatory) activity: The effects of compounds on PCP- or amphetamine-induced locomotor activation in mice were tested. Locomotor activity of mice was tested in white plastic boxes 35 cm×35 cm square with walls 40 cm in height. Locomotor activity (ambulations) was monitored by a videotracking system (VideoTrack, Viewpoint, Champagne au Mont d'Or, France) that recorded the ambulatory movements of mice. Mice were näive to the apparatus prior to testing. On test days, test compounds (10, 30, 50 or 100 mg/kg i.p. (intraperitoneal)) or vehicle were administered 120 minutes before the PCP (5 mg/kg s.c.(subcutaneous)), amphetamine (3.0 mg/kg s.c.) or saline injection. Mice were placed into the locomotor boxes immediately after the PCP, amphetamine or saline vehicle injection and their locomotor activity, defined as the distance traveled in centimeters (cm), was measured for 60 minutes.

Compound administration: Compounds were prepared as a microsuspension in sterile water (60% of final volume) and Labrafil M1944 CS (apricot kernel oil—Gattefossé, Saint Priest, France) (40% of final volume) and administered in a volume of 10 ml/kg. Compound-vehicle-treated mice received the equivalent volume of vehicle solution i.p. in the absence of added compound. PCP hydrochloride (Sigma, Switzerland) was dissolved in saline and was administered at a dose of 5 mg/kg s.c. in a volume of 10 ml/kg. PCP-vehicle-treated mice received an equal volume of saline vehicle injected s.c. D-amphetamine sulfate (Amino AG, Neuenhof, Switzerland) was dissolved in saline and administered at a dose of 3.0 mg/kg s.c. in a volume of 10 ml/kg. D-amphetamine-vehicle-treated mice received an equivalent volume of saline vehicle injected s.c.

Statistical analyses: Statistical analyses were performed using GraphPad PRISM statistical software (GraphPad, San Diego, Calif., USA). Data were analyzed using one-way analysis of variance (ANOVA) followed by post-hoc Bonferroni-corrected multiple comparisons, where appropriate. The significance level was set at $p<0.05$.

Effect of Compounds on PCP-Induced Locomotor Activity in Mice

Figure 2:
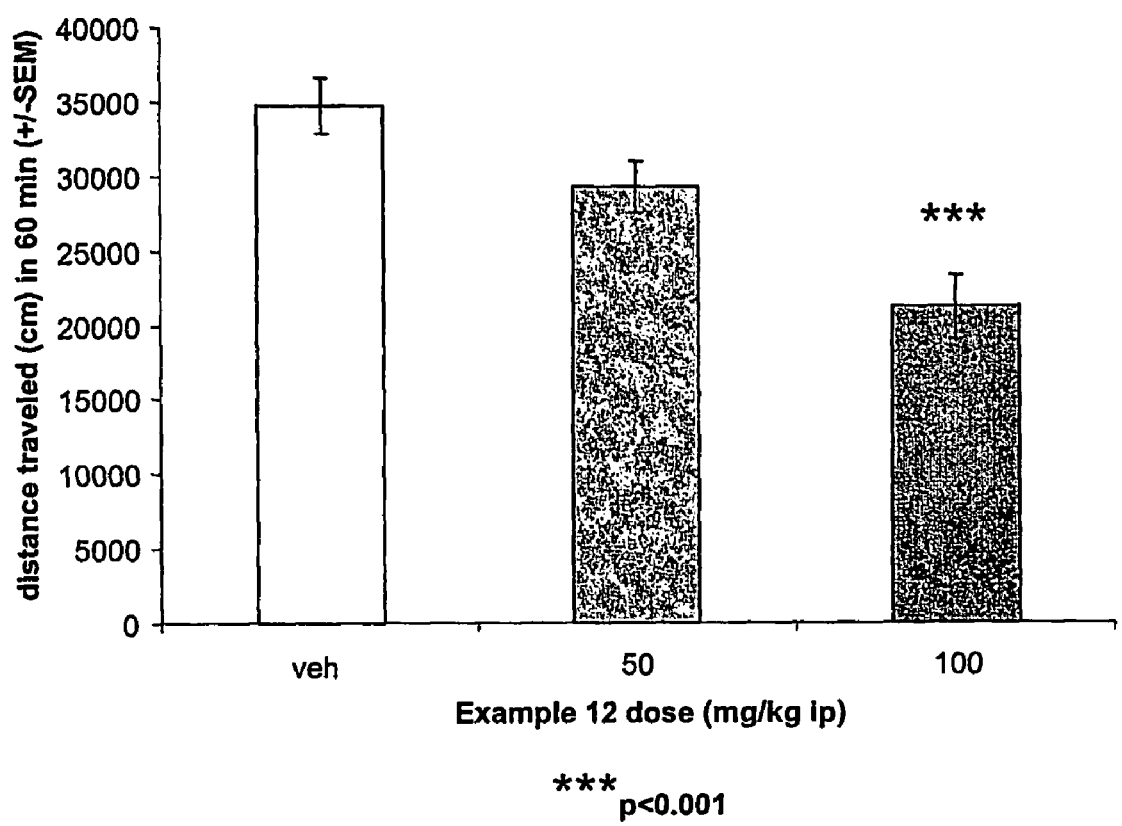
FIG. 2 shows the representative compound of the invention significantly attenuated the increase in locomotor activity induced by PCP (f=13.39, df=(2, 45), n=16/group) at a dose of 100 mg/kg ip.

Data from such an experiment using a representative compound is shown in FIG. 2.

FIG. 2 shows the representative compound of the invention significantly attenuated the increase in locomotor activity induced by PCP ($f=13.39$, $df=(2, 45)$, $n=16$/group) at a dose of 100 mg/kg ip.

Effect of Compounds on Amphetamine-Induced Locomotor Activity in Mice

Figure 3:
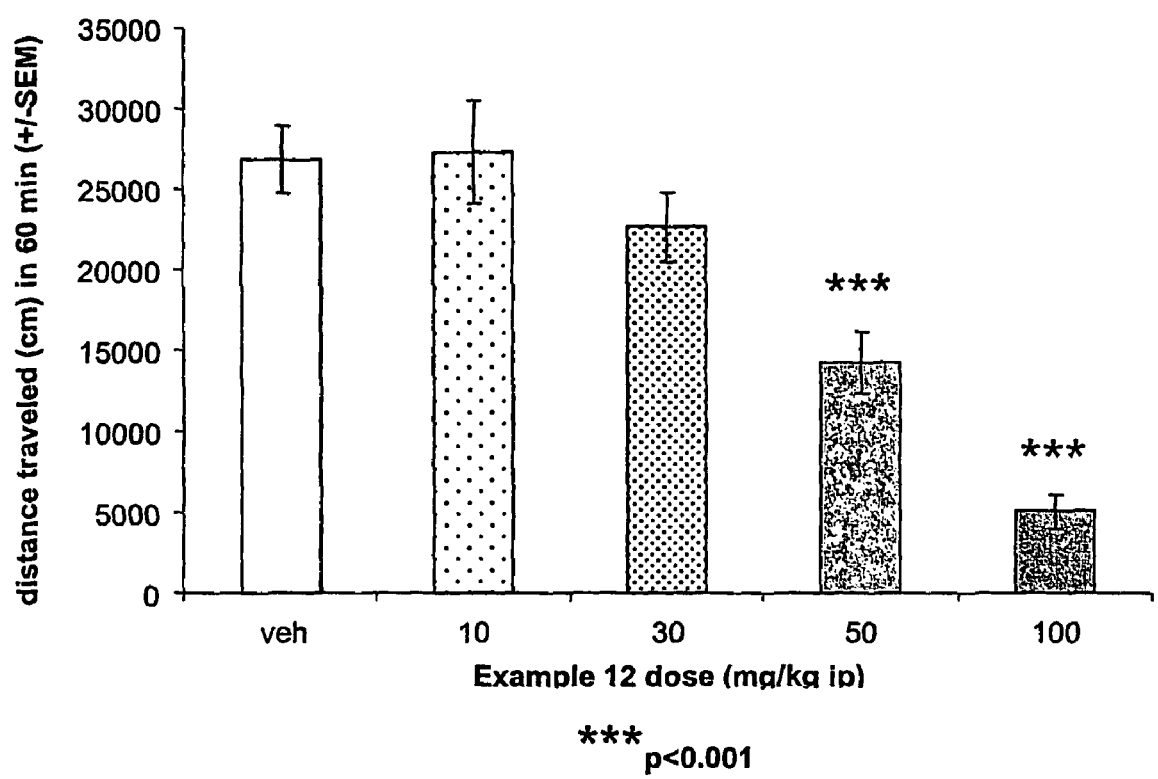
FIG. 3 shows the representative compound of the invention significantly attenuated the increase in locomotor activity induced by amphetamine (f=13.04, df=(4, 82) n=8-33 mice per group) at doses of 50 & 100 mg/kg ip.

Data from such an experiment using a representative compound is shown in FIG. 3.

FIG. 3 shows the representative compound of the invention significantly attenuated the increase in locomotor activity induced by amphetamine ($f=13.04$, $df=(4, 82)$ $n=8-33$ mice per group) at doses of 50 & 100 mg/kg ip.

Summary of in Vivo Data

The data presented above shows that representative compounds of Formula 12 significantly attenuate the hyperlocomotor effects of PCP and amphetamine, two widely accepted animal models of schizophrenia. These results support the potential of compounds of Formula I in the treatment of schizophrenia and related disorders.

The compounds of the present invention are allosteric modulators of mGluR5 receptors, they are useful for the production of medications, especially for the prevention or treatment of central nervous system disorders as well as other disorders modulated by this receptor.

The compounds of the invention can be administered either alone, or in combination with other pharmaceutical agents effective in the treatment of conditions mentioned above.

Formulation Examples

Typical examples of recipes for the formulation of the invention are as follows:

1) Tablets

| | |
|---|---|
| Compound of the example 12 | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

In this example, the compound of the example 12 can be replaced by the same amount of any of the described examples 1 to 72.

2) Suspension:

An aqueous suspension is prepared for oral administration so that each 1 milliliter contains 1 to 5 mg of one of the described example, 50 mg of sodium carboxymethyl cellulose, 1 mg of sodium benzoate, 500 mg of sorbitol and water ad 1 ml.

3) Injectable

A parenteral composition is prepared by stirring 1.5% by weight of active ingredient of the invention in 10% by volume propylene glycol and water.

4) Ointment

| | |
|---|---|
| Compound of the example 12 | 5 to 1000 mg |
| Stearyl alcohol | 3 g |
| Lanoline | 5 g |
| White petroleum | 15 g |
| Water | ad 100 g |

In this example, the compound 12 can be replaced by the same amount of any of the described examples 1 to 72.

Reasonable variations are not to be regarded as a departure from the scope of the invention. It will be obvious that the thus described invention may be varied in many ways by those skilled in the art.

The invention claimed is:
1. A compound selected from the group consisting of:
(S)-(4-Fluoro-phenyl)-{3-[3-(4-fluoro-phenyl)-[1,2,4]oxadiazol-5-yl]-piperidin-1-yl}-methanone;
(S)-(thiophen-2-yl)-{3-[3-(4-fluoro-phenyl)[1,2,4]oxadiazol-5-yl]-piperidin-1-yl}-methanone;
{(S)-3-[3-(4-Fluoro-phenyl)-[1,2,4]oxadiazol-5-yl]-piperidin-1-yl}-(4-methyl-2-pyrazin-2-yl-thiazol-5-yl)-methanone;
(2,4-Difluoro-phenyl)-{(S)-3-[3-(4-fluoro-phenyl)-[1,2,4]oxadiazol-5-yl]-piperidin-1-yl}-methanone;
{(S)-3-[3-(4-Fluoro-phenyl)-[1,2,4]oxadiazol-5-yl]-piperidin-1-yl}-(3,4,5-trifluoro-phenyl)-methanone;
{(S)-3-[3-(4-Fluoro-phenyl)-1,2,4-oxadiazol-5-yl]-piperidin-1-yl}-(5-pyridin-2-yl-thiophen-2-yl)-methanone;
Cyclopentyl-{(S)-3-[3-(4-fluoro-phenyl)-[1,2,4]oxadiazol-5-yl]-piperidin-1-yl}-methanone;
(3,4-Difluoro-phenyl)-{(S)-3-[3-(4-fluoro-phenyl)-[1,2,4]oxadiazol-5-yl]-piperidin-1-yl}-methanone;
Benzothiazol-6-yl-{(S)-3-[3-(4-fluoro-phenyl)-1,2,4-oxadiazol-5-yl]-piperidin-1-yl}-methanone;
(3,5-Dimethyl-isoxazol-4-yl)-{(S)-3-[3-(4-fluoro-phenyl)-[1,2,4]oxadiazol-5-yl]-piperidin-1-yl}-methanone;
(4-Fluoro-phenyl)-{(S)-3-[3-(2,4,6-trifluoro-phenyl)-[1,2,4]oxadiazol-5-yl]-piperidin-1-yl}-methanone;
{(S)-3-[3-(2,4-Difluoro-phenyl)-[1,2,4]oxadiazol-5-yl]-piperidin-1-yl}-(4-fluoro-phenyl)-methanone;
(4-Fluoro-phenyl)-[(S)-3-(3-p-tolyl-[1,2,4]oxadiazol-5-yl)-piperidin-1-yl]-methanone;
(4-Fluoro-phenyl)-{(S)-3-[3-(2-fluoro-phenyl)-[1,2,4]oxadiazol-5-yl]-piperidin-1-yl}-methanone;
(2-Fluoro-phenyl)-{(S)-3-[2-(3,4-difluoro-phenyl)-1,2,4]oxadiazol-5-yl]-piperidin-1-yl}-methanone;
{(S)-3-[3-(4-Fluoro-phenyl)-[1,2,4]oxadiazol-5-yl]-piperidin-1-yl}-thiophen-3-yl-methanone;
(4-Fluoro-phenyl)-[(S)-3-(3-phenyl-[1,2,4]oxadiazol-5-yl)-piperidin-1-yl]-methanone; and
(3,4-Difluoro-phenyl)-[(S)-3-(3-phenyl-[1,2,4]oxadiazol-5-yl)-piperidin-1-yl]-methanone;
or a pharmaceutically acceptable salt thereof.
2. A compound selected from the group consisting of:
{3-[3-(4-Methoxy-phenyl)-[1,2,4]oxadiazol-5-yl]-piperidin-1-yl}-phenyl-methanone;
{3-[3-(4-Fluoro-phenyl)-[1,2,4]oxadiazol-5-yl]-piperidin-1-yl}-phenyl-methanone;
(4-Fluoro-phenyl)-[3-(3-phenyl-[1,2,4]oxadiazol-5-yl)-piperidin-1-yl]-methanone;
(3-Fluoro-phenyl)-[3-(3-phenyl-[1,2,4]oxadiazol-5-yl)-piperidin-1-yl]-methanone;
(4-Fluoro-phenyl)-{3-[3-(3-fluoro-phenyl)-[1,2,4]oxadiazol-5-yl]-piperidin-1-yl}-methanone;
(3-Fluoro-phenyl)-{3-[3-(3-fluoro-phenyl)-[1,2,4]oxadiazol-5-yl]-piperidin-1-yl}-methanone;
(4-Fluoro-phenyl)-{3-[3-(4-fluoro-phenyl)-[1,2,4]oxadiazol-5-yl]-piperidin-1-yl}-methanone;
(3-Fluoro-phenyl)-{3-[3-(4-fluoro-phenyl)-[1,2,4]oxadiazol-5-yl]-piperidin-1-yl}-methanone;
(R)-(4-Fluoro-phenyl)-{3-[3-(4-fluoro-phenyl)-[1,2,4]oxadiazol-5-yl]-piperidin-1-yl}-methanone;
{(S)-3-[3-(4-Fluoro-phenyl)-[1,2,4]oxadiazol-5-yl]-piperidin-1-l}-(2-phenyl-thiazol-4-yl)-methanone;
{{(S)-3-[3-(4-Fluoro-phenyl)-[1,2,4]oxadiazol-5-yl]-piperidin-1-yl}-(2-methyl-6-trifluoromethyl-pyridin-3-yl)-methanone;
{(S)-3-[3-(4-Fluoro-phenyl)-[1,2,4]oxadiazol-5-yl]-piperidin-1-yl}-[1,2,3]thiadiazol-4-yl-methanone;
Benzothiazol-2-yl-{(S)-3-[3-(4-fluoro-phenyl)-[1,2,4]oxadiazol-5-yl]-piperidin-1-yl}-methanone;
{(S)-3-[3-(4-Fluoro-phenyl)-[1,2,4]oxadiazol-5-yl]-piperidin-1-yl}-(5-methyl-isoxazol-3-yl)-methanone;
(1,5-Dimethyl-1H-pyrazol-3-yl)-{(S)-3-[3-(4-fluoro-phenyl)-[1,2,4]oxadiazol-5-yl]-piperidin-1-yl}-methanone;
{(S)-3-[3-(4-Fluoro-phenyl)-[1,2,4]oxadiazol-5-yl]-piperidin-1-yl}-(4-trifluoromethyl-phenyl)-methanone;
4-{(S)-3-[3-(4-Fluoro-phenyl)-[1,2,4]oxadiazol-5-yl]-piperidine-1-carbonyl}-benzonitrile;
{(S)-3-[3-(4-Fluoro-phenyl)-[1,2,4]oxadiazol-5-yl]-piperidin-1-yl}-isoxazol-5-yl-methanone;
(3-Chloro-4-fluoro-phenyl)-{(S)-3-[3-(4-fluoro-phenyl)-[1,2,4]oxadiazol-5-yl]-piperidin-1-yl}-methanone;
{(S)-3-[3-(4-Fluoro-phenyl)-[1,2,4]oxadiazol-5-yl]-piperidin-1-yl}-(2-phenyl-2H-pyrazol-3-yl)-methanone;
{(S)-3-[3-(4-Fluoro-phenyl)-[1,2,4]oxadiazol-5-yl]-piperidin-1-yl}-(5-methyl-2-phenyl-2H-[1,2,3]triazol-4-yl)-methanone;
(4-Fluoro-3-methyl-phenyl)-{(S)-3-[3-(4-fluoro-phenyl)-[1,2,4]oxadiazol-5-yl]-piperidin-1-yl}-methanone;
{(S)-3-[3-(4-Fluoro-phenyl)-1,2,4-oxadiazol-5-yl]-piperidin-1-yl}-(3-methyl-thiophen-2-yl)-methanone;
{(S)-3-[3-(4-Fluoro-phenyl)-1,2,4-oxadiazol-5-yl]-piperidin-1-yl}-(1-methyl-1H-pyrrol-2-yl)-methanone;
{(S)-3-[3-(4-Fluoro-phenyl)-1,2,4-oxadiazol-5-yl]-piperidin-1-yl}-thiazol-2-yl-methanone;
{(S)-3-[3-(4-Fluoro-phenyl)-1,2,4-oxadiazol-5-yl]-piperidin-1-yl}-(4-methyl-thiazol-5-yl)-methanone;
{(S)-3-[3-(4-Fluoro-phenyl)-1,2,4-oxadiazol-5-yl]-piperidin-1-yl}-(6-morpholin-4-yl-pyridin-3-yl)-methanone;
{(S)-3-[3-(4-Fluoro-phenyl)-1,2,4-oxadiazol-5-yl]-piperidin-1-yl}-(1H-indol-5-yl)-methanone;
2-(4-Fluoro-phenyl)-1-{(S)-3-[3-(4-fluoro-phenyl)-1,2,4-oxadiazol-5-yl]-piperidin-1-yl}-ethanone;
3-(4-Fluoro-phenyl)-1-{(S)-3-[3-(4-fluoro-phenyl)-1,2,4-oxadiazol-5-yl]-piperidin-1-yl}-propan-1-one;
{(S)-3-[3-(4-Fluoro-phenyl)-1,2,4-oxadiazol-5-yl]-piperidin-1-yl}-isoquinolin-3-yl-methanone;
{(S)-3-[3-(4-Fluoro-phenyl)-1,2,4-oxadiazol-5-yl]-piperidin-1-yl}-quinoxalin-6-yl-methanone;
{(S)-3-[3-(4-Fluoro-phenyl)-1,2,4-oxadiazol-5-yl]-piperidin-1-yl}-benzoimidazol-6-yl-methanone;
{(S)-3-[3-(2,6-Difluoro-phenyl)-[1,2,4]oxadiazol-5-yl]-piperidin-1-yl}-(4-fluoro-phenyl)-methanone;
(4-Fluoro-phenyl)-{(S)-3-[3-(2-methoxy-phenyl)-[1,2,4]oxadiazol-5-yl]-piperidin-1-yl}-methanone;
(E)-3-(4-Fluoro-phenyl)-1-{(S)-3-[3-(4-fluoro-phenyl)-[1,2,4]oxadiazol-5-yl]-piperidin-1-yl}-propenone;
{(S)-3-[3-(4-Fluoro-phenyl)-[1,2,4]oxadiazol-5-yl]-piperidin-1-yl}-(4-imidazol-1-yl-phenyl)-methanone;
(4-Fluoro-phenyl)-{(S)-3-[3-(4-nitro-phenyl)-[1,2,4]oxadiazol-5-yl]-piperidin-1-yl}-methanone; and
(3,4-Difluoro-phenyl)-{(S)-3-[3-(4-nitro-phenyl)-[1,2,4]oxadiazol-5-yl]-piperidin-1-yl}-methanone;
or a pharmaceutically acceptable salt thereof.
3. A compound according to claim 1 or 2, which can exist as optical isomers, wherein said compound is either the racemic mixture or the individual optical isomers.

4. A pharmaceutical composition comprising a therapeutically effective amount of a compound according to claim 1 or 2 and pharmaceutically acceptable carriers and/or excipients.

5. A method for treating a mammal suffering from Schizophrenia, Delusional Disorder, Schizoaffective Disorder, or Schizophreniform Disorder, the method comprising administering a compound of claim 1 or 2 to the mammal.

6. A pharmaceutical composition comprising a compound of claim 1 or 2 and a pharmaceutically acceptable carrier.

7. The method of claim 5, which is a method of treating schizophrenia.

* * * * *